United States Patent
Woodside et al.

(10) Patent No.: US 10,716,849 B2
(45) Date of Patent: *Jul. 21, 2020

(54) METHODS OF ADMINISTERING NOVEL INTEGRIN ACTIVATOR VACCINE COMPOSITIONS

(71) Applicants: 7 Hills Pharma LLC, Houston, TX (US); Texas Heart Institute, Houston, TX (US)

(72) Inventors: Darren G. Woodside, Pearland, TX (US); Peter Vanderslice, Houston, TX (US); Upendra K. Marathi, Houston, TX (US)

(73) Assignee: 7 Hills Pharma LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,277

(22) Filed: Apr. 25, 2019

(65) Prior Publication Data

US 2019/0343952 A1    Nov. 14, 2019

Related U.S. Application Data

(62) Division of application No. 15/140,711, filed on Apr. 28, 2016, now Pat. No. 10,342,866.

(60) Provisional application No. 62/154,554, filed on Apr. 29, 2015.

(51) Int. Cl.
| | | |
|---|---|---|
| *A61K 39/39* | (2006.01) |
| *A61K 31/16* | (2006.01) |
| *A61K 31/36* | (2006.01) |
| *A61K 31/381* | (2006.01) |
| *C07K 16/00* | (2006.01) |
| *C07K 16/28* | (2006.01) |
| *A61K 31/17* | (2006.01) |
| *A61K 31/165* | (2006.01) |
| *A61K 39/00* | (2006.01) |
| *A61K 39/395* | (2006.01) |

(52) U.S. Cl.
CPC .............. *A61K 39/39* (2013.01); *A61K 31/16* (2013.01); *A61K 31/165* (2013.01); *A61K 31/17* (2013.01); *A61K 31/36* (2013.01); *A61K 31/381* (2013.01); *A61K 39/0011* (2013.01); *A61K 39/39558* (2013.01); *C07K 16/00* (2013.01); *C07K 16/2818* (2013.01); *A61K 2039/505* (2013.01); *A61K 2039/55511* (2013.01); *C07K 2317/732* (2013.01)

(58) Field of Classification Search
CPC ................................. A61K 31/16; A61K 31/39
USPC ......................................................... 514/183
See application file for complete search history.

(56) References Cited

U.S. PATENT DOCUMENTS

| | | |
|---|---|---|
| 7,452,904 B2 | 11/2008 | Catena Ruiz et al. |
| 2010/0168468 A1 | 7/2010 | Tsunenaga et al. |
| 2012/0258126 A1 | 10/2012 | Scholler et al. |
| 2013/0236434 A1 | 9/2013 | Biediger et al. |
| 2015/0250883 A1 | 9/2015 | Marathi |
| 2016/0000755 A1 | 7/2016 | Marathi |

OTHER PUBLICATIONS

Vanderslice. P. et al. Small molecule agonist of very late antigen-4 (VLA-4) integrin induces progenitor cell adhesion J. Biol. Chem., 2013 (Pub! ished May 23, 2013), vol. 288, No. 27, pp. 19414-19428 See abstract: and p. 19417, Figure 1.
PCT ISR dated Oct. 27, 2016.
PCT Written Opinion dated Oct. 27, 2016.
Nov. 9, 2018 PCT International Preliminary Examination Report.

*Primary Examiner* — Kevin E Weddington
(74) *Attorney, Agent, or Firm* — Robert W. Strozier

(57) ABSTRACT

Methods for priming of vaccines including administering to a patient a composition including one or more integrin activating compounds capable of adjuvanting an antigen and capable of adjuvanting one or more antigens contained in a vaccine preparation.

20 Claims, 3 Drawing Sheets

METHODS OF ADMINISTERING NOVEL INTEGRIN ACTIVATOR VACCINE COMPOSITIONS

RELATED APPLICATIONS

This application is a divisional application of U.S. patent application Ser. No. 15/140,711 filed Apr. 28, 2016 (28 Apr. 2016), which claims priority to and the benefit of U.S. Provisional Patent Application Ser. No. 62/154,554 filed Apr. 29, 2015 (29 Apr. 2015).

BACKGROUND OF THE INVENTION

1. Field of the Invention

Embodiments of this invention relates to small molecule integrin ligand mimetics that facilitate integrin-ligand interactions, which may be used to prepare vaccines, adoptive cell therapies, and immunotherapies for cancer, and a variety of other conditions.

2. Description of the Related Art

There is a major unmet need for a safe and efficacious adjuvant capable of potentiating the immune response in infectious, autoimmune, and allergic diseases, and in other conditions such as cancer. Commonly, adjuvants are compounds or other agents used to enhance the immune response to vaccine antigens (or immunogens). Despite the descriptions of over one hundred adjuvants in the scientific literature, only alum (aluminum salts or aluminum gels) is currently licensed for use in the United States. This is because most adjuvants have unacceptable side effect profiles and lack biocompatibility. In fact, even alum, which can be found in diphtheria-tetanus-pertussis, human papillomavirus, and hepatitis vaccines, can be associated with injection site reactions and is facing increasing scrutiny regarding the potential for cumulative aluminum toxicity.

In the cancer field, there is an unmet need for a safe efficacious adjuvant capable of boosting the immune response (including both cellular and humoral) against cancer vaccine antigens. In general, cancer vaccines have been administered without an adjuvant or with specific cytokines included as adjuvants.

Recombinant, single immunogen cancer vaccines have also been described. One such product which failed in Phase 3 clinical trials is the GVAX® vaccine (Cell Genesys, Inc., South San Francisco, Calif.). This cancer vaccine is comprised of a cell line(s) that have been genetically modified to secrete granulocyte-macrophage colony stimulating factor (GM-CSF). This cytokine/hormone plays a role in stimulating the body's immune response to the cancer vaccine. The cells are irradiated for safety. Cancer vaccination with GVAX® vaccine or other similar approaches have provided limited benefit over conventional chemotherapy.

Though some studies have utilized specific cytokines as cancer vaccine adjuvants, such as GM-CSF in the GVAX® vaccine, those cytokines typically enhance only specific features of the immune response, are costly, and may be unstable outside of very controlled storage conditions. Thus, there is significant need for improvement in the art for adjuvants displaying increased effectiveness and biocompatibility.

Purified soluble, recombinant and synthetic antigens are often much less immunogenic than live or killed whole organism vaccines despite their better tolerability. Thus, the move towards the development of safer subunit vaccines has created a major need for more potent adjuvants. In particular, there is an urgent need for adjuvants capable of boosting both the cellular and/or humoral immune response with more acceptable safety profiles.

The prerequisites for an ideal cancer adjuvant differ from conventional adjuvants for many reasons. First, the patients that will receive the vaccines are immuno-compromised because of, for example, impaired mechanisms of antigen presentation, non-responsiveness of activated T cells and enhanced inhibition of self-reactivity by regulatory T cells. Second, the tumor antigens are usually self-derived in nature, and are therefore poorly immunogenic. Third, tumors develop escape mechanisms to avoid the immune system, such as tumor immunoediting, which can involve low or non-expression of MHC class I molecules, and secretion of suppressive cytokines. Fourth, even when robust immune responses are elicited to a given tumor antigen, effector functions of the adaptive response can be limited by the activation of immuno-suppressive pathways (CTLA-4/B7, PD-1/PDL-1 axis, IDO1), and effector functions may not be long-lived. Thus, adjuvants for cancer vaccines need to be more potent than for prophylactic vaccines in not only priming the immune response, but facilitating effector functions, which consequently may be more toxic and may even induce autoimmune reactions.

As such, there is a clear need for approaches that can selectively target rate limiting steps in the priming of the immune response and potentiating effector functions. Cellular interactions between integrins α4β1, α4β7, α5β1, and/or αLβ2 and their cognate ligands are important mediators of cell-cell adhesion leading to effective priming and effector functions in the immune system.

SUMMARY OF THE INVENTION

Specifically, the present invention describes compositions and methods to enhance: (1) the priming of vaccines (including, but not limited to, cancer vaccines); (2) cytolytic activity of adoptive cell therapies (γδT-cells, CTLs, NK, iNKT); (3) immunotherapies (including, but not limited to, negative checkpoint blockage strategies such as anti-CTLA-4 and anti-PD-1 therapies); and (4) biologic therapies (including, but not limited, to trastuzumab and rituxamab), whereby the mechanism-of-action includes antibody dependent cellular cytotoxicity (ADCC).

BRIEF DESCRIPTION OF THE DRAWINGS

The invention can be better understood with reference to the following detailed description together with the appended illustrative drawings in which like elements are numbered the same.

DEFINITIONS USED IN THE INVENTION

Figure 1:
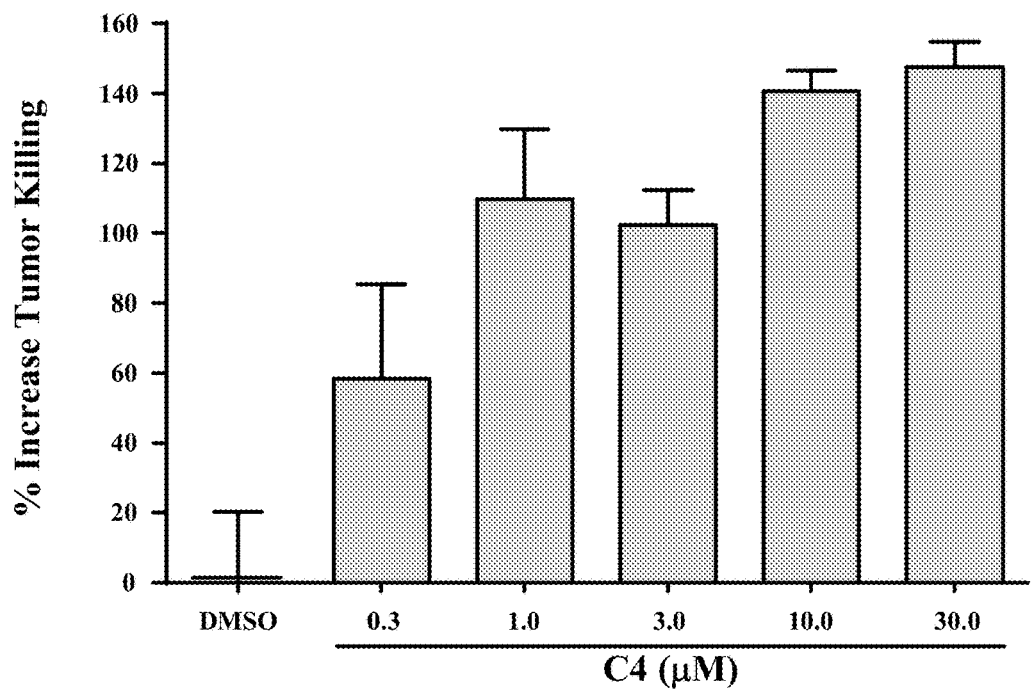
FIG. 1 depicts C4 enhancement of natural killer cell cytolysis of tumor target cells. Freshly isolated CD56+ natural killer cells were isolated from the peripheral blood of a healthy volunteer. Cells were either incubated with vehicle control (DMSO), or indicated concentrations of C4 for 4 h in the presence of tumor target cells (the erythroleukemic cell line K562). Data is presented as a percent increase in tumor cell killing.

In addition to having their customary and usual meaning, the following definitions apply where the context permits in the specification and claims:

"Pharmaceutical composition" refers to a mixture of one or more chemicals, or pharmaceutically acceptable salts thereof, with a suitable carrier, for administration to a mammal as a medicine.

"Cell therapeutic" refers to a mixture of one or more cells, or one or more chemicals or pharmaceutically acceptable salts thereof, with a suitable carrier for administration to a mammal as medicine.

"Therapeutically effective amount" refers to that amount of the compound being administered that will relieve at least to some extent one or more of the symptoms of the disorder being treated. For example, an amount of the compound effective to prevent, alleviate or ameliorate symptoms of disease or prolong the survival of the subject being treated.

The term "therapeutically ineffective amount" refers to that amount of the compound being administered that will not relieve at least to some extent one or more of the symptoms of the disorder being treated. For example, doses at which a compound is effective in one individual or population is not effective in other individual or population by means of intrinsic or acquired drug resistance.

The term "intrinsic resistance" is the innate ability of a cell or organism to resist activity of a particular a agent through its inherent structural or functional characteristics, which allow tolerance of a particular drug or drug class.

The term "acquired resistance" is the adaptive ability of a cell or organism to resist activity of a particular agent through induction of inherent structural or functional characteristics, which allow tolerance of a particular drug or drug class.

With respect to a disease or disorder, the term "treatment" refers to preventing, deterring the occurrence of the disease or disorder, arresting, regressing, or providing relief from symptoms or side effects of the disease or disorder and/or prolonging the survival of the subject being treated.

The term "alkyl" as used herein alone or in combination refers to $C_1$-$C_{12}$ straight or branched, substituted or unsubstituted saturated chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "alkenyl", alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$-$C_6$ unit for a particular functionality. For example lower alkyl means $C_1$-$C_6$ alkyl.

The term "cycloalkyl" as used herein alone or in combination refers to a substituted or unsubstituted aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. This term is meant to encompass cycloalkenyl and cycloalkynyl groups. "Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexyl methyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy", alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "carboxyl" as used herein refers to —$CO_2H$.

The term "thioalkoxy", refers to a thioether radical of formula alkyl-S—, wherein "alkyl" is as defined above.

The term "carboxaldehyde" as used herein refers to —C(O)R, wherein R is hydrogen.

The term "carboxamide" as used herein refers to —C(O)$NR_2$, wherein R is hydrogen, alkyl or any other suitable substituent.

The term "alkoxyalkoxy" as used herein refers to $R_b$O—$R_c$O—, wherein $R_b$ is lower alkyl as defined above and $R_c$ is alkylene wherein alkylene is —$(CH_2)_{n'}$— wherein n' is an integer from 1 to 6. Representative examples of alkoxyalkoxy groups include methoxymethoxy, ethoxymethoxy, and t-butoxymethoxy among others.

The term "alkylamino" as used herein refers to $R_d$NH—, wherein $R_d$ is a lower alkyl group, for example, ethylamino, butylamino, among others.

The term "alkenylamino" alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino", alone or in combination, refers to a radical of formula alkynyl-NH— or (alkynyl)$_2$N—, wherein the term "alkynyl" is as defined above, provided that the radical is not an amine. An example of such alkynylamino radicals is the propargyl amino radical.

The term "dialkylamino" as used herein refers to R$_e$R$_f$N—, wherein R$_e$ and R$_f$ are independently selected from lower alkyl, for example diethylamino, and methyl propylamino, among others.

The term "amino" as used herein refers to H$_2$N—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted. Aromatic rings may be fused with other aromatic or non-aromatic rings to form multicyclic rings, and are also encompassed by the term "aromatic," as used herein.

The term "aralkyl", alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl", alone or in combination, refers to an aryl substituted alkenyl radical, wherein the terms "aryl" and "alkenyl" are as defined above.

The term "arylamino", alone or in combination, refers to a radical of formula aryl-NRg-, wherein "aryl" is as defined above. Rg may be selected from the group consisting of H, lower alkyl, aryl and aralkyl among others. Examples of arylamino radicals include, but are not limited to, phenylamino(anilido), naphthlamino, 2-, 3-, and 4-pyridylamino and the like.

The term "biaryl", alone or in combination, refers to a radical of formula aryl-aryl, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl", alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxyl, alkoxycarbonyl, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "aminal" as used herein refers to a hemi-acetal of the structure RCH(NH$_2$)(OH).

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in ADVANCED ORGANIC CHEMISTRY by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)O—. Rings may be substituted multiple times.

The term "mammals" includes humans and other animals.

The term "heteroatom" as used herein encompasses nitrogen, sulfur and oxygen.

The term "alpha" as used herein indicates the position immediately adjacent to the position described.

The term "inactive ingredient" as used herein indicated a harmless drug that is ordinarily used as an inactive ingredient, such as a coloring, emulsifier, excipient, flavoring, lubricant, preservative, or solvent, in the preparation of other drugs shall be exempt from section 502(f)(1) of the act (21 CFR 201.117).

The term "excipient" as used herein means any substance other than the active drug or product which has been appropriately evaluated for safety and is included in a drug delivery system to either aid the processing of the drug delivery system during its manufacture; protect, support, or enhance stability, bioavailability, or patient acceptability; assist in product identification; or enhance any other attribute of the overall safety and effectiveness of the drug delivery system during storage or use (40 CFR 63.1251).

The term "effector cell" as used herein means a cell that can bind to and either engulf or induce cytolysis of a target cell. Effector cell types may include, but are not limited to: 1) a cytotoxic T-lymphocyte that binds to target cells and is activated by an antigen specific T cell receptor, 2) monocytes, macrophage, natural killer (NK) cells, and neutrophils that bind to and lyse target cells through interactions of fragment crystallizable (Fc) receptors and monoclonal antibody opsonized target cells, 3) NK and NK-variants that bind to and lyse target cells independent of antigen specificity, 4) Tumor Infiltrating Lymphocytes (TILs) which are lymphocytes isolated from tumors and expanded ex vivo that express cell surface markers including, but not limited to CD3, CD8, or CD4,5) T cells genetically engineered with tumor specific T cell receptors or chimeric antigen receptors that possess cell surface markers including but not limited to CD3, CD8, or CD4.

The term "adoptive T cell" is a effector cell that is derived from a naive T cell or activated T cell capable of effector functions.

The term "solid tumor" as used herein means an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas.

The term "small molecule agonist" as used herein is not a conventional ligand, and is synonymous to a stabilizer of a cognate ligand-receptor interaction.

Abbreviations Used in the Invention

The following abbreviations are used herein: Ac is acetyl, AcOH is acetic acid, ADCC is antibody dependent cellular cytotoxicity, 6-Ahx-OH is 6-aminohexanoic acid, APC is antigen presenting cell, BATDA is bis (acetoxymethyl) 2,2':6',2"-terpyridine-6,6"-dicarboxylate, BCG is bacillus calmette-guérin, Bn is benzyl, Boc is tert-butyloxycarbonyl, nBu is n-butyl, nBuLi is n-butyllithium, 1.6M in hexanes (unless other concentration noted), Cbz is benzyloxycarbonyl, CD is cluster of differentiation, CDI is N,N'-carbonyl-diimidazole, COMU is (1-cyano-2-ethoxy-2-oxoethylidenaminooxy)dimethylamino-morpholino-carbenium hexafluorophosphate, CTL is cytotoxic T lymphocyte, CTLA-4 is cytotoxic T lymphocyte-associated antigen-4, Dab is 2,4-diaminobutyryl, DBU is 1,8-diazabicyclo[5.4.0]undec-7-ene, DCE is 1,2-dichloroethane, DCHA is dicyclohexylamine, DCM is dichloromethane (methlyene chloride), dioxane is 1,4-dioxane, DIPEA is N,N-diisopropylethylamine, DMED is N,N'-dimethylethylene diamine, DMF is N,N-dimethylformamide, DMSO is dimethylsulfoxide Et is ethyl, EtOH is ethanol, FBS is fetal bovine serum, Fc is fragment crystallizable, FGF is fibroblast growth factor, Fmoc is 9H-fluoren-9-ylmethyloxycarbonyl, G-CSF is granulocyte colony stimulating factor, Glu is glutamic acid, Gly is glycine, HBTU is O-(Benzotriazol-1-yl)-N,N,N',N'-tetramethyluronium hexafluorophosphate, HMDS is hexamethyldisilazane, ICAM-1 is intercellular adhesion molecule-1, IDO is indoleamine 2,3-dioxygenase, iNKT is invariant natural killer T cell, iPr is isopropyl, KHMDS is potassium bis(trimethylsilyl)amide, LFA is lymphocyte function-associated antigen where LFA-1 is the integrin $\alpha L\beta 2$, Lys is lysine, LHMDS is lithium bis(trimethylsilyl)amide, MAdCAM-1 is mucosal addressin cell adhesion molecule-1, Me is methyl, MeOH is methanol, MHC is major histocompatibility complex, NK is natural killer, Nle is norleucine, NMM is 4-methylmorpholine, NSMC is N-succinimidyl-N-methylcarbamate, OAc is acetate, Orn is Ornithine, PBS is phosphate buffered saline, PD1 is programmed death 1, PDL1 is programmed death ligand 1, pTsOH is para-toluenesulfonic acid, Ph is phenyl, RT is room temperature, SDF1α is stromal cell derived factor-1α, tBu is tert-butyl, TBS is tris-buffered saline, TDA is 2,2':6',2"-terpyridine-6,6"-dicarboxylic acid, TEA is triethylamine, TIL is tumor infiltrating lymphocyte, Tfa is trifluoroacetyl, Th1 is T helper 1, Th2 is T helper 2, THF is tetrahydrofuran, Tol is toluene, Tyr is tyrosine, VCAM-1 is vascular cell adhesion molecule-1, Veh is vehicle, VLA is very late activation antigen where VLA-4 is the integrin $\alpha 4\beta 1$ and VLA-5 is the integrin $\alpha 5\beta 1$, and Z is benzyloxycarbonyl.

DETAILED DESCRIPTION OF THE INVENTION

We have invented small molecule integrin ligand mimetics that facilitate integrin-ligand interactions which can be used to prepare vaccines, adoptive cell therapies, and immunotherapies for cancer, and a variety of other conditions. The inventors have found that certain small molecules or chemical compounds are capable of enhancing the therapeutic efficacy of vaccines, adoptive cell therapies, immunotherapies for cancer, antibody dependent cellular cytotoxicity (ADCC), and/or a variety of other conditions.

In certain embodiments, the present invention relates to pharmaceutical preparations of a vaccine comprising an antigen, and an effective amount of one or a plurality of enhancing compounds, where the enhancing compounds are capable of enhancing integrin-mediated binding of integrins of a cell to their respective ligand, where the integrins include $4\beta 1$, $\alpha 4\beta 7$, $5\beta 1$, and/or $\alpha L\beta 2$, where the ligands include VCAM-1, fibronectin, MAdCAM-1, ICAM-1, and/or ICAM-2, where the antigen is a purified protein, a purified peptide, a cell, or a cell lysate. In other embodiments, the preparation is an anti-cancer vaccine. In other embodiments, the pharmaceutical preparation of claim 1, further comprising an adjuvant comprising a non-specific adjuvant substance and/or a specific adjuvant substance, where the substances are capable of eliciting an immune response in response to the antigen. In other embodiments, the non-specific adjuvant substance is selected from the group consisting of BCG, complete freund's adjuvant, alum, and/or noscapine, and the specific adjuvant substance is selected from the group consisting of G-CSF, FGF, Toll-like receptor agonists, and/or immune checkpoint inhibitors targeting proteins selected from the group consisting of CTL-4, PD-1, PDL-1, and/or IDO-1. In certain embodiments, the enhancing compounds are specific adjuvants.

In certain embodiments, the present invention relates methods to treat a patient with an effective amount of one or a plurality of enhancing compounds, wherein the associated enhancing compounds are capable of enhancing integrin-mediated binding of integrins of a cell to their respective ligand, wherein the integrins include α4β1, α4β7, α5β1, and/or αLβ2, wherein the ligands include VCAM-1, fibronectin, MAdCAM-1, ICAM-1, and/or ICAM-2, in combination with a therapeutically ineffective dose of immune checkpoint inhibitor, cytotoxic chemotherapy, cancer vaccine, wherein the patient has been diagnosed with cancer.

In certain embodiments, the present invention relates methods to treat a patient with an effective amount of one or a plurality of enhancing compounds, wherein the associated enhancing compounds are capable of enhancing integrin-mediated binding of integrins of a cell to their respective ligand, wherein the integrins include α4β1, α4β7, α5β1, and/or αLβ2, wherein the ligands include VCAM-1, fibronectin, MAdCAM-1, ICAM-1, and/or ICAM-2, in combination with a therapeutically ineffective dose of immune checkpoint inhibitor, cytotoxic chemotherapy, cancer vaccine, wherein the patient has been diagnosed with solid tumors in the lung, prostate, breast, colon, skin, brain, or pancreas, wherein the enhancing compound is intratumorally injected, locally infused to specific organs or tissues systemically administered by enteral or parenteral route of administration.

In certain embodiments, the present invention relates methods to treat a patient with an effective amount of one or a plurality of enhancing compounds, where the associated enhancing compounds are capable of enhancing interin-mediated binding of integrins of a cell to their respective ligand, wherein the integrins include α4β1, α4β7, α5β1, and/or αLβ2, wherein the ligands include VCAM-1, fibronectin, MAdCAM-1, ICAM-1, ICAM-2, and/or vitronectin, in combination with a therapeutically ineffective dose of immune checkpoint inhibitor, cytotoxic chemotherapy, wherein the patient has been diagnosed with hematologic cancers, wherein the integrin mimetic is systemically administered by enteral or parentral route of administration.

In certain embodiments, the present invention relates pharmaceutical preparations comprising NK cells, activated NK cells, engineered NK cells, or NK cell lines (and derivatives thereof) treated with an effective amount of one or a number of compounds capable of activating integrin mediated interactions with their cognate ligands.

In certain embodiments, the present invention relates methods to treat a patient with a pharmaceutical preparation comprising NK cells, activated NK cells, engineered NK cells, or NK cell lines (and derivatives thereof) delivered in combination with (either prior to, during, or after) an effective amount of one or a number of compounds capable of activating integrin mediated interactions with their cognate ligands.

In certain embodiments, the present invention relates methods to treat a patient with a pharmaceutical preparation comprising a therapeutically ineffective amount of NK cells, activated NK cells, engineered NK cells, or NK cell lines (and derivatives thereof) delivered in combination with (either prior to, during, or after) an effective amount of one or a number of compounds capable of activating integrin mediated interactions with their cognate ligands.

In certain embodiments, the present invention relates pharmaceutical preparations comprising invariant natural killer T (iNKT) cells, activated iNKT cells, engineered iNKT cells, or iNKT cell lines (and derivatives thereof) treated with an effective amount of one or a number of compounds capable of activating integrin mediated interactions with their cognate ligands.

In certain embodiments, the present invention relates methods to treat a patient with a pharmaceutical preparation comprising iNKT cells, activated iNKT cells, engineered iNKT cells, or iNKT cell lines (and derivatives thereof) delivered in combination with (either prior to, during, or after) an effective amount one or a number of compounds capable of activating integrin mediated interactions with their cognate ligands.

In certain embodiments, the present invention relates methods to treat a patient with a pharmaceutical preparation comprising a therapeutically ineffective amount of iNKT cells, activated iNKT cells, engineered iNKT cells, or iNKT cell lines (and derivatives thereof) delivered in combination with (either prior to, during, or after) an effective amount one or a number of compounds capable of activating integrin mediated interactions with their cognate ligands.

In certain embodiments, the present invention relates methods pharmaceutical preparations comprising γδT cells, activated iNKT cells, engineered γδT cells, or γδT cell lines (and derivatives thereof) treated with an effective amount of one or a number of compounds capable of activating integrin mediated interactions with their cognate ligands.

In certain embodiments, the present invention relates methods to treat a patient with a pharmaceutical preparation comprising γδT cells, activated iNKT cells, engineered γδT cells, or γδT cell lines (and derivatives thereof) delivered in combination with (either prior to, during, or after) an effective amount one or a number of compounds capable of activating integrin mediated interactions with their cognate ligands.

In certain embodiments, the present invention relates methods to treat a patient with a pharmaceutical preparation comprising γδT cells, activated iNKT cells, engineered γδT cells, or γδT cell lines (and derivatives thereof) delivered in combination with (either prior to, during, or after) an effective amount one or a number of compounds capable of activating integrin mediated interactions with their cognate ligands.

In certain embodiments, the present invention relates pharmaceutical preparations comprising cytotoxic T lymphocytes (CTLs) (including, but not limited to, tumor infiltrating lymphocytes, lymphocytes expanded in an antigen specific manner, lymphocytes engineered to express chimeric antigen receptors) treated with an effective amount of one or a number of compounds capable of activating integrin mediated interactions with their cognate ligands for the purpose of enhancing CTL tumoricidal activity.

In certain embodiments, the present invention relates methods to treat a patient with a pharmaceutical preparation comprising cytotoxic T lymphocytes (CTLs) (including, but not limited to, tumor infiltrating lymphocytes, lymphocytes expanded in an antigen specific manner, lymphocytes engineered to express chimeric antigen receptors) delivered in combination with (either prior to, during, or after) an effective amount of one or a number of compounds capable of activating integrin mediated interactions with their cognate ligands for the purpose of enhancing CTL tumoricidal activity.

In certain embodiments, the present invention relates methods to treat a patient with a pharmaceutical preparation comprising a therapeutically ineffective amount of cytotoxic T lymphocytes (CTLs) (including, but not limited to, tumor infiltrating lymphocytes, lymphocytes expanded in an antigen specific manner, lymphocytes engineered to express chimeric antigen receptors) delivered in combination with (either prior to, during, or after) an effective amount of one or a number of compounds capable of activating integrin mediated interactions with their cognate ligands for the purpose of enhancing CTL tumoricidal activity.

In certain embodiments, the present invention relates methods to treat a patient with a therapeutic antibody, wherein the antibody contains a Fc region, wherein the antibody is, without limitation, trastuzumab, cetuximab, ipilimumab, nivolumab rituximab, alemtuzumab, atumumab, or tositumomab, and an effective amount of one or a number of compounds capable of activating integrin mediated interactions with their cognate ligands.

In certain embodiments, the present invention relates methods to treat a patient with therapeutically ineffective amount of therapeutic antibody, wherein the antibody contains a Fc region, wherein the antibody is, without limitation, trastuzumab, cetuximab, ipilimumab, nivolumab rituximab, alemtuzumab, atumumab, or tositumomab, and an effective amount of one or a number of compounds capable of activating integrin mediated interactions with their cognate ligands.

In certain embodiments, the present invention relates pharmaceutical compositions comprising a therapeutically ineffective amount of therapeutic antibody, wherein the antibody contains a Fc fragment and an effective amount of one or a number of compounds capable of activating integrin mediated interactions with their cognate ligands.

In certain embodiments, the chemical compounds are given by the general Formula (I):

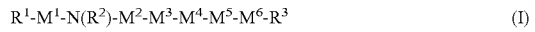

$$R^1\text{-}M^1\text{-}N(R^2)\text{-}M^2\text{-}M^3\text{-}M^4\text{-}M^5\text{-}M^6\text{-}R^3 \qquad (I)$$

where:
$R^1$ is selected from the group consisting of aryl and aralkyl,
$R^2$ is alkyl, aryl, or aralkyl,
$M^1$ is $CH_2$,
$M^2$ is CO,
$M^3$ is O, S, or $NR^6$, where $R^6$ when present is hydrogen or lower alkyl,
$M^4$ is absent or $CH_2$,
$M^5$ is $(CR^{11}R^{12})$, where $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, where s is an integer of 1 to 6, $R^{21}$ and $R^{22}$ when present are independently selected from the group consisting of hydrogen or lower alkyl, $R^{23}$ when present is selected from the group consisting of hydroxyalkyl, alkoxyalkyl, alkyl, aryl, aralkyl and alkoxycarbonylalkyl, provided that when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl, $R^{24}$ when present is selected from the group consisting of alkyl, aryl, aralkyl, heterocyclyl, cycloalkyl, cycloalkylalkyl, and heterocyclylalkyl,
$M^6$ is $(CH_2)_q$, wherein q is an integer from 0 to 6,
$R^3$ is selected from the group consisting of hydrogen, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, $SR^{16}$, heterocyclyl, hydroxyl, hydroxyalkyl, guanadino, alkyl and aryl, where $R^{13}$ and $R^{15}$ when present are independently hydrogen or lower alkyl, $R^{14}$ and $R^{16}$ when present are independently selected from the group consisting of hydrogen, alkyl, aryl, aralkyl, cycloalkyl, heterocyclyl, cycloalkylalkyl, and heterocyclylalkyl, $R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO (aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino).

Embodiments of the present invention provide methods to increase the potency and or efficacy of effector cells by increasing their intratumoral bioavailability, where the methods include the steps of suffusing a composition directly into a target tissue, or systemically infusing into of a patient, where the composition includes effector cells treated with an effective amount of one or a plurality of chemical compounds capable of enhancing integrin-mediated binding of cells to their respective ligands and an additional amount of one or a plurality of chemical compounds capable of enhancing integrin-mediated binding of cells to their respective ligands. In certain embodiments, integrins targeted by these compounds include, but are not limited to, α4β1, α4β7, α5β1, αLβ2 and αVβ3. In various embodiments, ligands include, but are not limited to, VCAM-1, fibronectin, MAdCAM-1, ICAM-1, ICAM-2, and vitronectin.

In other embodiments, the chemical compounds are given by the general Formula (I):

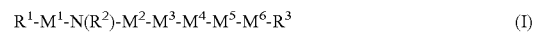

$$R^1\text{-}M^1\text{-}N(R^2)\text{-}M^2\text{-}M^3\text{-}M^4\text{-}M^5\text{-}M^6\text{-}R^3 \qquad (I)$$

where:
$R^1$ is selected from the group consisting of aryl and aralkyl,
$R^2$ is alkyl, aryl, or aralkyl,
$M^1$ is $CH_2$,
$M^2$ is CO,
$M^3$ is O, S, or $NR^6$, where $R^6$ when present is hydrogen or lower alkyl,
$M^4$ is absent or $CH_2$,
$M^5$ is $(CR^{11}R^{12})$, where $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, where s is an integer of 1 to 6, $R^{21}$ and $R^{22}$ when present are independently selected from the group consisting of hydrogen or lower alkyl, $R^{23}$ when present is selected from the group consisting of hydroxyalkyl, alkoxyalkyl, alkyl, aryl, aralkyl and alkoxycarbonylalkyl, provided that when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl, $R^{24}$ when present is selected from the group consisting of alkyl, aryl, aralkyl, heterocyclyl, cycloalkyl, cycloalkylalkyl, and heterocyclylalkyl,
$M^6$ is $(CH_2)_q$, wherein q is an integer from 0 to 6,
$R^3$ is selected from the group consisting of hydrogen, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, $SR^{16}$, heterocyclyl, hydroxyl, hydroxyalkyl, guanadino, alkyl and aryl, where $R^{13}$ and $R^{15}$ when present are independently hydrogen or lower alkyl, $R^{14}$ and $R^{16}$ when present are independently selected from the group consisting of hydrogen, alkyl, aryl, aralkyl, cycloalkyl, heterocyclyl, cycloalkylalkyl, and heterocyclylalkyl, $R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino).

In other embodiments, the chemical compounds are given by the general formula (I):

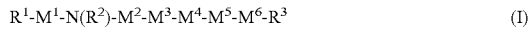

$$R^1\text{-}M^1\text{-}N(R^2)\text{-}M^2\text{-}M^3\text{-}M^4\text{-}M^5\text{-}M^6\text{-}R^3 \qquad (I)$$

where $R^1$ is selected from the group consisting of aryl and aralkyl, $R^2$ is alkyl, aryl, or aralkyl, $M^1$ is CH$_2$, $M^2$ is CO, $M^3$ is O, S, or NR$^6$, where R$^6$ when present is hydrogen or lower alkyl, $M^4$ is absent or CH$_2$, $M^5$ is (CR$^{11}$R$^{12}$), where R$^{11}$ is hydrogen, $R^{12}$ is selected from the group consisting of hydrogen, NR$^{21}$CONR$^{22}$R$^{23}$, NR$^{21}$COR$^{24}$, NR$^{21}$SO$_2$OR$^{24}$, NR$^{21}$SO$_2$R$^{24}$, NR$^{21}$COOR$^{24}$, OCOR$^{24}$, OR$^{24}$, O(CH$_2$CH$_2$O)$_s$R$^{24}$, COOR$^{24}$, alkyl, and hydroxyalkyl, where s is an integer of 1 to 6, R$^{21}$ and R$^{22}$ when present are independently selected from the group consisting of hydrogen or lower alkyl, R$^{23}$ when present is selected from the group consisting of hydroxyalkyl, alkoxyalkyl, alkyl, aryl, aralkyl and alkoxycarbonylalkyl, provided that when M$^3$ is NR$^6$, M$^4$ is absent, then R$^{23}$ is not 1-(1,3-benzodioxol-5-yl)-3-ethoxy-3-oxopropyl, R$^{24}$ when present is selected from the group consisting of alkyl, aryl, aralkyl, heterocyclyl, cycloalkyl, cycloalkylalkyl, and heterocyclylalkyl, and mixtures or combinations thereof, M$^6$ is (CH$_2$)$_q$, wherein q is an integer from 0 to 6, R$^3$ is selected from the group consisting of hydrogen, CONR$^{13}$R$^{14}$, NR$^{15}$COOR$^{16}$, NR$^{15}$COR$^{16}$, NR$^{15}$CONR$^{13}$R$^{14}$, NR$^{15}$SO$_2$R$^{16}$, OCOR$^{16}$, COOR$^{16}$, OR$^{16}$, SR$^{16}$, heterocyclyl, hydroxyl, hydroxyalkyl, guanadino, alkyl and aryl, where R$^{13}$ and R$^{15}$ when present are independently hydrogen or lower alkyl, R$^{14}$ and R$^{16}$ when present are independently selected from the group consisting of hydrogen, alkyl, aryl, aralkyl, cycloalkyl, heterocyclyl, cycloalkylalkyl, and heterocyclylalkyl, R$^1$, R$^2$, R$^3$, R$^{12}$, R$^{14}$, R$^{16}$, R$^{23}$ and R$^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures or combinations thereof. In other embodiments, the compounds have R$^1$ is aryl or aralkyl, R$^2$ is alkyl or aralkyl, M$^1$ is CH$_2$, M$^2$ is CO, M$^3$ is absent or is O or CH$_2$, M$^4$ is absent or is CH$_2$, M$^5$ is absent or is O or (CR$^{11}$R$^{12}$), R$^{11}$ is hydrogen, NR$^{21}$CONR$^{22}$R$^{23}$, NR$^{21}$COR$^{24}$, NR$^{21}$SO$_2$R$^{24}$ and NR$^{21}$COOR$^{24}$, M$^6$ is selected from the group consisting of (CH$_2$)$_q$, (CH$_2$)$_q$—CH=CH—(CH$_2$)$_r$, (CH$_2$)$_q$-arylene-(CH$_2$)$_r$ and (CH$_2$CH$_2$O)$_q$, q and r are independently integers from 0 to 6, R$^3$ is CONR$^{13}$R$^{14}$, R$^{21}$ and R$^{22}$ each of which, when present is independently selected from the group of hydrogen and lower alkyl, R$^{13}$, R$^{14}$, R$^{23}$ and R$^{24}$, each of which, when present is independently selected from the group consisting of hydrogen, alkyl, aryl, cycloalkyl, cycloalkylalkyl, heterocyclyl, heterocyclylalkyl and aralkyl, and R$^1$, R$^2$, R$^{13}$, R$^{14}$, R$^{23}$ and R$^{24}$ when present may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures or combinations thereof. In other embodiments, the compounds have R$^1$ is aryl or aralkyl, R$^2$ is alkyl or aralkyl, M$^1$ is CH$_2$, M$^2$ is SO$_2$ or CO, M$^3$ is absent or is CH$_2$, M$^4$ is absent or is CH$_2$, M$^5$ is absent or is (CR$^{11}$R$^{12}$), R$^{11}$, when present, is hydrogen, R$^{12}$, when present, is selected from the group consisting of hydrogen, alkyl, NR$^{21}$CONR$^{22}$R$^{23}$, NR$^{21}$COR$^{24}$, NR$^{21}$SO$_2$R$^{24}$ and NR$^{21}$COOR$^{24}$, M$^6$ is (CH$_2$)$_q$, or NR$^{34}$(CH$_2$)$_q$, q is an integer from 0 to 6, R$^3$ is selected from the group consisting of CONR$^{13}$R$^{14}$, SO$_2$NR$^{13}$R$^{14}$, NR$^{15}$COOR$^{16}$, NR$^{15}$COR$^{16}$, NR$^{15}$CONR$^{13}$R$^{14}$, and NR$^{15}$SO$_2$R$^{16}$, R$^{15}$, R$^{16}$, R$^{21}$ and R$^{22}$, each of which when present, is independently selected from the group of hydrogen, lower alkyl, and aralkyl, R$^{13}$, R$^{14}$, R$^{23}$ and R$^{24}$, each of which, when present is independently selected from the group consisting of hydrogen, alkyl, aryl, cycloalkyl, cycloalkylalkyl, heterocyclyl, heterocyclylalkyl and aralkyl, R$^{34}$, when present, is selected form the group consisting of alkyl, aralkyl, COR$^{35}$, and SO$_2$R$^{35}$, R$^{35}$ when present, is selected form the group consisting of alkyl, aryl, and aralkyl, and R$^1$, R$^2$, R$^{13}$, R$^{14}$, R$^{15}$, R$^{16}$, R$^{23}$, R$^{24}$, R$^{34}$ and R$^{35}$, when present, may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino), with the proviso that when M$^2$ is CO, then M$^6$ is NR$^{34}$(CH$_2$)$_q$, wherein q is not 0. In other embodiments, the chemical compounds are inactive ingredients or excipients. In other embodiments, the effective amount in carrier is greater than 1 fM and less than 100 nM. In other embodiments, the effective amount in carrier is greater than 1 fM and less than 50 nM. In other embodiments, the effective amount in carrier is greater than 1 fM and less than 25 nM.

In other embodiments, the chemical compounds are given by the general formula (I):

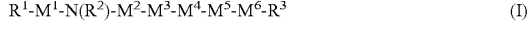

$$R^1\text{-}M^1\text{-}N(R^2)\text{-}M^2\text{-}M^3\text{-}M^4\text{-}M^5\text{-}M^6\text{-}R^3 \qquad (I)$$

where R$^1$ is selected from the group consisting of aryl and aralkyl, R$^2$ is alkyl, aryl, or aralkyl, M$^1$ is CH$_2$, M$^2$ is CO, M$^3$ is O, S, or NR$^6$, where R$^6$ when present is hydrogen or lower alkyl, $^4$ is absent or CH$_2$, M$^5$ is (CR$^{11}$R$^{12}$), where R$^{11}$ is hydrogen, R$^{12}$ is selected from the group consisting of hydrogen, NR$^{21}$CONR$^{22}$R$^{23}$, NR$^{21}$COR$^{24}$, NR$^{21}$SO$_2$R$^{24}$, NR$^{21}$COOR$^{24}$, OCOR$^{24}$, OR$^{24}$, O(CH$_2$CH$_2$O)$_s$R$^{24}$, COOR$^{24}$, alkyl, and hydroxyalkyl, where s is an integer of 1 to 6, R$^{21}$ and R$^{22}$ when present are independently selected from the group consisting of hydrogen or lower alkyl, R$^{23}$ when present is selected from the group consisting of hydroxyalkyl, alkoxyalkyl, alkyl, aryl, aralkyl and alkoxycarbonylalkyl, provided that when M$^3$ is NR$^6$, M$^4$ is absent, then R$^{23}$ is not 1-(1,3-benzodioxol-5-yl)-3-ethoxy-3-oxopropyl, R$^{24}$ when present is selected from the group consisting of alkyl, aryl, aralkyl, heterocyclyl, cycloalkyl, cycloalkylalkyl, and heterocyclylalkyl, and mixtures or combinations thereof, M$^6$ is (CH$_2$)$_q$, wherein q is an integer from 0 to 6, R$^3$ is selected from the group consisting of hydrogen, CONR$^{13}$R$^{14}$, NR$^{15}$COOR$^{16}$, NR$^{15}$COR$^{16}$, NR$^{15}$CONR$^{13}$R$^{14}$, NR$^{15}$SO$_2$R$^{16}$, OCOR$^{16}$, COOR$^{16}$, OR$^{16}$, SR$^{16}$, heterocyclyl, hydroxyl, hydroxyalkyl, guanadino, alkyl and aryl, where R$^{13}$ and R$^{15}$ when present are independently hydrogen or lower alkyl, R$^{14}$ and R$^{16}$ when present are independently selected from the group consisting of hydrogen, alkyl, aryl, aralkyl, cycloalkyl, heterocyclyl, cycloalkylalkyl, and heterocyclylalkyl, R$^1$, R$^2$, R$^3$, R$^{12}$, R$^{14}$, R$^{16}$, R$^{23}$ and R$^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures or combinations thereof. In other embodiments, the chemical compounds have R$^1$ is aryl or aralkyl, R$^2$ is alkyl or aralkyl, M$^1$ is CH$_2$, M$^2$ is CO, M$^3$ is absent or is O or CH$_2$, M$^4$ is absent or is CH$_2$, M$^5$ is absent or is O or (CR$^{11}$R$^{12}$), R$^{11}$ is hydrogen, R$^{12}$ is selected from the group consisting of hydrogen, NR$^{21}$CONR$^{22}$R$^{23}$, NR$^{21}$COR$^{24}$, NR$^{21}$SO$_2$R$^{24}$ and NR$^{21}$COOR$^{24}$, M$^6$ is selected from the group consisting of (CH$_2$)$_q$, (CH$_2$)$_q$—CH=CH—(CH$_2$)$_r$, (CH$_2$)$_q$-arylene-(CH$_2$)$_r$, and (CH$_2$CH$_2$O)$_q$, q and r are independently integers from 0 to 6, R$^3$ is CONR$^{13}$R$^{14}$, R$^{21}$ and R$^{22}$ each of which, when present is independently selected from the group of hydrogen and lower alkyl, R$^{13}$, R$^{14}$, R$^{23}$ and R$^{24}$, each of which, when present is independently selected from the group consisting of hydrogen, alkyl, aryl, cycloalkyl, cycloalkylalkyl, heterocyclyl, heterocyclylalkyl and aralkyl, and R$^1$, R$^2$, R$^{13}$, R$^{14}$, R$^{23}$ and R$^{24}$ when present may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures or combinations thereof. In other embodiments, the chemical compounds have R$^1$ is aryl or aralkyl, R$^2$ is alkyl or aralkyl, M$^1$ is CH$_2$, M$^2$ is SO$_2$ or CO, M$^3$ is absent or is CH$_2$, M$^4$ is absent or is CH$_2$, M$^5$ is absent or is (CR$^{11}$R$^{12}$), R$^{11}$, when present, is hydrogen, R$^{12}$, when present, is selected from the group consisting of hydrogen, alkyl, NR$^{21}$CONR$^{22}$R$^{23}$, NR$^{21}$COR$^{24}$, NR$^{21}$SO$_2$R$^{24}$ and NR$^{21}$COOR$^{24}$, M$^6$ is (CH$_2$)$_q$, or NR$^{34}$(CH$_2$)$_q$, q is an integer from 0 to 6, R$^3$ is selected from the group consisting of CONR$^{13}$R$^{14}$, SO$_2$NR$^{13}$R$^{14}$, NR$^{15}$COOR$^{16}$, NR$^{15}$COR$^{16}$, NR$^{15}$CONR$^{13}$R$^{14}$, and NR$^{15}$SO$_2$R$^{16}$, R$^{15}$, R$^{16}$, R$^{21}$ and R$^{22}$, each of which when present, is independently selected from the group of hydrogen, lower alkyl, and aralkyl, R$^{13}$, R$^{14}$, R$^{23}$ and R$^{24}$, each of which, when present is independently selected from the group consisting of hydrogen, alkyl, aryl, cycloalkyl, cycloalkylalkyl, heterocyclyl, heterocyclylalkyl and aralkyl, R$^{34}$, when present, is selected form the group consisting of alkyl, aralkyl, COR$^{35}$, and SO$_2$R$^{35}$, R$^{35}$ when present, is selected form the group consisting of alkyl, aryl, and aralkyl, and R$^1$, R$^2$, R$^{13}$, R$^{14}$, R$^{15}$, R$^{16}$, R$^{23}$, R$^{24}$, R$^{34}$ and R$^{35}$, when present, may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino), with the proviso that when M$^2$ is CO, then M$^6$ is NR$^{34}$(CH$_2$)$_q$, wherein q is not 0. In other embodiments, the chemical compounds are inactive ingredients or excipients. In other embodiments, the effective amount in carrier is greater than 1 fM and less than 100 nM. In other embodiments, the effective amount in carrier is greater than 1 fM and less than 50 nM. In other embodiments, the effective amount in carrier is greater than 1 fM and less than 25 nM.

The concentration of the disclosed compounds in the ex vivo treatment media alone or in combination with therapeutic cells in a suitable media to infuse a human or lower animal may be between 1 fM (1 femto molar or 1×10$^{-15}$ M) and less than 10 µM. If desired, the effective concentration can be divided into multiple doses for purposes of administration; consequently, single dose compositions may contain such amounts or submultiples thereof to make up the daily dose of cell or compound.

In other embodiments, the R$^1$, R$^2$, R$^3$, R$^{12}$, R$^{14}$, R$^{16}$, R$^{23}$ and R$^{24}$ groups when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures or combinations thereof.

In some embodiments, the compound is selected from the group consisting of methyl (6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10S)-1-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-9-methyl-3,8-dioxo-1-(2-thienyl)-2-(2-thienyl)-2-(2-thienylmethyl)-4-oxa-2,7,9-triazadodecan-12-oate; ethyl(6S,10R)-10-(1,3-benzodioxol-5-yl)-6-butyl-7-methyl-3,8-dioxo-1-(-2-thienyl)-2-(2-thienylmethyl)-4-oxa-2,7,9-triazadodecan-12-oate; methyl (10S)-10-(1,3-benzodioxol-5-yl)-3,8-dioxo-1-(2-thienyl)-2-

(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-2-methyl-3,8-dioxo-1-(2-thienyl)-4-oxa-2,7,9-triazadodecan-12-oate; methyl(6S)-6-butyl-3,8-dioxo-1-(2-thienyl)-2-(2-thienylmethyl)-4-oxa-2,7,-9-triazadodecan-12-oate; (2S)-2-{[(1,3-benzodioxol-5-ylmethyl)carbamoyl]amino}hexyl bis(2-thienylmethyl)carbamate; methyl(6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl]carbamoyl}amino)hexyl-bis(2-thienylmethyl)carbamate; (2S)-2-[(benzylcarbamoyl)amino]hexyl-bis(2-thienylmethyl)carbamate; (2S)-2-[(morpholin-4-ylcarbonyl)amino]hexyl-bis(2-thienylmethyl)carbamate; (2S)-2-{[(3-methoxypropyl)carbamoyl]amino}hexyl-bis(2-thienylmethyl)carbamate; (2S)-2-{[(2-methoxyethyl)carbamoyl]amino}hexyl-bis(2-thienylmethyl)carbamate; tert-butyl[(2S)-1-{[bis(2-thienylmethyl)carbamoyl]oxy}hexan-2-yl]carbamate; (2S)-2-[(tert-butylcarbamoyl)amino]hexyl-bis(2-thienylmethyl)carbamate; (2S)-2-[(isopropylcarbamoyl)amino]hexyl-bis(2-thienylmethyl)carbamate; (2S)-2-[(methylcarbamoyl)amino]hexyl-bis(2-thienylmethyl)carbamate; tert-butyl[(2R)-1-{[bis(2-thienylmethyl)carbamoyl]oxy}hexan-2-yl]carbamate; benzyl{(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; (2S)-2-acetamidohexylbis(2-thienylmethyl)carbamate; methyl(3R)-3-(1,3-benzodioxol-5-yl)-3-{[(2S)-2-{[bis(2-thienylmethyl)carbamoyl]amino}hexanoyl]amino}propanoate; methyl(3R)-3-(1,3-benzodioxol-5-yl)-3-{[(2R)-2-{[bis(2-thienylmethyl)carbamoyl]amino}hexanoyl]amino}propanoate; methyl(3S)-3-(1,3-benzodioxol-5-yl)-3-{[(2R)-2-{[bis(2-thienylmethyl)carbamoyl]amino}hexanoyl]amino}propanoate; methyl(6R,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(2S)-2-{[bis(2-thienylmethyl)-carbamoyl]amino}hexanoate; methyl(2R)-2-{[bis(2-thienylmethyl)carbamoyl]amino}hexanoate; 3-[(2S)-1-hydroxyhexan-2-yl]-1,1-bis(2-thienylmethyl)urea; 3-[(2R)-1-hydroxyhexan-2-yl]-1,1-bis(2-thienylmethyl)urea; methyl(2S)-6-{[(benzyloxy)carbonyl]amino}-2-{[bis(2-thienylmethyl)carbamoyl]amino}hexanoate; methyl{[bis(2-thienylmethyl)carbamoyl](methyl)amino}acetate; methyl{[bis(2-thienylmethyl)carbamoyl]amino}acetate; methyl{[bis(2-thienylmethyl)carbamoyl](butyl)amino}acetate; 3-(3-hydroxypropyl)-1,1-bis(2-thienylmethyl)urea; methyl(2R)-{[bis(2-thienylmethyl)carbamoyl]amino}(phenyl)acetate; tert-butyl{[bis(2-thienylmethyl)carbamoyl]amino}acetate; tert-butyl{[bis(2-thienylmethyl)carbamoyl](butyl)amino}acetate; benzyl{(5S)-6-{[bis(4-methoxybenzyl)carbamoyl]oxy}-5-[(tert-butoxycarbonyl)amino]hexyl}carbamate; tert-butyl[(2S)-1-{[bis(4-methoxybenzyl)carbamoyl]oxy}hexan-2-yl]carbamate; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl]carbamoyl}amino)hexyl(4-methoxybenzyl)carbamate; (2S)-2-[(tert-butoxycarbonyl)amino]hexyl dibenzylcarbamate; methyl(6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl)carbamoyl]oxy}hexan-2-yl]carbamate; methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl) carbamoyl]oxy}hexan-2-yl]carbamate; methyl(6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; (2S)-2-[(tert-butoxycarbonyl)amino]hexyl (4-bromobenzyl)(2-thienylmethyl)carbamate; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexylphenyl(2-thienylmethyl)carbamate; methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl) carbamoyl]oxy}hexan-2-yl]carbamate; methyl(6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tert-butoxycarbonyl)amino]-6-{[butyl(2-thienylmethyl)carbamoyl]oxy}hexyl]carbamate; (2S)-2-[(tert-butoxycarbonyl)amino]hexylbutyl(2-thienylmethyl)carbamate; methyl(3S,7S)-3-(1,3-benzodioxol-5-yl)-7-butyl-5,10-dioxo-[1-(2-thienylmethyl)-9-oxa-4,6,11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-[(tert-butoxycarbonyl) amino]hexyl(2-methoxyethyl)(2-thienylmethyl)carbamate; methyl(9S,13S)-13-(1,3-benzodioxol-5-yl)-9-butyl-6,11-dioxo-5-(-2-thienylmethyl)-2,7-dioxa-5, 10,12-triazapentadecan-15-oate; (2S)-2-[({3-[(methylsulfonyl) amino]benzyl}carbamoyl)amino]hexyl (2-methoxyethyl)(2-thienylmethyl)carbamate; (2S)-2-{[(4-bromobenzyl)carbamoyl]amino}hexyl-bis(2-thienylmethyl)carbamate; (2S)-2-{[(4-azidobenzyl)carbamoyl]amino}hexyl-bis(2-thienylmethyl)carbamate; tert-butyl[(2S)-1-{[bis(2-thienylmethyl)carbamoyl]thio}hexan-2-yl]carbamate; methyl(6S,1S)-10-(1,3-benzodioxol-5-yl)-6-butyl-3,8-dioxo-1-(2-thienyl)-2-(2-thienylmethyl)-4-thia-2, 7,9-triazadodecan-12-oate; and mixtures or combinations thereof.

In some embodiments, a chemical compound is provided having the general formula (I), where $R^1$ is aryl or aralkyl, $R^2$ is alkyl, aryl or aralkyl, $M^1$ is $CH_2$, $M^2$ is CO, $M^3$ is absent, $M^4$ is absent or is $CH_2$, $M^5$ is $(CR^{11}R^{12})$, $M^6$ is $(CH_2)_q$, wherein q is an integer of 0 to 6, $R^{11}$ is hydrogen, and $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $SCOR^{24}$, $SR^{24}$, $N_3$, CN, and $O(CH_2CH_2O)_sR^{24}$, wherein s is an integer of 1 to 6, $R^{21}$ and $R^{22}$ when present are independently selected from the group consisting of hydrogen, lower alkyl, or aralkyl, $R^{23}$ when present is selected from the group consisting of hydroxyalkyl, alkoxyalkyl, alkyl, aryl, aralkyl, and alkoxycarbonylalkyl, $R^{24}$ when present is selected from the group consisting of alkyl, aryl, aralkyl, heterocyclyl, cycloalkyl, cycloalkylalkyl and heterocyclylalkyl, provided that when $M^3$ and $M^4$ are absent, $R^{12}$ is not of the formula:

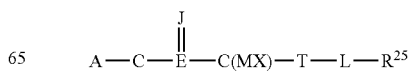

where A is selected from the group consisting of —O—, —S—, and —NR$^{26}$—, E is selected from the group consisting of —CH$_2$—, —O—, —S—, and —NR$^{27}$—, J is selected from the group consisting of —O—, —S—, and —NR$^{28}$—, T is selected from the group consisting of CO and (CH$_2$)$_b$, wherein b is an integer of zero to three, L is selected from the group consisting of —(CH$_2$)—, —O—, —S—, and —NR$^{29}$—, wherein n is an integer of zero to three, M is selected from the group consisting of CR$^{30}$R$^{31}$ and (CH$_2$)$_u$u wherein u is an integer of zero or one, X is selected from the group consisting of CO$_2$B, PO$_3$H$_2$, SO$_3$H, OPO$_3$H$_2$, CONHCOR$^{32}$, CONHSO$_2$R$^{33}$, oxazolyl, tetrazolyl and hydrogen, B, R$^{25}$, R$^{26}$, R$^{27}$, R$^{28}$, R$^{29}$, R$^{30}$, R$^{31}$, R$^{32}$ and R$^{33}$ are independently selected from the group consisting of hydrogen, halogen alkyl, alkenyl, alkynyl, alkoxy, alkenoxy, alkynoxy, thioalkoxy, aliphatic acyl, —CF$_3$, nitro, amino, cyano, N(C$_1$-C$_3$ alkyl)CO(C$_1$-C$_3$ alkyl), C$_1$-C$_3$ alkylamino, alkenylamino, alkynylamino, di(C$_1$-C$_3$ alkyl)amino, CO$_2$(C$_1$-C$_3$ alkylamino), CONH(C$_1$-C$_3$ alkylamino), CH.dbd.NOH, PO$_3$H$_2$, OPO$_3$H$_2$, CON(C$_1$-C$_3$ alkyl)$_2$, haloalkyl, alkoxycarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyc, heterocyclycalkyl, sulfonyl, sulfonamide, carbamate, aryloxyalkyl, carboxyl and CONH(benzyl), wherein B, X, R$^{25}$, R$^{26}$, R$^{27}$, R$^{28}$, R$^{29}$, R$^{30}$, R$^{31}$ and R$^{32}$ are unsubstituted or substituted with at least one electron donating or electron withdrawing group, R$^3$ is selected from the group of hydrogen, NR$^{15}$COOR$^{16}$, NR$^{15}$COR$^{16}$, NR$^{15}$CONR$^{13}$R$^{14}$, NR$^{15}$SO$_2$R$^{16}$, OCOR$^{16}$, COOR$^{16}$, alkyl, SR$^{16}$, heterocyclyl, hydroxyl, hydroxyalkyl, guanadino and aryl, wherein R$^{13}$ and R$^{15}$ when present are independently hydrogen, lower alkyl, or aralkyl, R$^{14}$ and R$^{16}$ when present are independently selected from the group consisting of hydrogen, alkyl, aralkyl, cycloalkyl, cycloalkylalkyl, heterocyclyl and heterocyclylalkyl provided that when R$^3$ is hydrogen, alkyl or aryl, R$^{12}$ is not hydrogen, and provided that when R$^1$ is phenyl, R$^3$ is benzyloxycarbonylamino, and R$^{12}$ is hydrogen, R$^2$ is not 2-methoxybenzyl, and R$^1$, R$^2$, R$^3$, R$^{12}$, R$^{13}$, R$^{14}$, R$^{15}$, R$^{16}$, R$^{21}$, R$^{22}$, R$^{23}$ and R$^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloaryl, haloalkoxy, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), or mixtures and combinations thereof.

In some embodiments, a compound is selected from the group consisting of (2R)-2-({[(1S)-1-(1,3-benzodioxol-5-yl)-3-hydroxypropyl]carbamoyl}amino)-N,N-bis(2-thienylmethyl)hexanamide; methyl(3S)-3-(1,3-benzodioxol-5-yl)-3-[({3-bis(2-thienylmethyl)amino]-3-oxopropyl}carbamoyl)amino]propanoate; (2S)-2-[(tert-butylcarbamoyl)amino]-N,N-bis(2-thienylmethyl) hexanamide; tert-butyl{(2S)-1-[bis(2-thienylmethyl) amino]-1-oxohexan-2-yl}carbamate; benzyl{(5S)-6-[bis(2-thienylmethyl)amino]-5-[(tert-butoxycarbonyl)(methyl) amino]-6-oxohexyl}carbamate; benzyl{(5S)-6-[bis(2-thienylmethyl)amino]-5-[(tert-butoxycarbonyl)amino]-6-oxohexyl}carbamate; benzyl{(5R)-6-[bis(2-thienylmethyl)amino]-5-[(tert-butoxycarbonyl)amino]-6-oxohexyl}carbamate; tert-butyl{(2R)-1-[bis(2-thienylmethyl)amino]-1-oxohexan-2-yl}carbamate; (2S)-2-acetamido-N,N-bis(2-thienylmethyl)hexanamide; benzyl {(5S)-5-acetamido-6-[bis(2-thienylmethyl)amino]-6-oxohexyl}carbamate; (2R)-2-acetamido-N,N-bis(2-thienylmethyl)hexanamide; benzyl{(5S)-5-(benzoylamino)-6-[bis(2-thienylmethyl)amino]-6-oxohexyl}carbamate; (2S)-2-[(phenylsulfonyl)amino]-N,N-bis(2-thienylmethyl) hexanamide; (2S)-2-[methyl(phenylsulfonyl)amino]-N,N-bis(2-thienylmethyl)hexanamide; 2-[(phenylsulfonyl) amino]-N,N-bis(2-thienylmethyl)acetamide; 2-[methyl (phenylsulfonyl)amino]-N,N-bis(2-thienylmethyl) acetamide; (2S)-2-[(methylsulfonyl)amino]-N,N-bis(2-thienylmethyl)hexanamide; (2S)-2-({[3-(4-methoxyphenoxy)propyl]sulfonyl}amino)-N,N-bis(2-thienylmethyl)hexanamide; benzyl{(5S)-6-[bis(2-thienylmethyl)amino]-6-oxo-5-[(2-thienylsulfonyl)amino] hexyl}carbamate; benzyl{(5S)-5-[(tert-butoxycarbonyl) amino]-6-[(3-methoxybenzyl)(2-thienyl-methyl)amino]-6-oxohexyl}carbamate; benzyl{(5S)-6-[bis(3-methoxybenzyl) amino]-5-[(tert-butoxycarbonyl)amino]-6-oxohexyl}carbamate; benzyl{(5R)-5-[(tert-butoxycarbonyl) amino]-6-[(3-methoxybenzyl) (2-thienyl-methyl)amino]-6-oxohexyl}carbamate; benzyl{(5R)-6-[bis(3-methoxybenzyl)amino]-5-[(tert-butoxycarbonyl)amino]-6-oxohexyl}carbamate; benzyl{(5S)-5-[(tert-butoxycarbonyl) amino]-6-oxo-6-{[2-(2-thienyl)ethyl](-2-thienylmethyl) amino}hexyl]carbamate; benzyl[(5R)-5-[(tert-butoxycarbonyl)amino]-6-oxo-6-{[2-(2-thienyl)ethyl](-2-thienylmethyl)amino}hexyl]carbamate; benzyl[(5S)-5-[(tert-butoxycarbonyl)amino]-6-(dibenzylamino)-6-oxohexyl]carbamate; benzyl{(5S)-5-[(tert-butoxycarbonyl) amino]-6-[(4-nitrobenzyl) (2-thienylmethyl)amino]-6-oxohexyl}carbamate; benzyl{(5R)-5-[(tert-butoxycarbonyl) amino]-6-[(4-nitrobenzyl) (2-thienylmethyl)amino]-6-oxohexyl}carbamate; tert-butyl[(2R)-1-[(4-aminobenzyl) (2-thienylmethyl)amino]-6-{[(benzyloxy)-carbonyl] amino}-1-oxohexan-2-yl]carbamate; tert-butyl[(2S)-1-[(4-aminobenzyl)(2-thienylmethyl)amino]-6-{[(benzyloxy)-carbonyl]amino}-1-oxohexan-2-yl]carbamate; benzyl{(5S)-5-[(tert-butoxycarbonyl) amino]-6-[methyl(2-thienylmethyl)amino]-6-oxohexyl}carbamate; benzyl{(5S)-5-[(tert-butoxycarbonyl)amino]-6-[butyl(2-thienylmethyl) amino]-6-oxohexyl}carbamate; benzyl{(5S)-6-[bis(4-methoxybenzyl)amino]-5-[(tert-butoxycarbonyl)amino]-6-oxohexyl}carbamate; benzyl{(5S)-5-[(tert-butoxycarbonyl) amino]-6-oxo-6-[(pyridin-4-ylmethyl) (-2-thienylmethyl) amino]hexyl}carbamate; benzyl{(5S)-5-[(tert-butoxycarbonyl) amino]-6-oxo-6-[(pyridin-3-ylmethyl)(-2-thienylmethyl)amino]hexyl}carbamate; benzyl{(5S)-6-[bis (pyridin-4-ylmethyl)amino]-5-[(tert-butoxycarbonyl) amino]-6-oxohexyl}carbamate; tert-butyl{(2S)-1-[bis(2-thienylmethyl)amino]-1-oxo-6-[(2-thienylsulfonyl)amino] hexan-2-yl}carbamate; tert-butyl{(2S)-6-acetamido-1-[bis (2-thienylmethyl)amino]-1-oxohexan-2-yl}carbamate; tert-butyl{(2S)-1-[bis(2-thienylmethyl) amino]-1-oxo-6-[(trifluoroacetyl)amino]hexan-2-yl}carbamate; tert-butyl {(2S)-1-[bis(2-thienylmethyl)amino]-6-[(methylsulfonyl) amino]-1-oxohexan-2-yl}carbamate; tert-butyl{(2S)-1-[bis (2-thienylmethyl)amino]-1-oxo-6-[(2-thienylcarbonyl) amino]hexan-2-yl}carbamate; tert-butyl{(2S)-1-[bis(2-thienylmethyl)amino]-1-oxo-6-[(phenylsulfonyl)amino]hexan-2-yl}carbamate; tert-butyl{(2S)-1-[bis(2-thienylmethyl) amino]-1-oxo-6-[(pyridin-3-ylcarbonyl)amino]hexan-2-yl}carbamate; tert-butyl{(2S)-1-[bis(2-thienylmethyl) amino]-1-oxo-6-[(2-thienylacetyl)amino]hexan-2-yl}carbamate; tert-butyl{(2S)-1-[bis(2-thienylmethyl)

amino]-6-hydroxy-1-oxohexan-2-yl}carbamate; tert-butyl [(2S)-1-[bis(2-thienylmethyl)amino]-1-oxo-6-{[(trifluoromethyl)sulfonyl]amino}hexan-2-yl]carbamate; tert-butyl{(2S)-6-[(benzylsulfonyl)amino]-1-[bis(2-thienylmethyl)amino]-1-oxohexan-2-yl}carbamate; tert-butyl {(2S)-6-[benzyl(trifluoroacetyl)amino]-1-[bis (2-thienylmethyl)amino]-1-oxohexan-2-yl}carbamate; tert-butyl[(1R)-2-[bis(2-thienylmethyl) amino]-1-(4-hydroxyphenyl)-2-oxoet-hyl]carbamate; methyl(4S)-5-[bis(2-thienylmethyl)amino]-4-[(tert-butoxycarbonyl)amino]-5-oxopentanoate; benzyl{(3S)-4-[bis(thiophen-2-ylmethyl)amino]-3-[(tert-butoxycarbonyl)amino]-4-oxobutyl}carbamate; benzyl {(4S)-5-[bis(2-thienylmethyl)amino]-4-[(tert-butoxycarbonyl)amino]-5-oxopentyl}carbamate; tert-butyl{2-[bis(2-thienylmethyl)amino]-2-oxoethyl}carbamate; tert-butyl{2-[bis(2-thienylmethyl)amino]-2-oxoethyl}methylcarbamate; N,N-bis(2-thienylmethyl)-6-[(2-thienylsulfonyl)amino] hexanamide; N-{6-[bis(2-thienylmethyl)amino]-6-oxohexyl}thiophene-2-carboxamide; N-{6-[bis(2-thienylmethyl)amino]-6-oxohexyl}-N-(2-thienylmethyl)thiophene-2-carboxamide; N-benzyl-N-{6-[bis(2-thienylmethyl)amino]-6-oxohexyl}thiophene-2-carboxamide; 6-[benzyl(2-thienylsulfonyl)amino]-N,N-bis(2-thienylmethyl) hexanamide; 6-[methyl(2-thienylsulfonyl)amino]-N,N-bis (2-thienylmethyl)hexanamide; 6-[(benzylsulfonyl)amino]-N,N-bis(2-thienylmethyl)hexanamide; 6-[(2-thienylacetyl)amino]-N,N-bis(2-thienylmethyl)hexanamide; N-{6-[bis(2-thienylmethyl)amino]-6-oxohexyl}-N-(3-methoxybenzyl) thiophene-2-carboxamide; 6-[(3-methoxybenzyl)(2-thienylsulfonyl)amino]-N,N-bis(2-thienylmethyl) hexanamide; 6-[(benzylsulfonyl)(3-methoxybenzyl)amino]-N,N-bis(2-thienylmethyl)hexanamide; benzyl{6-[bis(2-thienylmethyl)amino]-6-oxohexyl}carbamate; tert-butyl{6-[bis(thiophen-2-ylmethyl)amino]-6-oxohexyl}carbamate; tert-butyl[(2S)-1-[bis(2-thienylmethyl)amino]-3-(4-hydroxyphenyl)-1-oxopr-opan-2-yl]carbamate; Methyl(5S)-6-[bis(2-thienylmethyl)amino]-5-[(tert-butoxycarbonyl) amino]-6-oxohexanoate; (2S)-2-[acetyl(methyl)amino]-N, N-bis(2-thienylmethyl)hexanamide; benzyl{(5S)-5-[acetyl (methyl)amino]-6-[bis(2-thienylmethyl)amino]-6-oxohexyl}carbamate; (2S)-6-{[(benzyloxy)carbonyl] amino}-1-[bis(2-thienylmethyl)amino]-1-oxohexan-2-ylacetate; tert-butyl{(2S)-6-[benzyl(2-thienylsulfonyl) amino]-1-[bis(2-thienylmethyl)amino]-1-oxohexan-2-yl}carbamate; benzyl{(5S)-6-{bis[4-(trifluoromethoxy) benzyl]amino}-5-[(tert-butoxycarbonyl)amino]-6-oxohexyl}carbamate; benzyl[(5S)-5-[(tert-butoxycarbonyl)amino]-6-oxo-6-{(2-thienylmethyl)[2-(trifluoromethyl) benzyl]amino}hexyl]carbamate; benzyl[(5S)-5-[(tert-butoxycarbonyl)amino]-6-oxo-6-{(2-thienylmethyl) [2-(trifluoromethoxy) benzyl]amino}hexyl]carbamate; benzyl [(5S)-5-[(tert-butoxycarbonyl)amino]-6-{[2-(difluoromethoxy)benzyl]-(2-thienylmethyl)amino}-6-oxohexyl]carbamate; tert-butyl{6-[bis(4-methoxybenzyl) amino]-6-oxohexyl}carbamate; N-{6-[bis(4-methoxybenzyl)amino]-6-oxohexyl}-4-methoxybenzamide; N-{6-[bis(4-methoxybenzyl)amino]-6-oxohexyl}-4-methoxy-N-(4-methoxybenzyl-)benzamide; N-{6-[bis(2-thienylmethyl)amino]-6-oxohexyl}-N-methylthiophene-2-carboxamide; 6-[(3-methoxybenzyl)(2-thienylacetyl) amino]-N,N-bis(2-thienylmethyl)h-exanamide; tert-butyl{4-[bis(2-thienylmethyl)amino]-4-oxobutyl}carbamate; methyl(3S)-3-(1,3-benzodioxol-5-yl)-3-[({4-[bis(2-thienylmethyl)amino]-4-oxobutyl}carbamoyl) amino]propanoate; 6-{[(3-chloropropyl)sulfonyl]amino}-N, N-bis (4-methoxybenzyl)hexanamide; 6-(1,1-dioxido-1,2-thiazolidin-2-yl)-N,N-bis (4-methoxybenzyl)hexanamide; N,N-bis(4-methoxybenzyl)-6-({[2-(morpholin-4-yl)ethyl] sulfonyl}amino)hexanamide; 3-{[bis(2-thienylmethyl)carbamoyl]amino}-N,N-bis(2-thienylmethyl)propanamide; tert-butyl{3-[bis(2-thienylmethyl)amino]-3-oxopropyl}butylcarbamate; 3-{[bis(2-thienylmethyl)carbamoyl](butyl)amino}-N,N-bis (2-thienylmethyl)propanamide; 3-{butyl[(2-thienylmethyl)carbamoyl]amino}-N,N-bis (2-thienylmethyl)propanamide; 4-(1,1-dioxido-1,2-thiazolidin-2-yl)-N,N-bis (2-thienylmethyl)butanamide; N,N-bis(2-thienylmethyl)-3-{[(2-thienylmethyl)carbamoyl] amino}propanamide; benzyl{(5S)-6-[bis(2-thienylmethyl) amino]-5-hydroxy-6-oxohexyl}carbamate; benzyl{(5S)-6-[bis(2-thienylmethyl)amino]-5-cyano-6-oxohexyl}carbamate; benzyl{(5R)-5-azido-6-[bis(2-thienylmethyl)amino]-6-oxohexyl}carbamate; S-{(2R)-6-{[(benzyloxy)carbonyl]amino}-1-[bis(2-thienylmethyl) amino]-1-oxohexan-2-yl}ethanethioate; tert-butyl[(2S)-1-[bis(2-thienylmethyl)amino]-6-({[(4-bromobenzyl)oxy] carbonyl}amino)-1-oxohexan-2-yl]carbamate; 4-azidobenzyl{(5S)-6-[bis(2-thienylmethyl)amino]-5-[(tert-butoxycarbonyl)-amino]-6-oxohexyl}carbamate; benzyl {(5S)-6-[(4-bromobenzyl)(2-thienylmethyl)amino]-5-[(tert-butoxycarbonyl)amino]-6-oxohexyl}carbamate; tert-butyl [(2S)-1-[(4-azidobenzyl)(2-thienylmethyl)amino]-6-{[(benzyloxy)-carbonyl]amino}-1-oxohexan-2-yl]carbamate; tert-butyl{(2S)-1-[(4-bromobenzyl)(2-thienylmethyl) amino]-1-oxohexan-2-yl}carbamate; benzyl {(5S)-6-[bis(3-thienylmethyl)amino]-5-[(tert-butoxycarbonyl) amino]-6-oxohexyl}carbamate; benzyl {(5S)-5-[(tert-butoxycarbonyl)amino]-6-[(cyclopropylmethyl)(2-thienylmethyl)amino]-6-oxohexyl}carbamate, and mixtures or combinations thereof.

In some embodiments, a chemical compound is provided having the general formula (I), where $R^1$ is alkyl, aryl or aralkyl, $R^2$ is selected from the group consisting of aralkyl and alkyl, provided that when $R^1$ is alkyl, $R^2$ is aralkyl, $M^1$ is CO or $SO_2$, provided that when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, and when M' is CO and R' is 2-furyl, 4-pyridyl, or 3,5-dinitrophenyl, $R^2$ is not alkyl, benzyl or 2-(1H-indol-2-yl)ethyl, $M^2$ is absent or $CH_2$, $M^3$ and $M^4$ are absent, $M^5$ is $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $CONR^{22}R^{23}$, $COOR^{24}$, $O(CH_2CH_2O)_sR^{24}$ hydroxyalkyl and alkoxyalkyl, wherein s is an integer of 1 to 6, $M^6$ is $(CH_2)_q$ where q is an integer of 0 to 6, $R^3$ is selected from the group consisting of $NR^{15}COOR^{16}$, $NR^{15}COR^{16}$, $NR^{15}CONR^{13}R^{14}$, and $NR^{15}SO_2R^{16}$, and $R^{13}$, $R^{21}$ and $R^{22}$, when present, are independently selected from the group consisting of hydrogen and lower alkyl, and $R^{14}$, $R^{15}$, $R^{16}$, $R^{23}$ and $R^{24}$, each of which when present, is independently selected from the group consisting of hydrogen, alkyl, aryl, cycloalkyl, cycloalkylalkyl, heterocyclyl, heterocyclylalkyl and aralkyl, and $R^1$, $R^2$, $R^3$, $R^{12}$, $R^{14}$, $R^{15}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures or combinations thereof.

In some embodiments, a compound is selected from the group consisting of methyl(2S)-6-{[(benzyloxy)carbonyl]amino}-2-[benzyl(2-thienylsulfonyl)amino]hexanoate; methyl(2S)-6-{[(benzyloxy)carbonyl]amino]-2-[benzyl(phenylsulfonyl)amino]hexanoate; methyl(2S)-6-{[(benzyloxy)carbonyl]amino}-2-[(2-thienylcarbonyl-)(2-thienylmethyl)amino]hexanoate; methyl(2S)-6-{[(benzyloxy)carbonyl]amino}-2-[(2-thienylacetyl)(2-thienylmethyl)amino]hexanoate; methyl(2S)-2-[benzyl(isobutylsulfonyl)amino]-6-{[(benzyloxy) carbonyl]amino}hexanoate; benzyl{(5S)-5-[(tert-butoxycarbonyl)amino]-6-[(2-thienylmethyl)(2-thienylsulfonyl)amino]hexyl}carbamate; benzyl {(5S)-5-[(tert-butoxycarbonyl)amino]-6-[(2-thienylacetyl)(2-thienylmethyl)amino]hexyl}carbamate; benzyl{(5S)-5-[(tert-butoxycarbonyl)amino]-6-[(methylsulfonyl)(2-thienylmethyl)amino]hexyl}carbamate; benzyl{(5S)-5-[(tert-butoxycarbonyl)amino]-6-[(phenylsulfonyl)(2-thienylmethyl)amino]hexyl}carbamate; benzyl{(5S)-5-[(tert-butoxycarbonyl)amino]-6-[(2-thienylcarbonyl)(2-thienylmethyl)amino]hexyl}carbamate; N,N'-heptane-1,7-diylbis[N-(2-thienylmethyl)benzamide]; N,N'-heptane-1,7-diylbis[N-(2-thienylmethyl) thiophene-2-carboxamide]; benzyl[(5S)-5-[(tert-butoxycarbonyl)amino]-6-{[(4-methoxyphenyl)sulfonyl]-(2-thienylmethyl)amino}hexyl] carbamate; benzyl{(5S)-5-[(tert-butoxycarbonyl)amino]-6-[(4-methoxybenzoyl)(2-thienylmethyl)amino] hexyl}carbamate; N,N'-hexane-1,6-diylbis[N-(2-thienylmethyl) thiophene-2-carboxamide]; N,N'-hexane-1,6-diylbis[N-(3-methoxybenzyl) thiophene-2-carboxamide]; tert-butyl{5-[(4-methoxybenzyl)(2-thienylsulfonyl) amino]pentyl}carbamate; N,N'-pentane-1,5-diylbis[N-(3-methoxybenzyl)thiophene-2-sulfonamide]; N-(3-methoxybenzyl)-N-{5-[(2-thienylsulfonyl)amino]pentyl}thiophene-2-sulfonamide; tert-butyl{5-[(2-thienylcarbonyl)(2-thienylmethyl)amino]pentyl}carbamate; N-(3-methoxybenzyl)-N-{5-[(2-thienylcarbonyl)amino] pentyl}thiophene-2-carboxamide; N,N'-pentane-1,5-diylbis[N-(3-methoxybenzyl)thiophene-2-carboxamide]; and mixtures or combinations thereof.

In some embodiments, a chemical compound is selected having the general formula (I) where $R^1$ is aryl or aralkyl, $R^2$ is alkyl or aralkyl, $M^1$ is $CH_2$, $M^2$ is CO, $M^3$ is absent or is O or $CH_2$, $M^4$ is absent or is $CH_2$, $M^5$ is absent or is O or $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$ and $NR^{21}COOR^{24}$, $M^6$ is selected from the group consisting of $(CH_2)_q$, $(CH_2)_q$—CH=CH—$(CH_2)_r$, $(CH_2)_q$-arylene-$(CH_2)_r$ and $(CH_2CH_2O)_q$, wherein q and r are independently integers from 0 to 6, $R^3$ is $CONR^{13}R^{14}$, $R^{21}$ and $R^{22}$ each of which, when present is independently selected from the group of hydrogen and lower alkyl, $R^{13}$, $R^{14}$, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, and $R^1$, $R^2$, $R^{13}$, $R^{14}$, $R^{23}$ and $R^{24}$ when present may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO₂(alkyl), —NHSO₂(aryl), —NHSO₂(aralkyl), alkoxycarbonyl, alkoxycarbonylalkyl, —OCO(alkylamino), —OCO(dialkylamino), and mixtures or combinations thereof.

In some embodiments, a compound is selected from the group consisting of N,N,N',N'-tetrakis(2-thienylmethyl)pentanediamide; N-(3-methoxybenzyl)-N,N',N'-tris(2-thienylmethyl)pentanediamide; N,N,N'-tris(2-thienylmethyl)pentanediamide; N'-[2-(2-thienyl)ethyl]-N,N-bis(2-thienylmethyl)pentanediamide; N-[2-(2-thienyl)ethyl]-N,N', N'-tris (2-thienylmethyl)pentanediamide; N,N-bis(pyridin-4-ylmethyl)-N',N'-bis(2-thienylmethyl) pentanediamide; N,N-bis(pyridin-3-ylmethyl)-N',N'-bis(2-thienylmethyl) pentanediamide; N,N-bis(3-methoxybenzyl)-N',N'-bis(2-thienylmethyl)pentanediamide; N,N,N',N'-tetrakis (4-methoxybenzyl)pentanediamide; N,N,N',N'-tetrakis(2-thienylmethyl)hexanediamide; N,N,N',N'-tetrakis(4-methoxybenzyl)hexanediamide; N,N,N',N'-tetrakis(3-methoxybenzyl) hexanediamide; N,N,N',N'-tetrakis(2-thienylmethyl)heptanediamide; 2,2'-(1,3-phenylene)bis[N,N-bis (2-thienylmethyl)acetamide]; N,N,N',N'-tetrakis(4-methoxybenzyl)heptanediamide; N,N,N',N'-tetrakis(2-thienylmethyl)octanediamide; (3E)-N,N,N',N'-tetrakis(2-thienylmethyl) hex-3-enediamide; 2,2'-oxybis[N,N-bis(2-thienylmethyl)acetamide]; 3-oxo-1-(2-thienyl)-2-(2-thienylmethyl)-4,7,10-trioxa-2-azadodecan-12-yl bis(2-thienylmethyl)carbamate; N,N,N',N'-tetrakis(4-methoxybenzyl)succinamideethane-1,2-diylbis[bis(2-thienylmethyl)acetamide]; N,N,N',N'-tetrakis(4-methoxybenzyl)octanediamide; N,N,N',N'-tetrakis(2-thienylmethyl)pyridine-3,5-dicarboxamide; N,N,N',N'-tetrakis(2-thienylmethyl) pyridine-2,6-dicarboxamide; N,N,N',N'-tetrakis(2-thienylmethyl)pyridine-2,4-dicarboxamide; 2,2'-(1,4-phenylene)bis[N,N-bis(2-thienylmethyl)acetamide]; 8-{2-[bis(2-thienylmethyl)amino]-2-oxoethoxy}-N,N-bis(2-thienylmethyl)quinoline-2-carboxamide; N,N'-bis(4-methoxybenzyl)-N,N'-bis(2-thienylmethyl) hexanediamide; tert-butyl{(2S)-1,6-bis[bis(2-thienylmethyl)amino]-1,6-dioxohexan-2-yl}carbamate; and mixtures or combinations thereof.

In some embodiments a chemical compound is provided having the general formula (I), where $R^1$ is aryl or aralkyl, $R^2$ is alkyl or aralkyl, $M^1$ is $CH_2$, $M^2$ is $SO_2$ or CO, $M^3$ is absent or is $CH_2$, $M^4$ is absent or is $CH_2$, $M^5$ is absent or is $(CR^{11}R^{12})$, $R^{11}$, when present, is hydrogen, $R^{12}$, when present, is selected from the group consisting of hydrogen, alkyl, $NR^{21}CONR^{22}R^{23}$, $NR^{21}COR^{24}$, $NR^{21}SO_2R^{24}$ and $NR^{21}COOR^{24}$, $M^6$ is $(CH_2)_q$, or $NR^{34}(CH_2)_q$, wherein q is an integer from 0 to 6, $R^3$ is selected from the group consisting of $CONR^{13}R^{14}$, $SO_2NR^{13}R^{14}$, $NR^{15}COOR^{16}$, $NR^{15}COR^{16}$, $NR^{15}CONR^{13}R^{14}$, and $NR^{15}SO_2R^{16}$, $R^{15}$, $R^{16}$, $R^{21}$ and $R^{22}$, each of which when present, is independently selected from the group of hydrogen, lower alkyl, and aralkyl, $R^{13}$, $R^{14}$, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $R^{34}$, when present, is selected form the group consisting of alkyl, aralkyl, $COR^{35}$, and $SO_2R^{35}$, where $R^{35}$ when present, is selected form the group consisting of alkyl, aryl, and aralkyl, and $R^1$, $R^2$, $R^{13}$, $R^{14}$, $R^{15}$, $R^{16}$, $R^{23}$, $R^{24}$, $R^{34}$ and $R^{35}$, when present, may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO₂(alkyl), —NHSO₂(aryl), —NHSO₂(aralkyl), alkoxycarbonyl, alkoxycarbonylalkyl, —OCO(alkylamino), and —OCO(dialkylamino), with the proviso that when $M^2$ is CO, then $M^6$ is $NR^{34}(CH_2)_q$, wherein q is not 0.

In some embodiments, a compound is selected from the group consisting of N-{2-[bis(2-thienylmethyl)sulfamoyl]ethyl}-N-(2-thienylmethyl)thiophene-2-sulfonamide; N-{2-[bis(2-thienylmethyl)sulfamoyl]ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-{[bis(2-thienylmethyl)carbamoyl](butyl)amino}-N,N-bis(2-thienylmethyl)ethanesulfonamide; N-{3-[bis(2-thienylmethyl)sulfamoyl]propyl}-N-(2-thienylmethyl)thiophene-2-sulfonamide; 2-[(methylsulfonyl)(2-thienylmethyl)amino]-N,N-bis(2-thienylmethyl)ethanesulfonamide; 2-{[bis(2-thienylmethyl)carbamoyl]amino}-N,N-bis(2-thienylmethyl)ethanesulfonamide; N-{2-[bis(2-thienylmethyl)sulfamoyl]ethyl}thiophene-2-sulfonamide; N-{2-[bis(2-thienylmethyl)sulfamoyl]ethyl}-2-(2-thienyl)acetamide; N-{2-[bis(2-thienylmethyl)sulfamoyl]ethyl}thiophene-2-carboxamide; N,N-bis(2-thienylmethyl)-2-{[(2-thienylmethyl)carbamoyl]amino}ethanesulfonamide; 2-({2-[bis(2-thienylmethyl)sulfamoyl]ethyl}amino)-N,N-bis(2-thienylmethyl)acetamide; 3-[{2-[bis(2-thienylmethyl)amino]-2-oxoethyl}(butyl)amino]-N,N-bis(2-thienylmethyl)propanamide; 2-[{2-[bis(2-thienylmethyl)sulfamoyl]ethyl}(methyl)amino]-N,N-bis(2-thienylmethyl)acetamide; 2-[{2-[bis(2-thienylmethyl)sulfamoyl]ethyl}(butyl)amino]-N,N-bis(2-thienylmethyl)acetamide; 3-({2-[bis(2-thienylmethyl)sulfamoyl]ethyl}amino)-N,N-bis(2-thienylmethyl)propanamide; 3-({2-[bis(2-thienylmethyl)sulfamoyl]ethyl}amino)-N,N-bis(4-methoxybenzyl)propanamide; 3-({2-[bis(4-methoxybenzyl)sulfamoyl]ethyl}amino)-N,N-bis(2-thienylmethyl)propanamide; 3-[{2-[bis(2-thienylmethyl)sulfamoyl]ethyl}(methyl)amino]-N,N-bis(2-thienylmethyl)propanamide; 3-[{2-[bis(4-methoxybenzyl)sulfamoyl]ethyl}(methyl)amino]-N,N-bis(2-thienylmethyl) propanamide; (2S)-2-({2-[bis(2-thienylmethyl)sulfamoyl]ethyl}amino)-N,N-bis(2-thienylmethyl)hexanamide; (2S)-2-({2-[bis(4-methoxybenzyl)sulfamoyl]ethyl}amino)-N,N-bis(2-thienylmethyl)hexanamide; 2-(acetyl{2-[bis(2-thienylmethyl)sulfamoyl]ethyl}amino)-N,N-bis(2-thienylmethyl)acetamide; 2-(acetyl{2-[bis(4-methoxybenzyl)sulfamoyl]ethyl}amino)-N,N-bis(2-thienylmethyl)acetamide; and mixtures or combinations thereof.

In some embodiments, a compound is selected from the group consisting of tert-butyl[(2S)-1-{[bis(cyclopropylmethyl)carbamoyl]oxy}hexan-2-yl]carbamate; (2S)-2-[(tert-butoxycarbonyl)amino]hexyldiisobutylcarbamate; methyl (8S,12S)-12-(1,3-benzodioxol-5-yl)-8-butyl-4-isobutyl-2-methyl-5,10-dioxo-6-oxa-4,9,11-triazatetradecan-14-oate; benzyl{(5S)-6-[bis(cyclopropylmethyl)amino]-5-[(tert-butoxycarbonyl)amino-]-6-oxohexyl}carbamate; and mixtures or combinations thereof.

In accordance with certain embodiments, a pharmaceutical composition is provided comprising an above-described compound or a pharmaceutically acceptable salt thereof; and a pharmaceutically acceptable carrier.

In accordance with certain embodiments, a method of treating integrin-expressing cells is provided. The integrin may be one or more of α4β1, α5β1, α4β7, αvβ3 and αLβ2, for example. In some embodiments, the method of treating integrin-expressing cells comprises contacting at least one integrin-expressing cell in vitro with an agonist of said integrin, wherein said agonist is a compound having the general formula (I), where $R^1$ and $R^2$ are independently selected from the group consisting of alkyl, aryl, aralkyl, cycloalkyl, cycloalkylalkyl, haloalkyl, heterocylcyl and heterocyclylalkyl, one of $M^1$ and $M^2$ is CO or $SO_2$ and the other is $(CR^4R^5)_l$, provided that when $M^2$ is CO, $M^3$ is O, S, $NR^6$ or $(CR^7R^8)_m$, and provided that when $M^2$ is $SO_2$ or $(CR^4R^5)_l$, $M^3$ is $(CR^7R^8)_m$, $M^4$ is absent or is $(CR^9R^{10})_n$, $M^5$ is absent or is O or $(CR^{11}R^{12})$, $M^6$ is absent or is selected from the group consisting of $(CH_2)_q$, $(CH_2)_q$—CH=CH—$(CH_2)_r$, $(CH_2)_q$-arylene-$(CH_2)_r$, $(CH_2CH_2O)_q$, and $NR^{34}(CH_2)_q$, and $R^3$ is selected from the group consisting of hydrogen, OH, $OR^{16}$, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, alkyl, aryl, aralkyl, $SR^{16}$, heterocyclyl, hydroxyalkyl and guanadino, $R^{34}$, when present, is selected form the group consisting of alkyl, aralkyl, $COR^{35}$, and $SO_2R^3$, $R^{35}$, when present, is selected form the group consisting of alkyl, aryl, and aralkyl, and $R^{12}$, when present, is selected from the group consisting of hydrogen, alkyl, OH, $N_3$, CN, $NR^{21}CONR^{22}R^{23}$, $NR^{21}COR^{24}$, $NR^{21}COOR^{24}$, $NR^{21}SO_2R^{24}$, $CONR^{22}R^{23}$, $COOR^{24}$, $OCOR^{24}$, $OR^{24}$, $SCOR^{24}$, $SR^{24}$, azido, CN, and $O(CH_2CH_2O)_sR^{24}$, $R^4$, $R^5$, $R^6$, $R^7$, $R^8$, $R^9$, $R^{10}$, $R^{11}$, $R^{15}$, and $R^{21}$, each of which when present, is independently selected from the group consisting of hydrogen, lower alkyl and aralkyl, $R^{13}$, $R^{14}$, $R^{16}$, $R^{22}$, $R^{23}$ and $R^{24}$, each of which when present, is independently selected from the group consisting of alkyl, aryl, aralkyl, cycloalkyl, cycloalkylalkyl, haloalkyl, heterocyclyl, heterocyclylalkyl, alkoxycarbonyl, alkoxycarbonylalkyl, 1, m, n and p are independently integers from 0 to 1, q, r and s are independently integers from 0 to 6, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$, each of which when present, is independently either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxyl, alkoxy, haloalkoxy, azido, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(haloalkyl), —NHSO$_2$(alkyl), —NHSO$_2$(aryl), alkoxycarbonyl, alkoxycarbonylalkyl, —OCO(alkylamino), —OCO(dialkylamino), and mixtures or combinations thereof.

In accordance with certain embodiments, a method of enhancing binding of cells to an integrin-binding ligand is provided, wherein the method comprises treating integrin-expressing cells in vitro with an agonist of integrin described above, wherein said integrin is selected from the group consisting of α4β1, α5β1, α4β7, αvβ3 and αLβ2; and contacting the treated cells with an integrin-binding ligand.

In some embodiments, the agonist of integrin utilized in an above described method is a compound selected from the group consisting of methyl(3R)-3-(1,3-benzodioxol-5-yl)-3-[({(2R)-1-[bis(2-thienylmethyl)amino]-1-oxohexan-2-yl}carbamoyl)amino]propanoate; methyl(3S)-3-(1,3-benzodioxol-5-yl)-3-[({(2R)-6-{[(benzyloxy)carbonyl]amino}-1-[bis(thiophen-2-ylmethyl)amino]-1-oxohexan-2-yl}carbamoyl)amino]propanoate; methyl(3S)-3-(1,3-benzodioxol-5-yl)-3-[({(2R)-1-[bis(thiophen-2-yl-methyl)amino]-1-oxohexan-2-yl}carbamoyl)amino]propanoate; methyl(3R)-3-(1,3-benzodioxol-5-yl)-3-[({(2S)-1-[bis(2-thienylmethyl)amino]-1-oxohexan-2-yl}carbamoyl)amino]propanoate; methyl(3S)-3-(1,3-benzodioxol-5-yl)-3-[({2-[bis(2-thienylmethyl)amino]-2-oxoethyl}carbamoyl)amino]propanoate; methyl(3S)-3-(1,3-benzodioxol-5-yl)-3-[({2-[bis(2-thienylmethyl)amino]-2-oxoethyl}carbamoyl)amino]propanoate; methyl(3S)-3-(1,3-benzodioxol-5-yl)-3-{[{2-[bis(2-thienylmethyl)amino]-2-oxoethyl}(methyl)carbamoyl]amino}propanoate; methyl(3R)-3-(1,3- benzodioxol-5-yl)-3-{[{2-[bis(2-thienylmethyl)amino]-2-oxoethyl}(methyl)carbamoyl]amino}propanoate; methyl (3R)-3-(1,3-benzodioxol-5-yl)-3-[({2-[bis(2-thienylmethyl)amino]-2-oxoethyl}carbamoyl)amino]propanoate; methyl(2R)-[({(2S)-1-[bis (thiophen-2-ylmethyl)amino]-1-oxohexan-2-yl}carbamoyl)amino](phenyl)ethanoate; methyl 3-[({(2S)-1-[bis(2-thienylmethyl)amino]-1-oxohexan-2-yl}carbamoyl)amino]propanoate; (2S)-2-[(isopropylcarbamoyl)amino]-N,N-bis(2-thienylmethyl) hexanamide; (2S)-2-[(methylcarbamoyl)amino]-N,N-bis(2-thienylmethyl)hexanamide; (2S)-2-[(benzylcarbamoyl)amino]-N,N-bis(2-thienylmethyl)hexanamide; (2R)-2-[(benzylcarbamoyl)amino]-N,N-bis(2-thienylmethyl)hexanamide; benzyl{(5S)-5-[(benzylcarbamoyl)amino]-6-[bis(2-thienylmethyl)amino]-6-ox-ohexyl}carbamate; (2S)-2-{[(1,3-benzodioxol-5-ylmethyl)carbamoyl]amino}-N,N-bis(2-thienylme-thyl)hexanamide; benzyl[(5S)-6-[bis(2-thienylmethyl)amino]-6-oxo-5-{[(pyridin-3-ylmethyl)carbamoyl]amino}hexyl]carbamate; (2S)-2-{[(pyridin-3-ylmethyl)carbamoyl]amino}-N,N-bis(2-thienylmethyl) hexanamide; (2S)-2-({[(6-methoxypyridin-3-yl)methyl]carbamoyl}amino)-N,N-bis(-2-thienylmethyl) hexanamide; (2S)-2-({[3-(morpholin-4-yl)benzyl]carbamoyl}amino)-N,N-bis(2-thienylmethyl)hexanamide; (2S)-2-{[(4-hydroxybenzyl)carbamoyl]amino}-N,N-bis(2-thienylmethyl) hexanamide; (2S)-2-({[4-(dimethylamino)benzyl]carbamoyl}amino)-N,N-bis(2-thienylmethyl)hexanamide; benzyl[(5S)-6-[bis(2-thienylmethyl)amino]-5-({[3-(morpholin-4-yl)benzyl]carbamoyl}amino)-6-oxohexyl]carbamate; benzyl{(5S)-6-[bis(2-thienylmethyl)amino]-5-[({3-[(methylsulfonyl)amino]benzyl}carbamoyl) amino]-6-oxohexyl}carbamate; benzyl{(2S)-6-{[(benzyloxy)carbonyl]amino}-1-[bis(2-thienylmethyl)amino]-1-oxohexan-2-yl}carbamate; benzyl{(2S)-1-[bis(2-thienylmethyl)amino]-1-oxohexan-2-yl}carbamate; benzyl {(5S)-6-[bis(2-thienylmethyl) amino]-5-[(ethoxycarbonyl)amino]-6-oxohexyl}carbamate; benzyl[(5S)-6-[bis(2-thienylmethyl) amino]-5-(butyrylamino)-6-oxohexyl]carbamate; benzyl{(5S)-6-[bis(2-thienylmethyl)amino]-6-oxo-5-[(3-phenoxypropanoyl)amino]hexyl}carbamate; and mixtures or combinations thereof.

In other embodiments, an integrin agonist used in a method of enhancing binding of cells to an integrin-binding ligand is selected from the group consisting of compounds having the general formula (I) where $R^1$ is selected from the group consisting of alkyl, aryl, and aralkyl, $R^2$ is selected from the group consisting of alkyl, aryl, aralkyl, alkoxyalkyl and hydroxyalkyl, $M^1$ is $CH_2$, $M^2$ is $SO_2$; $M^3$, $M^4$, $M^5$, and $M^6$ independently are absent or are $CH_2$; $R^3$ is selected from the group consisting of alkyl, aryl, aralkyl, aryloxyalkyl, alkoxyalkyl, cycloalkyl and cycloalkylalkyl; $R^1$, $R^2$ and $R^3$ are independently either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxyl, alkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(haloalkyl), —NHSO$_2$(alkyl), —NHSO$_2$(aryl), alkoxycarbonyl, alkoxycarbonylalkyl, —OCO(alkylamino), —OCO(dialkylamino), and mixtures or combinations thereof.

In accordance with some further embodiments, an integrin agonist used in a method of enhancing binding of cells to an integrin-binding ligand is selected from the group consisting of N-bis(2-thienylmethyl)benzenesulfonamide; N,N-bis(2-thienylmethyl)acetamide; 1-phenyl-N,N-bis(2-thienylmethyl)methanesulfonamide; 2-methyl-N,N-bis(2-thienylmethyl) propane-1-sulfonamide; N-(3-methoxybenzyl)-N-(2-thienylmethyl)benzenesulfonamide; N-(3-methoxybenzyl)-N-(2-thienylmethyl)propane-2-sulfonamide; N-(3-methoxybenzyl)-2-methyl-(2-thienylmethyl)propane-1-sulfonamide; N-(4-hydroxybenzyl)-3-methoxy-N-(2-thienylmethyl) benzenesulfonamide; N-[2-(2-thienyl)ethyl]-N-(2-thienylmethyl)benzenesulfonamide; N,N-dibenzylbenzenesulfonamide; N-(pyridin-3-ylmethyl)-N-(2-thienylmethyl)benzenesulfonamide; N-butyl-N-(2-thienylmethyl)benzenesulfonamide; N-(3-hydroxypropyl)-N-(2-thienylmethyl) benzenesulfonamide; N-(2-methoxyethyl)-N-(2-thienylmethyl)benzenesulfonamide; N-(2-methoxyethyl)-N-(2-thienylmethyl)thiophene-2-sulfonamide; N,N-bis(3-methoxybenzyl)benzenesulfonamide; N,N-bis(4-methoxybenzyl)thiophene-2-sulfonamide; 2-chloro-N,N-bis(2-thienylmethyl)benzenesulfonamide; 3-chloro-N,N-bis(2-thienylmethyl)benzenesulfonamide; 4-chloro-N,N-bis(2-thienylmethyl) benzenesulfonamide; 3-methoxy-N,N-bis(2-thienylmethyl)benzenesulfonamide; 4-methoxy-N,N-bis(2-thienylmethyl)benzenesulfonamide; N,N-bis(pyridin-4-ylmethyl)benzenesulfonamide; N,N-bis(pyridin-3-ylmethyl)benzenesulfonamide; N-(2-furylmethyl)-N-(2-thienylmethyl)benzenesulfonamide; N,N-bis(2-furylmethyl) benzenesulfonamide; N,N-bis(3-methoxybenzyl)thiophene-2-sulfonamide; methyl 3-[bis(3-methoxybenzyl)sulfamoyl]thiophene-2-carboxylate; 2-(hydroxymethyl)-N,N-bis(3-methoxybenzyl)thiophene-3-sulfonamide; N,N-bis(4-methoxybenzyl)-3-methylbenzenesulfonamide; N-phenyl-N-(2-thienylmethyl)benzenesulfonamide; N-phenyl-N-(2-thienylmethyl)thiophene-2-sulfonamide; N-(3-methoxybenzyl)-phenylthiophene-2-sulfonamide; N-(3-methoxybenzyl)-N-phenylbenzenesulfonamide; 3-(4-methoxyphenoxy)-N,N-bis(2-thienylmethyl)propane-1-sulfonamide; 4-methyl-N,N-bis(2-thienylmethyl) benzenesulfonamide; 2-methyl-N,N-bis(2-thienylmethyl) benzenesulfonamide; 3-methyl-N,N-bis(2-thienylmethyl) benzenesulfonamide; and mixtures or combinations thereof.

In other embodiments a method of enhancing binding of cells to an integrin-binding ligand is provided, wherein said agonist of integrin is a compound selected from the group consisting of methyl(6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; tert-butyl[(2S)-1-{[bis(2-thienylmethyl)carbamoyl]oxy}hexan-2-yl]carbamate; (2S)-2-{[(1,3-benzodioxol-5-ylmethyl)carbamoyl]amino}hexyl-bis(2-thienylmethyl)carbamate; methyl(6S,10S)-6-butyl-3,8-dioxo-10-phenyl-1-(2-thienyl)-2-(2-thienylmethyl)-4-oxa-2,7,9-triazadodecan-12-oate; (2S)-2-[(benzylcarbamoyl)amino]hexyl bis(2-thienylmethyl) carbamate; (2S)-2-({[(1S)-1-(1,3-benzodioxol-5-yl)-3-hydroxypropyl]carbamoyl}amino)hexylbis(2-thienylmethyl)carbamate; methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; benzyl{(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; tert-butyl[(2R)-1-{[bis(2-thienylmethyl)carbamoyl]oxy}hexan-2-yl]carbamate; tert-butyl{[bis(2-thienylmethyl)carbamoyl](butyl)amino}acetate; benzyl{(5S)-6-{[bis(4-methoxybenzyl)

carbamoyl]oxy}-5-[(tert-butoxycarbonyl)amino]hexyl}carbamate; tert-butyl[(2S)-1-{[bis(4-methoxybenzyl)carbamoyl]oxy}hexan-2-yl]carbamate; methyl(6S,10S)-1-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl]carbamoyl}amino)hexyl-bis(4-methoxybenzyl)carbamate; (2S)-2-[(tert-butoxycarbonyl)amino]hexyldibenzylcarbamate; methyl(6S,10S)-10-(1,3-benzodioxol-5-yl)-2-benzyl-6-butyl-3,8-dioxo-1-phe-nyl-4-oxa-2,7,9-triazadodecan-12-oate; tert-butyl[(2S)-1-{[bis(4-methylbenzyl)carbamoyl]oxy}hexan-2-yl]carbamate-methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl(6S,10S)-1-(1,3-benzodioxol-5-yl)-6-butyl-2-(4-chlorobenzyl)-1-(4-chlorophenyl)-3,8-dioxo-4-oxa-2,7,9-triazadodecan-12-oate; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexylphenyl(2-thienylmethyl)carbamate; methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl)carbamoyl]oxy}hexan-2-yl]carbamate; methyl(6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tert-butoxycarbonyl)amino]-6-{[butyl(2-thienylmethyl)carbamoyl]oxy}hexyl]carbamate; (2S)-2-[(tert-butoxycarbonyl) amino]hexylbutyl(2-thienylmethyl)carbamate; methyl(3S,7S)-3-(1,3-benzodioxol-5-yl)-7-butyl-5,10-dioxo-11-(2-thienylmethyl)-9-oxa-4,6,11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-{[(4-bromobenzyl)carbamoyl]amino}hexyl bis(2-thienylmethyl)carbamate; (2S)-2-{[(4-azidobenzyl)carbamoyl]amino}hexyl bis(2-thienylmethyl)carbamate; tert-butyl[(2S)-1-{[bis(2-thienylmethyl)carbamoyl]thio}hexan-2-yl]carbamate; methyl(6S,10S)-10-(1,3-benzodioxol-5-yl)-6-butyl-3,8-dioxo-1-(2-thienyl)-2-(2-thienylmethyl)-4-thia-2,7,9-triazadodecan-12-oate; and mixtures or combinations thereof.

In some embodiments, a method of enhancing binding of cells to an integrin-binding ligand is provided, wherein an agonist of integrin is a compound selected from the group consisting of benzyl{(5R)-5-[(tert-butoxycarbonyl)amino]-6-[(3-methoxybenzyl)(2-thienylmethyl)amino]-6-oxohexyl}carbamate; benzyl{(5R)-6-[bis(3-methoxybenzyl)amino]-5-[(tert-butoxycarbonyl)amino]-6-oxohexyl}carbamate; benzyl{(5S)-6-[bis(4-methoxybenzyl)amino]-5-[(tert-butoxycarbonyl)amino]-6-oxohexyl}carbamate; benzyl{(5S)-5-[(tert-butoxycarbonyl)amino]-6-oxo-6-[(pyridin-3-ylmethyl)(-2-thienylmethyl)amino]hexyl}carbamate; benzyl{(5S)-5-[(tert-butoxycarbonyl)amino]-6-oxo-6-[(pyridin-4-ylmethyl)(2-thienylmethyl) amino]hexyl}carbamate; (2S)-2-[methyl(phenylsulfonyl)amino]-N,N-bis (2-thienylmethyl)hexanamide; (2S)-2-({[3-(4-methoxyphenoxy)propyl]sulfonyl}amino)-N,N-bis (2-thienylmet-hyl)hexanamide; benzyl{(5R)-6-[bis(2-thienylmethyl)amino]-5-[(tert-butoxycarbonyl) amino]-6-oxohexyl}carbamate; benzyl{(5S)-6-[bis(2-thienylmethyl)amino]-5-[(tert-butoxycarbonyl) amino]-6-oxohexyl}carbamate; benzyl{(5S)-6-[bis(2-thienylmethyl)amino]-6-oxo-5-[(2-thienylsulfonyl)amino]hexyl}carbamate; tert-butyl{(2S)-1-[bis(2-thienylmethyl)amino]-1-oxo-6-[(2-thienylsulfonyl)amino]hexan-2-yl}carbamate; 6-[methyl(2-thienylsulfonyl)amino]-N,N-bis(2-thienylmethyl)hexanamide; 6-[(2-thienylacetyl)amino]-N,N-bis(2-thienylmethyl)hexanamide; benzyl{(4S)-5-[bis(2-thienylmethyl)amino]-4-[(tert-butoxycarbonyl)amino]-5-oxopentyl}carbamate; benzyl{(5S)-5-[(tert-butoxycarbonyl)amino]-6-oxo-6-{(2-thienylmethyl)[2-(trifluoromethyl)benzyl]amino}hexyl]carbamate; benzyl[(5S)-5-[(tert-butoxycarbonyl)amino]-6-oxo-6-{(2-thienylmethyl) [2-(trifluoromethoxy)benzyl]amino}hexyl]carbamate; benzyl [(5S)-5-[(tert-butoxycarbonyl)amino]-6-{[2-(difluoromethoxy)benzyl]-(2-thienylmethyl)amino}-6-oxohexyl]carbamate; tert-butyl{6-[bis(4-methoxybenzyl)amino]-6-oxohexyl}carbamate; N-{6-[bis(4-methoxybenzyl) amino]-6-oxohexyl}-4-methoxy-N-(4-methoxybenzyl)benzamide; N-{6-[bis(2-thienylmethyl)amino]-6-oxohexyl}-N-methylthiophene-2-carboxamide; 6-[(3-methoxybenzyl) (2-thienylacetyl)amino]-N,N-bis(2-thienylmethyl)hexanamide; methyl(3S)-3-(1,3-benzodioxol-5-yl)-3-[({4-[bis(2-thienylmethyl)amino]-4-oxobutyl}carbamoyl)amino]propanoate; 6-{[(3-chloropropyl)sulfonyl]amino}-N,N-bis(4-methoxybenzyl) hexanamide; 3-{[bis(2-thienylmethyl)carbamoyl]amino}-N,N-bis(2-thienylmethyl)propanamide; 3-{butyl[(2-thienylmethyl)carbamoyl]amino}-N,N-bis(2-thienylmethyl) propanamide; benzyl{(5S)-6-[bis(2-thienylmethyl)amino]-5-cyano-6-oxohexyl}carbamate; benzyl{(5R)-5-azido-6-[bis(2-thienylmethyl)amino]-6-oxohexyl}carbamate; benzyl{(5S)-6-[bis(3-thienylmethyl)amino]-5-[(tert-butoxycarbon-yl)amino]-6-oxohexyl}carbamate; and mixtures or combinations thereof.

In other embodiments, a method of enhancing binding of cells to an integrin-binding ligand is provided, wherein an agonist of integrin is a compound selected from the group consisting of N-(3-methoxybenzyl)-N,N',N'-tris(2-thienylmethyl)pentanediamide; N-[2-(2-thienyl)ethyl]-N,N',N'-tris (2-thienylmethyl)pentanediamide; N,N-bis(3-methoxybenzyl)-N',N'-bis (2-thienylmethyl)pentanediamide; N,N-bis(pyridin-4-ylmethyl)-N',N'-bis (2-thienylmethyl)pentanediamide; N,N,N',N'-tetrakis(2-thienylmethyl) hexanediamide; N,N,N',N'-tetrakis(3-methoxybenzyl) hexanediamide; N,N,N',N'-tetrakis(4-methoxybenzyl) hexanediamide; (3E)-N,N,N',N'-tetrakis(2-thienylmethyl) hex-3-enediamide; N,N,N',N'-tetrakis(2-thienylmethyl)pentanediamide; N,N,N',N'-tetrakis(4-methoxybenzyl) pentanediamide; 2,2'-oxybis[N,N-bis(2-thienylmethyl) acetamide]; N,N,N',N'-tetrakis (2-thienylmethyl) octanediamide; N,N,N',N'-tetrakis(2-thienylmethyl) heptanediamide; 3-oxo-1-(2-thienyl)-2-(2-thienylmethyl)-4,7,10-trioxa-2-azadodecan-12-yl bis(2-thienylmethyl)carbamate; 2,2'-(1,3-phenylene)bis[N,N-bis(2-thienylmethyl)acetamide]; N,N,N',N'-tetrakis(4-methoxybenzyl)heptanediamide; N,N,N',N'-tetrakis(4-methoxybenzyl)succinamideethane-1,2-diylbis[bis(2-thienylmethyl)carbamate]; N,N,N',N'-tetrakis(4-methoxybenzyl)octanediamide; N,N,N',N'-tetrakis(2-thienylmethyl) pyridine-3,5-dicarboxamide; N,N,N',N'-tetrakis(2-thienylmethyl)pyridine-2,6-dicarboxamide; N,N,N',N'-tetrakis(2-thienylmethyl)pyridine-2,4-dicarboxamide; 2,2'-(1,4-phenylene)bis [N,N-bis(2-thienylmethyl)acetamide]; N,N'-bis(4-methoxybenzyl)-N,N'-bis (2-thienylmethyl)hexanediamide; and mixtures or combinations thereof.

In another embodiment, a method of enhanced binding of integrin-expressing cells to an integrin-binding ligand utilizes an integrin agonist compound selected from the group consisting of methyl(2S)-6-{[(benzyloxy)carbonyl]amino}-2-[benzyl(phenylsulfonyl)amino]hexanoate; methyl(2S)-6-{[(benzyloxy)carbonyl]amino}-2-[benzyl(2-thienylsulfonyl)amino]hexanoate; methyl(2S)-6-{[(benzyloxy)carbonyl]amino}-2-[(2-thienylacetyl)(2-thienylmethyl)amino]hexanoate; methyl(2S)-6-{[(benzyloxy)carbonyl]amino}-2-[(2-thienylcarbonyl)(2-thienylmethyl)amino]hexanoate; benzyl{(5S)-5-[(tert-butoxycarbonyl)amino]-6-[(2-thienylmethyl) (2-thienylsulfonyl)amino] hexyl}carbamate; benzyl{(5S)-5-[(tert-butoxycarbonyl) amino]-6-[(phenylsulfonyl)(2-thienylmethyl) amino] hexyl}carbamate; benzyl{(5S)-5-[(tert-butoxycarbonyl) amino]-6-[(2-thienylacetyl) (2-thienylmethyl)amino] hexyl}carbamate; benzyl{(5S)-5-[(tert-butoxycarbonyl) amino]-6-[(methylsulfonyl)(2-thienylmethyl)amino] hexyl}carbamate; benzyl{(5S)-5-[(tert-butoxycarbonyl) amino]-6-[(2-thienylcarbonyl)(2-thienylmethyl) amino] hexyl}carbamate; benzyl[(5S)-5-[(tert-butoxycarbonyl) amino]-6-{[(4-methoxyphenyl)sulfonyl]-(2-thienylmethyl) amino}hexyl]carbamate; benzyl{(5S)-5-[(tert-butoxycarbonyl)amino]-6-[(4-methoxybenzoyl)(2-thienylmethyl)amino]hexyl}carbamate; N,N'-heptane-1,7-diylbis[N-(2-thienylmethyl)thiophene-2-carboxamide]; N,N'-heptane-1,7-diylbis[N-(2-thienylmethyl)benzamide; N,N'-hexane-1,6-diylbis [N-(2-thienylmethyl)thiophene-2-carboxamide]; N,N'-hexane-1,6-diylbis[N-(3-methoxybenzyl) thiophene-2-carboxamide]; tert-butyl{5-[(4-methoxybenzyl)(2-thienylsulfonyl) amino]pentyl}carbamate; N-(3-methoxybenzyl)-N-{5-[(2-thienylsulfonyl)amino] pentyl}thiophene-2-sulfonamide; tert-butyl{(2S)-1,6-bis [bis(2-thienylmethyl)amino]-1,6-dioxohexan-2-yl}carbamate; tert-butyl{5-[(2-thienylcarbonyl)(2-thienylmethyl)amino]pentyl}carbamate; N-(3-methoxybenzyl)-N-{5-[(2-thienylcarbonyl)amino] pentyl}thiophene-2-carboxamide; N,N'-pentane-1,5-diylbis [N-(3-methoxybenzyl)thiophene-2-carboxamide]; and mixtures or combinations thereof.

In a further embodiment, a method of enhanced binding of integrin-expressing cells to an integrin-binding ligand utilizes an integrin agonist compound selected from the group consisting of N-{2-[bis(2-thienylmethyl)sulfamoyl]ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-[(methylsulfonyl)(2-thienylmethyl)amino]-N,N-bis(2-thienylmethyl)ethanesulfonamide; 2-{[bis(2-thienylmethyl)carbamoyl]amino}-N,N-bis(2-thienylmethyl)ethanesulfonamide; N-{2-[bis(2-thienylmethyl)sulfamoyl]ethyl}thiophene-2-sulfonamide; N-{2-[bis(2-thienylmethyl) sulfamoyl]ethyl}-2-(2-thienyl) acetamide; N-{2-[bis(2-thienylmethyl)sulfamoyl] ethyl}thiophene-2-carboxamide; N,N-bis(2-thienylmethyl)-2-{[(2-thienylmethyl)carbamoyl] amino}ethanesulfonamide; 2-({2-[bis(2-thienylmethyl) sulfamoyl]ethyl}amino)-N,N-bis(2-thienylmethyl) acetamide; 3-[{2-[bis(2-thienylmethyl)amino]-2-oxoethyl} (butyl)amino]-N,N-bis(2-thienylmethyl) propanamide; 2-[{2-[bis(2-thienylmethyl)sulfamoyl]ethyl}(methyl) amino]-N,N-bis(2-thienylmethyl) acetamide; 3-({2-[bis(2-thienylmethyl)sulfamoyl]ethyl}amino)-N,N-bis(2-thienylmethyl) propanamide; 3-({2-[bis(2-thienylmethyl) sulfamoyl]ethyl}amino)-N,N-bis(4-methoxybenzyl) propanamide; 2-(acetyl{2-[bis(2-thienylmethyl)sulfamoyl] ethyl}amino)-N,N-bis(2-thienylmethyl) acetamide; 2-(acetyl{2-[bis(4-methoxybenzyl)sulfamoyl] ethyl}amino)-N,N-bis(2-thienylmethyl) acetamide; and mixtures or combinations thereof.

In some embodiments, a method of enhancing binding of cells to an integrin-binding ligand is provided, wherein said agonist of integrin is a compound selected from the group consisting of tert-butyl[(2S)-1-{[bis(cyclopropylmethyl)carbamoyl]oxy}hexan-2-yl]carbamate; (2S)-[(tert-butoxycarbonyl)amino]hexyldiisobutylcarbamate; methyl(8S,12S)-12-(1,3-benzodioxol-5-yl)butyl-4-isobutyl-2-methyl-5,10-dioxo-6-oxa-4,9,11-triazatetradecan-14-oate; benzyl{(5S)-6-[bis(cyclopropylmethyl)amino]-5-[(tert-butoxycarbonyl) amino-]-6-oxohexyl}arbamate; and mixtures or combinations thereof.

Vaccines

Background

During the priming and effector phases of the immune response, antigens are taken up by cells termed antigen presenting cells (APCs). APCs then present this antigen in the context of major histocompatibility complex (MHC) molecules on their cell surface, to stimulate lymphocytes to become activated, proliferate, and differentiate into effector cells that can eventually protect the host. CD4$^+$ T-helper 1 cells (Th1 cells) directly interact with APCs and produce cytokines, which drive lymphocyte proliferation and the eventual development of memory T cells, and effector cytotoxic T Lymphocytes (CTLs). CD4$^+$ T-helper 2 cells (Th2 cells) directly interact with antigen presenting cells and drive B-cell activation and proliferation, eventually resulting in the production of a humoral, antibody-dependent immune response. Communication between a variety of cell types must occur through direct cell contact for a productive immune response to follow antigenic challenge. Direct cell-cell contacts are mediated by the integrin family of cell adhesion molecules.

Integrin cell adhesion molecules are cell surface glycoproteins comprised on non-covalently associated α and β heterodimers. Eighteen different α-chains combine with 8 β-chains to form 24 different αβ pairs. On leukocytes, integrins are intimately involved in the adhesion cascade, which governs leukocyte trafficking to sites of inflammation or injury. Integrins are also key components in the generation of an adaptive immune response, which is easily observed during the process of vaccination.

Integrins are also essential in the priming phase of the immune response, as this phase requires the direct interaction between lymphocytes and APCs. The integrins α4β1 and αLβ2 both have been shown to be important in lymphocyte conjugation with APCs and have been shown to be able to provide costimulatory signals that result in lymphocyte activation, proliferation, differentiation and even positive selection. Fibronectin promotes proliferation of naive and memory T cells by signaling through both the VLA-4 and VLA-5 integrin molecules. Activating these integrins to promote efficient conjugation between lymphocytes and APCs would augment the immune response by enhancing integrin costimulatory effects. For a number of diseases, current vaccination strategies are inadequate to generate long term protective immunity. This is especially true in the case of vaccines directed towards tumor-associated antigens in cancer. We have now discovered that small molecule compounds that promote integrin:ligand interactions, such as those embodied in United States Published Patent Application No. 20130236434A1 and Vanderslice, P., Biediger, R. J., Woodside, D. G., Brown, W. S., Khounlo, S., Warier, N. D., Gundlach, C. W. t., Caivano, A. R., Bornmann, W. G., Maxwell, D. S., et al. "Small molecule agonist of very late antigen-4 (VLA-4) integrin induces progenitor cell adhesion," *J Biol Chem* 288, 19414-19428 2013 (Vanderslice et al. 2013), effectively function as: (1) targeted adjuvant to safely increase the priming responses with current vaccination approaches, and (2) increase effector functions of both humoral and innate immune responses. Biediger et al and Vanderslice et al failed to recognize the use of such integrin agonists as immunomodulators which could be used to drive many aspects of the immune response independent of their ability to cause increased retention within target tissues. In examining these integrin agonists further, we discovered that their use could be expanded to multiple aspects of the immune response, which are described below.

Vaccines Embodiments

A pharmaceutical preparation of a vaccine comprising an antigen and effective amount of one or a plurality of enhancing compounds, where the associated enhancing compounds are capable of enhancing integrin-mediated binding of integrins of a cell to their respective ligand, wherein the integrins include $\alpha 4\beta 1$, $\alpha 4\beta 7$, $\alpha 5\beta 1$, and/or $\alpha L\beta 2$, wherein the ligands include VCAM-1, fibronectin, MAdCAM-1, ICAM-1, and/or ICAM-2, wherein the antigen is a purified protein, peptide, cell, or cell lysate.

A pharmaceutical preparation of an anticancer vaccine comprising an antigen and effective amount of one or a plurality of enhancing compounds, where the associated enhancing compounds are capable of enhancing integrin-mediated binding of integrins of a cell to their respective ligand, wherein the integrins include $\alpha 4\beta 1$, $\alpha 4\beta 7$, $\alpha 5\beta 1$, and/or $\alpha L\beta 2$, wherein the ligands include VCAM-1, fibronectin, MAdCAM-1, ICAM-1, and/or ICAM-2, wherein the antigen is a purified protein, peptide, tumor cell, or tumor lysate.

A pharmaceutical preparation of an anti-cancer vaccine comprising an antigen, adjuvant and effective amount of one or a plurality of enhancing compounds, where the associated enhancing compounds are capable of enhancing integrin-mediated binding of integrins of a cell to their respective ligand, wherein the integrins include $\alpha 4\beta 1$, $\alpha 4\beta 7$, $\alpha 5\beta 1$, and/or $\alpha L\beta 2$, wherein the ligands include VCAM-1, fibronectin, MAdCAM-1, ICAM-1, ICAM-2, wherein the antigen is a purified protein, peptide, tumor cell, or tumor lysate, wherein the adjuvant is non-specific or specific substance capable of eliciting an immune response in response to an antigen. Examples of non-specific adjuvants include BCG, complete freund's adjuvant, alum, or noscapine. Specific adjuvants include without limitations G-CSF, FGF, Toll-like receptor agonists, immune checkpoint inhibitors (CTL-4, PD-1, PDL-1, IDO-1). The integrin enhancing compounds are considered specific adjuvants.

Method to treat a patient with an effective amount of one or a plurality of enhancing compounds, wherein the associated enhancing compounds are capable of enhancing integrin-mediated binding of integrins of a cell to their respective ligand, wherein the integrins include $\alpha 4\beta 1$, $\alpha 4\beta 7$, $\alpha 5\beta 1$, and/or $\alpha L\beta 2$, wherein the ligands include VCAM-1, fibronectin, MAdCAM-1, ICAM-1, and/or ICAM-2, in combination with a therapeutically ineffective dose of immune checkpoint inhibitor, cytotoxic chemotherapy, cancer vaccine, wherein the patient has been diagnosed with cancer.

Method to treat a patient with an effective amount of one or a plurality of enhancing compounds, wherein the associated enhancing compounds are capable of enhancing integrin-mediated binding of integrins of a cell to their respective ligand, wherein the integrins include $\alpha 4\beta 1$, $\alpha 4\beta 7$, $\alpha 5\beta 1$, and/or $\alpha L\beta 2$, wherein the ligands include VCAM-1, fibronectin, MAdCAM-1, ICAM-1, and/or ICAM-2, in combination with a therapeutically ineffective dose of immune checkpoint inhibitor, cytotoxic chemotherapy, cancer vaccine, wherein the patient has been diagnosed with solid tumors in the lung, prostate, breast, colon, skin, brain, or pancreas, wherein the enhancing compound is systemic administered by enteral or parenteral route of administration.

Method to treat a patient with an effective amount of one or a plurality of enhancing compounds, where the associated enhancing compounds are capable of enhancing integrin-mediated binding of integrins of a cell to their respective ligand, wherein the integrins include $\alpha 4\beta 1$, $\alpha 4\beta 7$, $\alpha 5\beta 1$, and/or $\alpha L\beta 2$, wherein the ligands include VCAM-1, fibronectin, MAdCAM-1, ICAM-1, ICAM-2, and/or vitronectin, in combination with a therapeutically ineffective dose of immune checkpoint inhibitor, cytotoxic chemotherapy, wherein the patient has been diagnosed with hematologic cancers, wherein the integrin mimetic is systemic administered by enteral or parenteral route of administration.

Adoptive Cell Therapy

Background

Figure 2:
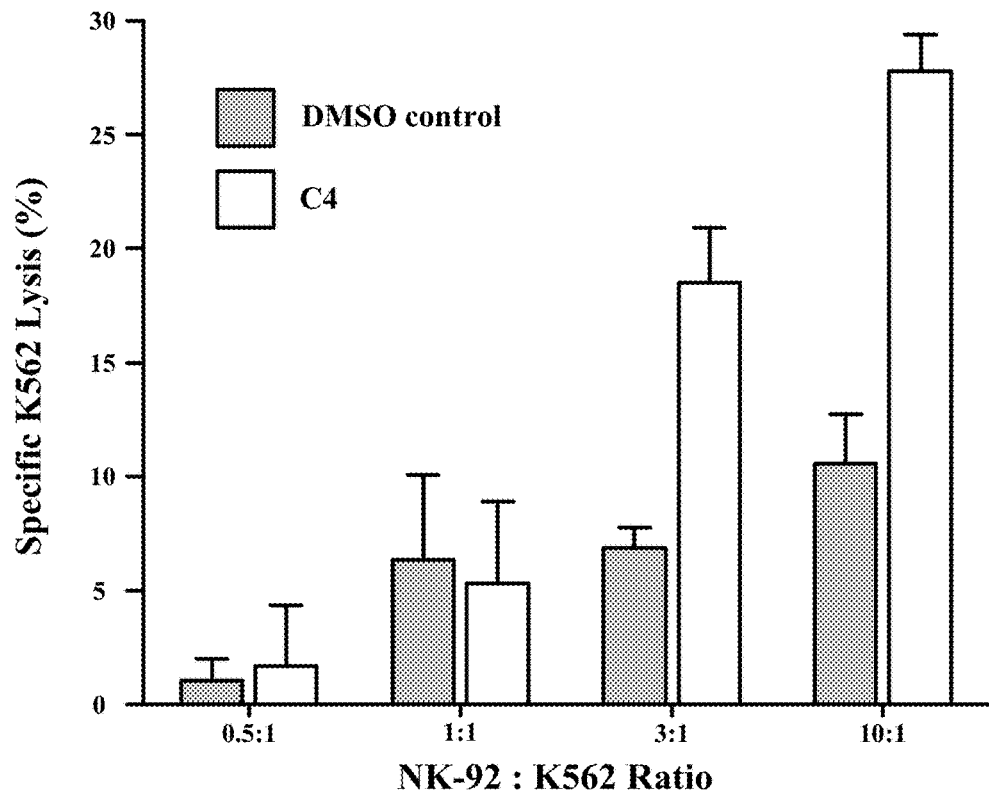
FIG. 2 depicts the natural killer cell line NK-92, which was used at different effector to target ratios in the presence or absence of C4 (100 μM). Specific lysis of K562 cells is shown. All data are from triplicate determinations, and graphed as the mean±SD.

One of the outcomes of a productive immune response is the killing of specific target cells by effector lymphocytes. Antigen specific CTLs, Natural Killer (NK) cells, invariant NK T (iNKT) cells, and various engineered derivatives of these cells, all of which are under clinical investigation as cancer therapies, bind to and directly kill their intended cellular targets. Conjugate formation between CTLs or NK cells and their targets requires cell adhesion mediated by the integrin family of cell adhesion molecules, in particular the integrins $\alpha 4\beta 1$ and $\alpha L\beta 2$. Cross-linking of $\alpha 4\beta 1$ and $\alpha 5\beta 1$ fibronectin receptors enhances natural killer cell cytotoxic activity. By enhancing these adhesive and costimulatory interactions, activators of integrin adhesion will promote this cytolytic activity and increase the in vivo killing in both vaccine strategies, and in adoptive cell therapies. This is exemplified in FIGS. 1&2. The pharmaceutical compositions comprising an enhancing compound alone in a vaccine based strategy, or in a combination with effector cells could be particularly useful in patients with refractory cancers.

Adoptive Cell Therapy Embodiments

A pharmaceutical preparation comprising NK cells, activated NK cells, engineered NK cells, or NK cell lines (and derivatives thereof) treated with an effective amount of one or a number of compounds capable of activating integrin mediated interactions with their cognate ligands.

A method to treat a patient with a pharmaceutical preparation comprising NK cells, activated NK cells, engineered NK cells, or NK cell lines (and derivatives thereof) delivered in combination with (either prior to, during, or after) an effective amount of one or a number of compounds capable of activating integrin mediated interactions with their cognate ligands.

A method to treat a patient with a pharmaceutical preparation comprising a therapeutically ineffective amount of NK cells, activated NK cells, engineered NK cells, or NK cell lines (and derivatives thereof) delivered in combination with (either prior to, during, or after) an effective amount of one or a number of compounds capable of activating integrin mediated interactions with their cognate ligands.

A pharmaceutical preparation comprising invariant natural killer T (iNKT) cells, activated iNKT cells, engineered iNKT cells, or iNKT cell lines (and derivatives thereof) treated with an effective amount of one or a number of compounds capable of activating integrin mediated interactions with their cognate ligands.

A method to treat a patient with a pharmaceutical preparation comprising iNKT cells, activated iNKT cells, engineered iNKT cells, or iNKT cell lines (and derivatives thereof) delivered in combination with (either prior to, during, or after) an effective amount one or a number of compounds capable of activating integrin mediated interactions with their cognate ligands.

A method to treat a patient with a pharmaceutical preparation comprising a therapeutically ineffective amount of iNKT cells, activated iNKT cells, engineered iNKT cells, or iNKT cell lines (and derivatives thereof) delivered in combination with (either prior to, during, or after) an effective amount one or a number of compounds capable of activating integrin mediated interactions with their cognate ligands.

A pharmaceutical preparation comprising γδT cells, activated iNKT cells, engineered γδT cells, or γδT cell lines (and derivatives thereof) treated with an effective amount of one or a number of compounds capable of activating integrin mediated interactions with their cognate ligands.

A method to treat a patient with a pharmaceutical preparation comprising γδT cells, activated iNKT cells, engineered γδT cells, or γδT cell lines (and derivatives thereof) delivered in combination with (either prior to, during, or after) an effective amount one or a number of compounds capable of activating integrin mediated interactions with their cognate ligands.

A method to treat a patient with a pharmaceutical preparation comprising γδT cells, activated iNKT cells, engineered γδT cells, or gδT cell lines (and derivatives thereof) delivered in combination with (either prior to, during, or after) an effective amount one or a number of compounds capable of activating integrin mediated interactions with their cognate ligands.

A pharmaceutical preparation comprising cytotoxic T lymphocytes (CTLs) (including, but not limited to, tumor infiltrating lymphocytes, lymphocytes expanded in an antigen specific manner, lymphocytes engineered to express chimeric antigen receptors) treated with an effective amount of one or a number of compounds capable of activating integrin mediated interactions with their cognate ligands for the purpose of enhancing CTL tumoricidal activity.

A method to treat a patient with a pharmaceutical preparation comprising cytotoxic T lymphocytes (CTLs) (including, but not limited to, tumor infiltrating lymphocytes, lymphocytes expanded in an antigen specific manner, lymphocytes engineered to express chimeric antigen receptors) delivered in combination with (either prior to, during, or after) an effective amount of one or a number of compounds capable of activating integrin mediated interactions with their cognate ligands for the purpose of enhancing CTL tumoricidal activity.

A method to treat a patient with a pharmaceutical preparation comprising a therapeutically ineffective amount of cytotoxic T lymphocytes (CTLs) (including, but not limited to, tumor infiltrating lymphocytes, lymphocytes expanded in an antigen specific manner, lymphocytes engineered to express chimeric antigen receptors) delivered in combination with (either prior to, during, or after) an effective amount of one or a number of compounds capable of activating integrin mediated interactions with their cognate ligands for the purpose of enhancing CTL tumoricidal activity.

Antibody Dependent Cellular Cytotoxicity

Background

Antibody dependent cellular cytotoxicity (ADCC) is a mechanism whereby antibodies bind a cell surface antigen, opsonizing the cell for engulfment (phagocytosis) and/or destruction by effector cells of the immune system such as neutrophils, macrophage, and NK cells that express activating receptors for the Fc components of antibodies. The in vivo mechanism of action of humanized monoclonal antibodies (mAbs) trastuzumab (Herceptin®), rituximab (Rituxan®), ipilimumab (Yervoy@) and others involve ADCC. The β2 integrin family (including integrin CD11a/CD18 (also called αLβ2 or LFA-1) are important mediators of the direct binding between effectors and antibody-opsonized target cells during ADCC. Enhancing ADCC with small molecule integrin activators would promote ADCC and serve as an adjunct therapy with any therapeutic antibody with an Fc component.

Pharmaceutical compositions comprising an enhancing compound in combination with a therapeutic antibody is useful in patients to treat minimal residual disease, and those refractory to such therapeutic antibodies.

ADCC Embodiments

A method to treat a patient with a therapeutic antibody, wherein the antibody contains a Fc region, wherein the antibody is, without limitation, trastuzumab, cetuximab, ipilimumab, nivolumab, rituximab, alemtuzumab, atumumab, or tositumomab, and an effective amount of one or a number of compounds capable of activating integrin mediated interactions with their cognate ligands.

A method to treat a patient with therapeutically ineffective amount of therapeutic antibody, wherein the antibody contains a Fc region, wherein the antibody is, without limitation, trastuzumab, cetuximab, ipilimumab, nivolumab rituximab, alemtuzumab, atumumab, or tositumomab, and an effective amount of one or a number of compounds capable of activating integrin mediated interactions with their cognate ligands.

A pharmaceutical composition comprising a therapeutically ineffective amount of therapeutic antibody, wherein the antibody contains a Fc fragment and an effective amount of one or a number of compounds capable of activating integrin mediated interactions with their cognate ligands.

TABLE I

Compound Designation, Names, and Structures

| Compound | |
|---|---|
| C1 | (6S,10S)-methyl 10-1,3-benzodioxol-5-yl)-6-butyl-3,8-dioxo-1-(2-thienyl)-2-(2-thienylmethyl)-4-oxa-2,7,9-triazadodecan-12-oate |
| C2 | $N^1,N^1,N^6,N^6$-tetrakis(4-methoxybenzyl)adipamide |
| C3 | $N^1,N^1,N^6,N^6$-tetrakis(3-methoxybenzyl)adipamide |
| C4 | (ethane-1,2-diylbis(oxy))bis(ethane-2,1-diyl) bis(bis(thiophen-2-ylmethyl)carbamate) |

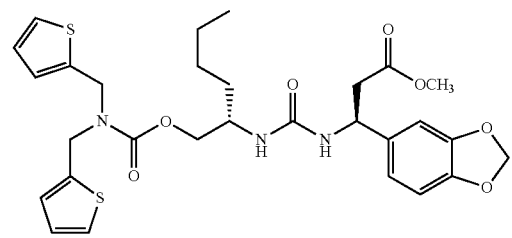

C1

TABLE I-continued

Compound Designation, Names, and Structures

Compound

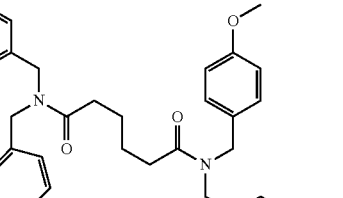

C2

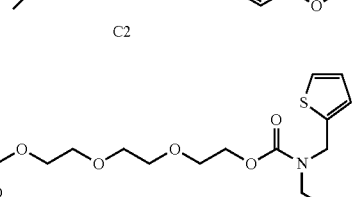

C3

C4

Antibody dependent cellular cytotoxicity (ADCC) is mediated by natural killer (NK) cells, monocytes and macrophage, and other effector cells that express receptors (like CD16) that can bind to antibodies bound to target cells.

Cell adhesion between effector cells like NK cells and their target cells is mediated by integrin cell adhesion molecules. This adhesion is essential for both cytolytic killing activity and ADCC. Compounds such as C4 and other compounds of Formula (I), target integrins α4β1 and αLβ2, which are essential in cytolytic T cell and NK cell dependent killing of tumor targets, and are required for ADCC in vivo.

C4 and/or other compounds of Formula (I) are positive allosteric modulators of integrin cell adhesion molecules, inducing integrins α4β1 and αLβ2 (among others), to interact with their cognate ligands (Table II).

TABLE II

Activity ($EC_{50}$, μM) of C4 in Enhancing
Adhesion Mediated by Different Classes of Integrins

| Compound | α4β1 (VLA-4) | αLβ2 (LFA-1) |
|---|---|---|
| C1 | 32 | 26 |
| C2 | 11 | 11 |
| C3 | 11 | 7 |
| C4 | 14 | 11 |

Figure 3A:
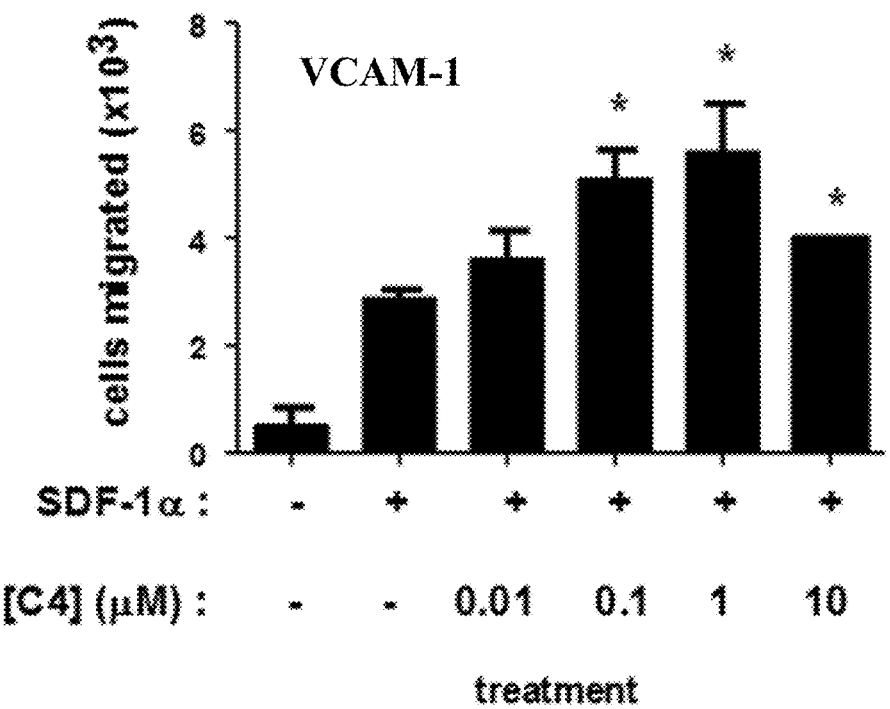
FIGS. 3A&B depicts activity of C4 in enhancing SDF-1a mediated migration of Jurkat T cell, an exemplary activated T-cell, across membranes coated with either VCAM-1 or ICAM-1 (*p<0.05).
Figure 3B:
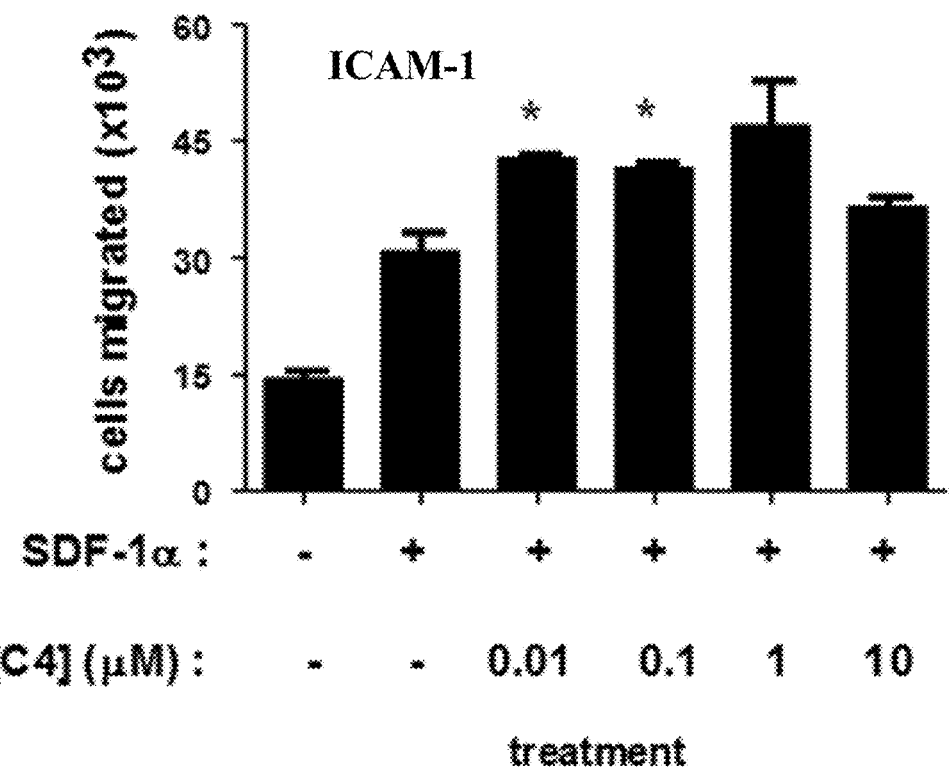

As such, the compounds can also facilitate chemotactic cell migration on the α4β1 integrin substrate vascular cell adhesion molecule-1 (VCAM-1) and the αLβ2 integrin substrate intercellular adhesion molecule-1 (ICAM-1) as shown in FIGS. 3A&B.

Because C4 can activate cell adhesion, it is predicted to enhance the immune response through a number of different mechanisms. This could be by augmenting antigen presentation between lymphocytes and antigen presenting cells. This could also be through increased effector cell trafficking to sites of an immune response. Importantly, augmented immune responses could be the result of more efficient cytolytic effector cell killing of tumor target cells. This could be in the context of simple NK cell or CTL mediated killing, or in the context of target cell killing via ADCC.

Augmentation of NK Cytolytic Activity by C4

Integrins, including C4 targets α4β1 and αLβ2, are essential in CTL and NK cell dependent killing of tumor targets. Thus, by facilitating cell adhesion, C4 should increase tumor target killing by effector cells. To test this general concept, freshly isolated NK cells, or the NK cell line NK92 were mixed with K562 tumor targets in standard cytotoxicity assays with, or without, C4. C4 enhanced NK and NK92-mediated killing of K562 tumor target cells see FIGS. 1 and 2. Although the target cells in this example are erythroleukemic cells, these results are extendible to solid tumors as well as many of these tumor types express the ligands for integrins α4β1 and αLβ2.

Checkpoint Blockade is Mediated by ADCC

Effectiveness of anti-CTLA4 therapy in melanoma patients is due in part to ADCC dependent selective depletion of negative regulatory T cells in a solid tumor. This has also been shown to the case in animal models of melanoma. When anti-CTLA-4 mAb (clone 9H10) is administered in combination with a vaccine termed GVAX®, melanoma regression occurs as regulatory T cells are depleted by Fc receptor bearing cells in the tumor microenvironment. As C4 can enhance the cytolytic mechanisms involved in ADCC, it was hypothesized that C4 would be able to augment the therapeutic effects of anti-CTLA-4 treatment (in particular with the anti-CTLA-4 mAb clone 9H10) in an experimental model of melanoma.

C4 Enhancement of GVAX®/Anti-CTLA-4 Treatment

C4 was tested in a β16-BL6 melanoma model to determine potential effects on the current checkpoint blockade therapy anti-CTLA-4. Briefly, thirty C57BL/6 were randomized into 3 groups (n=10). C4 was added to a regimen of GVAX®/anti-CTLA-4. Historically, these treatment regimens result in at best, a 20% tumor free survival. On day 0, β16-BL6 cells ($2.5 \times 10^4$) were injected subcutaneously. GVAX®/anti-CTLA-4 (clone 9H10), or IgG controls, were administered on days 3, 6, and 9. On day 11, C4 treatment was initiated intratumorally twice weekly (1 mg/kg) for 30 days. Vehicle control was added to the IgG group. Addition of C4 to the GVAX®/anti-CTLA-4 treatment group demonstrated a significant median survival benefit (Table III) along with a significant increase in long term tumor free survival (Table IV).

TABLE III

C4 Increases Median Survival of Mice with
Metastatic Melanoma in Combination with Anti-CTLA-4

| Treatment Group | Median Survival (days) | Comparisons | Hazard Ratio | 95% CI of Ratio | P value |
|---|---|---|---|---|---|
| Untreated | 29.00 | | | | |
| anti-CTLA-4 | 32.00 | Untreated vs. Anti- | 0.32 | 0.06 to 0.36 | <0.05 |

TABLE III-continued

C4 Increases Median Survival of Mice with
Metastatic Melanoma in Combination with Anti-CTLA-4

| Treatment Group | Median Survival (days) | Comparisons | Hazard Ratio | 95% CI of Ratio | P value |
|---|---|---|---|---|---|
| anti-CTLA-4 + C4 | 71.50 | CTLA-4 Anti-CTLA-4 vs. Anti-CTLA-4 + THI349 | 0.37 | 0.10 to 0.90 | <0.05 |

Notes:
At day 0, C57BL/6 mice were implanted with 2.5 × 10$^4$ B16BL6 melanoma cells, and on day 3, 6, 9, treated with Anti-CTLA-4, clone 9H10, Bioxcell, 10 mg/kg) with and without C4 (intratumorally, 1 mg/kg, twice weekly for 30 days) in a GVAX ® background.
P value by Log-rank, time to event based on tumor burden of 200 mm$^2$.
The censor day on the survival data was 100 days.

TABLE IV

C4 Increases the Incidence of Long-term Tumor Rejection in
Combination with Anti-CTLA-4 in Mice with Metastatic Melanoma

| Treatment Group | # to Tumor free animals | Comparisons | P value (Chi-square) |
|---|---|---|---|
| Untreated | 0.0% | | |
| anti-CTLA-4 | 11.1% | Untreated vs. Anti-CTLA-4 | 0.14 |
| anti-CTLA-4 + C4 | 50.0% | Anti-CTLA-4 vs. Anti-CTLA-4 + C4 | 0.03 |

Notes:
P value by Chi-square one tailed.
Animal were palpated at the tumor injection site over a 100 day period for the presence of a tumor.

C4 has demonstrated significant increases in median survival times and long term tumor free survival in combination with the checkpoint blockade treatment anti-CTLA-4. Notably, the animal model data presented above utilized the same anti-CTLA-4 clone, mAb clone 9H10, which has been shown to produce therapeutic effects in this model by ADCC.

C4 and related compounds of Formula (I), enhance cell adhesion mediated by integrins that are essential for ADCC. In an in vivo tumor model, C4 significantly enhanced the therapeutic efficacy of a CTLA-4 antibody, mAb clone 9H10, which is known to be effective through ADCC. By extension, C4 and related compounds of Formula (I) are thought to be effective via enhancement of ADCC.

Figure 4A:
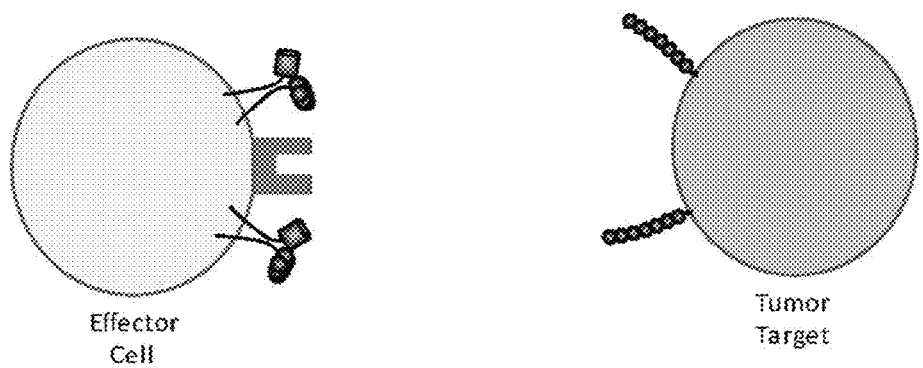
FIGS. 4A-C depict a mechanism of ADCC.
Figure 4B:
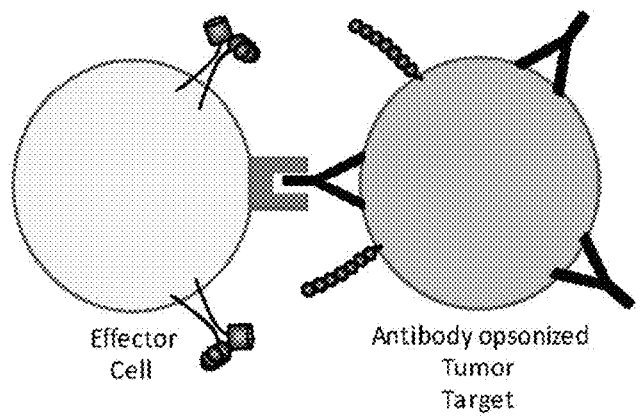
Figure 4C:
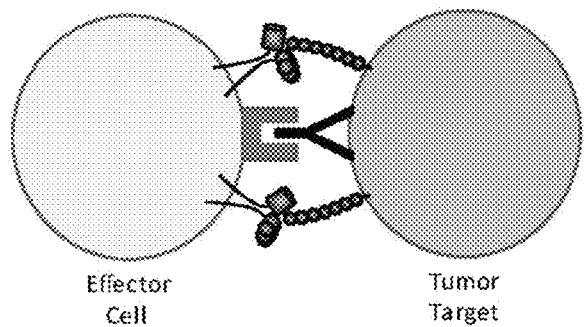
Figure 4C:
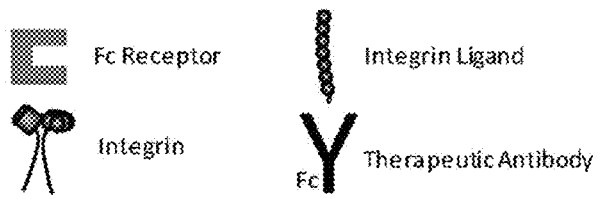

Antibody dependent cellular cytotoxicity (ADCC) is a mechanism whereby antibodies bind a cell surface antigen, opsonizing the cell for engulfment (phagocytosis) and/or destruction by effector cells of the immune system such as neutrophils, macrophage, and NK cells that express activating receptors (e.g., Fc receptors) for the Fc components of antibodies see FIGS. 4A-C.

Referring to FIGS. 4A-C, a mechanism of ADCC is shown. Looking at FIG. 4A, a tumor target cell unbound with therapeutic antibody, no ADCC occurs. Looking at FIG. 4B, an Fc receptor binds to therapeutic antibody bound tumor target cell, but weak adhesion between effector and target cell results in weak ADCC. Looking at FIG. 4C, the Fc receptor on effector cell binds to therapeutic antibody bound tumor target, and strong adhesion mediated by integrins between effector and target cell results in strong ADCC.

Enhancing ADCC with small molecule integrin activators would promote ADCC and serve as an adjunct therapy with any therapeutic antibody with an Fc component that may mediate ADCC. The results presented here demonstrate the ability of C4 to augment the therapeutic activity of mAb 9H10, which acts in vivo through a mechanism of ADCC. By extension, this mechanism of action could be applied to enhance therapeutic efficacy of any mAb treatment for which ADCC may occur.

Experiments Relating to ADCC

Reagents and Cell Lines

For all assays described, C4 was dissolved in DMSO to make a 1 mM stock solution, and dilutions were made in assay buffer or media to yield the desired final working concentrations in 1% DMSO (vehicle). Human VCAM-1, MAdCAM-1 Fc chimera, ICAM-1, and SDF-1a were purchased from R&D Systems (Minneapolis, Minn.). Human serum fibronectin was purchased from Sigma-Aldrich (St. Louis, Mo.). The cell lines NK-92, Jurkat, K562, and HSB were obtained from American Type Culture Collection (Manassas, Va.) and were maintained in recommended culture media. The mutant Jurkat cell line not expressing α4 integrin (Jurkat [α4−]) was a gift from Dr. David Rose, University of California San Diego, La Jolla, Calif.

Static Cell Adhesion Assays

Ligands (VCAM-1, MAdCAM-1, fibronectin, or ICAM-1) in 50 μL of 50 mM Tris-HCl (pH 7.4), 150 mM NaCl, (TBS) were added to wells of a 96-well plate and allowed to coat overnight at 4° C. In order to maximize the window to evaluate agonist activity, a sub-optimal coating concentration of ligand was used. This ligand concentration corresponded approximately to that which would yield ≤5% adhesion as determined by dose-response curves of ligand binding to the appropriate cell type. All assays were performed as previously described. Briefly, 2×10$^6$ cells were labeled for 30 minutes with calcein-AM (Molecular Probes), washed, resuspended in binding buffer, and added to ligand-coated plates (2×10$^5$ cells/well) that had been blocked with 2% BSA. The binding buffer was PBS with 1 mM MgCl$_2$ and 50% FBS (VCAM-1 and ICAM-1 assays) or TBS with 1 mM MnCl$_2$ and 50% FBS (MAdCAM-1 and fibronectin assays). After a 30-minute incubation at 37° C., the plates were washed 3 times with the respective binding buffer (except without the serum), the adherent cells were lysed, and fluorescence was measured on a Tecan Safire$^2$ plate reader. Standard curves were run for each assay to convert fluorescence units to cell number. For each assay, the cells expressed the appropriate integrin receptor either endogenously (Jurkat/α4β1, K562/α5β1, Jurkat (α4−)/αLβ2, HSB/αLβ2) or in recombinant form (K562/437). Generation of the recombinant K562 cell line has been described.

Migration Assays

Migration assays were performed in 3 μM pore size Transwells (24 well, Costar, Cambridge, Mass.). The upper chambers were pre-coated with 10 mg/mL VCAM-1 or 1 μg/mL ICAM-1 in 50 mL TBS overnight at 4° C. and were then blocked with 2% BSA for 1 hour at room temperature. After washing with migration medium (RPMI-1640 supplemented with 1% FBS, 100 units/mL penicillin and 100 μg/mL streptomycin), upper chambers were loaded with 2×10$^5$ cells Jurkat cells (VCAM-1 assays) or Jurkat (α4-) cells (ICAM-1 assays) in 160 μL of migration medium. Lower chambers contained 600 μL of migration medium supplemented with 5 μg/mL (VCAM-1 assays) or 1 μg/mL (ICAM-1 assays) SDF-1α to induce chemotaxis. Jurkat cells were mixed with vehicle (1% DMSO) or C4 at the indicated concentrations immediately prior to being added to the upper chamber. After a 4-hour incubation at 37° C., 5% CO$_2$, the upper chambers were removed, and cells in the lower chamber were collected and counted on a hemocytometer. Results are expressed as the total number of cells migrated.

Checkpoint Blockade Melanoma Model

The B16-BL6 therapeutic melanoma model is well described. Briefly, B16-BL6 cells (>90% viability) were be resuspended at 2.5×105 cells/ml in HBSS (4° C.). At day 0 (d0), C57BL/6 mice (4-6 wk old, female) were inoculated (subcutaneous, flank) with 2.5×10$^4$ cells (100 μL). At d3, appropriate groups received β16-GM-CSF vaccine (GVAX®). GVAX® preparation followed established procedures. Log-phase growth B16-GM-CSF cells were harvested as described above for β16-BL6 cells, but resuspended at 1×10$^7$ cells in HBSS (4° C.). Cells were irradiated (5000 rad) and injected into contralateral flanks (100 μL, 1×10$^6$ cells). Also at d3, all animals received anti-CTLA-4 (mAb 9H10, BioXcell, 200 μg/animal, twice weekly). C4 (1 mg/kg in 25 μL 2× weekly intratumoral), or control vehicle (Veh, 25 μL), was administered at dl 1 in appropriate groups. At d12 and every 2 days thereafter, all animals were observed for tumor growth. Calipers were used to measure perpendicular tumor diameters. Animals were monitored daily for distress and survival was assessed twice daily. Lack of survival was defined as death, or tumor size >200 mm$^2$.

NK Cytotoxicity Testing

Human NK cells were purified from leukoreduction filters obtained from healthy volunteers using a CD56+ magnetic bead based enrichment column from Multenyi Biotech (as per manufacturer's instructions). Purified cells were routinely >90% CD56+ positive as measured by flow cytometry. For cytotoxicity testing, logarithmically growing K562 target cells were labeled with BATDA (bis (acetoxymethyl) 2,2':6',2"-terpyridine-6,6"-dicarboxylate, Perkin Elmer DELFIA EuTDA Cytotoxicity Reagent, Catalogue # ADO 116, as per manufacturer's instructions). In round bottom 96-well plates, 1×10$^4$ K562 tumor target cells were added in 100 μL of culture media. This was followed by the addition of NK cells, at indicated effector to target ratios in a volume of 100 μL of culture media. C4 was then added to wells, at indicated concentrations. After a 4 h incubation at 37° C., 5% CO$_2$, culture supernatants were removed and liberated TDA (2,2':6',2"-terpyridine-6,6"-dicarboxylic acid) was detected by addition of DELFIA solution to form EuTDA, and fluorescence was measured on a Tecan Safire 2 multimodal plate reader. For determination of maximal cell lysis, 1.0% TritonX-100 was added to control wells prior to removal of supernatant. For spontaneous release of TDA, labelled K562 were incubated identically as described above, in the presence of C4, but without NK effector cells.

Results are expressed as the percent specific lysis, calculated as [(experimental signal−spontaneous release)/(total signal−spontaneous release).

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method comprising:
   administering to a subject:
   (A) an antigen, and
   (B) an adjuvanting amount of at least one integrin activating compound that increases an immune response to the antigen,
   wherein the at least one integrin activating compound comprises one or more compounds of the general Formula (I):

$$R^1\text{-}M^1\text{-}N(R^2)\text{-}M^2\text{-}M^3\text{-}M^4\text{-}M^5\text{-}M^6\text{-}R^3 \qquad (I)$$

wherein a first class of the compounds of Formula (I) is defined by:
   R$^1$ is selected from the group consisting of aryl and aralkyl,
   R$^2$ is alkyl, aryl, or aralkyl,
   M$^2$ is CH$_2$,
   M$^2$ is CO,
   M$^3$ is O, S, or NR$^6$,
   R$^6$ when present is hydrogen or lower alkyl,
   M$^4$ is absent or CH$_2$,
   M$^5$ is (CR$^{11}$R$^{12}$),
   R$^{11}$ is hydrogen,
   R$^{12}$ is selected from the group consisting of hydrogen, NR$^{21}$CONR$^{22}$R$^{23}$, NR$^{21}$COR$^{24}$, NR$^{21}$SO$_2$R$^{24}$, NR$^{21}$COOR$^{24}$, OCOR$^{24}$, OR$^{24}$, O(CH$_2$CH$_2$O)$_s$R$^{24}$, COOR$^{24}$, alkyl, and hydroxyalkyl,
   s is an integer of 1 to 6,
   R$^{21}$ and R$^{22}$ when present are independently selected from the group consisting of hydrogen or lower alkyl,
   R$^{23}$ when present is selected from the group consisting of hydroxyalkyl, alkoxyalkyl, alkyl, aryl, aralkyl and alkoxycarbonylalkyl,
   provided that when M$^3$ is NR$^6$ and M$^4$ is absent, then R$^{23}$ is not 1-(1,3-benzodioxol-5-yl)-3-ethoxy-3-oxopropyl,
   R$^{24}$ when present is selected from the group consisting of alkyl, aryl, aralkyl, heterocyclyl, cycloalkyl, cycloalkylalkyl, and heterocyclylalkyl, and mixtures thereof,
   M$^6$ is (CH$_2$)$_q$, where
   q is an integer from 0 to 6,
   R$^3$ is selected from the group consisting of hydrogen, CONR$^{13}$R$^{14}$, NR$^{15}$COOR$^{16}$, NR$^{15}$COR$^{16}$, NR$^{15}$CONR$^{13}$R$^{14}$, NR$^{15}$SO2R$^{16}$, OCOR$^{16}$, COOR$^{16}$, OR$^{16}$, SR$^{16}$, heterocyclyl, hydroxyl, hydroxyalkyl, guanadino, alkyl and aryl,
   R$^{13}$ and R$^{15}$ when present are independently hydrogen or lower alkyl,
   R$^{14}$ and R$^{16}$ when present are independently selected from the group consisting of hydrogen, alkyl, aryl, aralkyl, cycloalkyl, heterocyclyl, cycloalkylalkyl, and heterocyclylalkyl, $R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, NHCO(alkyl), NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures thereof;

or wherein a second class of the compounds of Formula (I) is defined by:
$R^1$ is aryl or aralkyl,
$R^2$ is alkyl or aralkyl,
$M^1$ is CH$_2$,
$M^2$ is CO,
$M^3$ is absent or is O or CH$_2$,
$M^4$ is absent or is CH$_2$,
$M^5$ is absent or is O or (CR$^{11}$R$^{12}$),
$R^{11}$ is hydrogen,
$R^{12}$ is selected from the group consisting of hydrogen, NR$^{21}$CONR$^{22}$R$^{23}$, NR$^{21}$COR$^{24}$, NR$^{21}$SO2R$^{24}$ and NR$^{21}$COOR$^{24}$,
$R^{21}$ and $R^{22}$ each of which, when present is independently selected from the group of hydrogen and lower alkyl,
$R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl,
$M^6$ is selected from the group consisting of (CH$_2$)$_q$, (CH$_2$)$_q$—CH=CH—(CH$_2$)$_r$, (CH$_2$)$_q$-arylene-(CH$_2$)$_r$ and (CH$_2$CH$_2$O)$_q$, where
q and r are independently integers from 0 to 6,
$R^3$ is CONR$^{13}$R$^{14}$,
$R^{13}$ and $R^{14}$, each of which, when present is independently selected from the group consisting of hydrogen, alkyl, aryl, cycloalkyl, cycloalkylalkyl, heterocyclyl, heterocyclylalkyl and aralkyl, and
$R^1$, $R^2$, $R^{13}$, $R^{14}$, $R^{23}$ and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures thereof;

or wherein a third class of the compounds of Formula (I) is defined by:
$R^1$ is aryl or aralkyl,
$R^2$ is alkyl or aralkyl,
$M^1$ is CH$_2$,
$M^2$ is SO$_2$ or CO
$M^3$ is absent or is CH$_2$,
$M^4$ is absent or is CH$_2$,
$M^5$ is absent or is (CR$^{11}$R$^{12}$),
$R^{11}$, when present, is hydrogen,
$R^{12}$, when present, is selected from the group consisting of hydrogen, alkyl, NR$^{21}$CONR$^{22}$R$^{23}$, NR$^{21}$COR$^{24}$, NR$^{21}$SO2R$^{24}$ and NR$^{21}$COOR$^{24}$,
$R^{21}$ and $R^{22}$, each of which when present, is independently selected from the group of hydrogen, lower alkyl, and aralkyl,
$R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl,
$M^6$ is (CH$_2$)$_q$, or NR$^{34}$(CH$_2$)$_q$,
q is an integer from 0 to 6,
$R^{34}$, when present, is selected form the group consisting of alkyl, aralkyl, COR$^{35}$, and SO$_2$R$^{35}$,
$R^{35}$ when present, is selected form the group consisting of alkyl, aryl, and aralkyl, and
$R^3$ is selected from the group consisting of CONR$^{13}$R$^{14}$, SO$_2$NR$^{13}$R$^{14}$, NR$^{15}$COOR$^{16}$, NR$^{15}$COR$^{16}$, NR$^{15}$CONR$^{13}$R$^{14}$, and NR$^{15}$SO$_2$R$^{16}$,
$R^{13}$ and $R^{14}$, each of which, when present, is independently selected from the group consisting of hydrogen, alkyl, aryl, cycloalkyl, cycloalkylalkyl, heterocyclyl, heterocyclylalkyl and aralkyl,
$R^{15}$ and $R^{16}$, each of which when present, is independently selected from the group of hydrogen, lower alkyl, and aralkyl,
$R^1$, $R^2$, $R^{13}$, $R^{14}$, $R^{15}$, $R^{16}$, $R^{23}$, $R^{24}$, $R^{34}$ and $R^{35}$, when present, either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino), with the proviso that when $M^2$ is CO, then
$M^6$ is NR$^{34}$(CH$_2$)$_q$,
q is not 0;

or wherein a four class of the compounds of Formula (I) is defined by:
$R^1$ is alkyl, aryl or aralkyl,
$R^2$ is selected from the group consisting of aralkyl and alkyl,
provided that when $R^1$ is alkyl, $R^2$ is aralkyl,
$M^1$ is CO or SO$_2$,
provided that when $M^1$ is SO$_2$ and $R^1$ is phenyl, 4-methylphenyl or 2,4,6-trimethylphenyl, $R^2$ is not alkyl, 2-phenethyl, benzyl, or 2-methoxy-2-oxoethyl, and when $M^1$ is CO and $R^1$ is 2-furyl, 4-pyridyl, or 3,5-dinitrophenyl, $R^2$ is not alkyl, benzyl or 2-(1H-indol-2-yl)ethyl,
$M^2$ is absent or CH$_2$,
$M^3$ and $M^4$ are absent,
$M^5$ is (CR$^{11}$R$^{12}$),
$R^{11}$ is hydrogen,
$R^{12}$ is selected from the group consisting of hydrogen, NR$^{21}$CONR$^{22}$R$^{23}$, NR$^{21}$COR$^{24}$, NR²¹SO₂R²⁴, NR²¹COOR²⁴, CONR²²R²³, COOR²⁴, O(CH₂CH₂O)$_s$R²⁴, hydroxyalkyl, and alkoxyalkyl, R²¹, and R²², when present, are independently selected from the group consisting of hydrogen and C₁-C₆ alkyl, and R²³ and R²⁴, each of which, when present, is independently selected from the group consisting of hydrogen, alkyl, aryl, cycloalkyl, cycloalkylalkyl, heterocyclyl, heterocyclylalkyl and aralkyl, and s is an integer of 1 to 6, M⁶ is (CH₂)$_q$, q is an integer of 0 to 6, R³ is selected from the group consisting of NR¹⁵COOR¹⁶, NR¹⁵COR¹⁶, NR¹⁵CONR¹³R¹⁴, and NR¹⁵SO₂R¹⁶, and R¹³ when present, is independently selected from the group consisting of hydrogen and C₁-C₆ alkyl, and R¹⁴, R¹⁵, and R¹⁶ each of which, when present, are independently selected from the group consisting of hydrogen, alkyl, aryl, cycloalkyl, cycloalkylalkyl, heterocyclyl, heterocyclylalkyl and aralkyl, and R¹, R², R³, R¹², R¹⁴, R¹⁵, R¹⁶, R²³, and R²⁴, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO₂(alkyl), —NHSO₂(aryl), —NHSO₂(aralkyl), alkoxycarbonyl, alkoxycarbonylalkyl, —OCO(alkylamino) and —OCO(dialkylamino), or pharmaceutically acceptable salts thereof.

2. The method of claim 1, wherein the administering step include:

administering the antigen with the at least one integrin activating compound.

3. The method of claim 1, wherein, in the administering step, the integrin is selected from the group consisting of α4β1, α4β7, α5β1, and αLβ2.

4. The method of claim 1, wherein, in the administering step, the integrin is selected from the group consisting of α4β1 and αLβ2.

5. The method of claim 1, wherein, in the administering step, the at least one integrin activating compound is administered before, during, or after administering the antigen.

6. The method of claim 1, wherein, in the administering step, R¹M¹, R², R¹³, and R¹⁴ are independently selected from the group consisting of 2-thienylmethyl, 3-methoxybenzyl, 4-methoxybenzyl, 4-(dimethylamino)benzyl, 2-(2-thienyl)ethyl, pyridin-4-ylmethyl, and pyridin-3-ylmethyl.

7. The method of claim 1, wherein, in the administering step:

the first class of the compounds are selected from the group consisting of N,N,N',N'-tetrakis(2-thienylmethyl)pentanediamide; N-(3-methoxybenzyl)-N,N',N'-tris(2-thienylmethyl)pentanediamide; N,N,N'-tris(2-thienylmethyl)pentanediamide; N'-[2-(2-thienyl)ethyl]-N,N-bis(2-thienylmethyl)pentanediamide; N-[2-(2-thienyl)ethyl]-N,N',N'-tris(2-thienylmethyl) pentanediamide; N,N-bis(pyridin-4-ylmethyl)-N',N'-bis(2-thienylmethyl)pentanediamide; N,N-bis(pyridin-3-ylmethyl)-N',N'-bis(2-thienylmethyl) pentanediamide; N,N-bis(3-methoxybenzyl)-N',N'-bis (2-thienylmethyl)pentanediamide; N,N,N',N'-tetrakis (4-methoxybenzyl)pentanediamide; N,N,N',N'-tetrakis (2-thienylmethyl)hexanediamide; N,N,N',N'-tetrakis (4-methoxybenzyl) hexanediamide; N,N,N',N'-tetrakis (3-methoxybenzyl)hexanediamide; N,N,N',N'-tetrakis (2-thienylmethyl) heptanediamide; 2,2'-(1,3-phenylene)bis[N,N-bis(2-thienylmethyl)acetamide]; N,N,N',N'-tetrakis(4-methoxybenzyl)heptanediamide; N,N,N',N'-tetrakis (2-thienylmethyl)octanediamide; (3E)-N,N,N',N'-tetrakis (2-thienylmethyl)hex-3-enediamide; 2,2'-oxybis[N,N-bis(2-thienylmethyl)acetamide]; 3-oxo-1-(2-thienyl)-2-(2-thienylmethyl)-4,7,10-trioxa-2-azadodecan-12-yl bis(2-thienylmethyl)carbamate; N,N,N',N'-tetrakis(4-methoxybenzyl) succinamideethane-1,2-diyl bis[bis(2-thienylmethyl)carbamate]; N,N,N',N'-tetrakis (4-methoxybenzyl)octanediamide; N,N,N',N'-tetrakis(2-thienylmethyl) pyridine-3,5-dicarboxamide; N,N,N',N'-tetrakis (2-thienylmethyl) pyridine-2,6-dicarboxamide; N,N,N',N'-tetrakis (2-thienylmethyl)pyridine-2,4-dicarboxamide; 2,2'-(1,4-phenylene) bis[N,N-bis(2-thienylmethyl)acetamide]; 8-{2-[bis (2-thienylmethy)amino]-2-oxoethoxy}-N,N-bis(2-thienylmethyl)quinoline-2-carboxamide; N,N'-bis(4-methoxybenzyl)-N,N'-bis(2-thienylmethyl) hexanediamide; and tert-butyl{(2S)-1,6-bis[bis(2-thienylmethyl)amino]-1,6-dioxohexan-2-yl}carbamate;

the second class of the compounds are selected from the group consisting of 1,2-bis(bis(thiophen-2-ylmethyl) carbamate)ethane; 1,2-bis(bis(3-methyloxybenzyl)carbamate)ethane; 1,2-bis(bis(4-methyloxybenzyl)carbamate)ethane; 1,2-bis((thiophen-2-ylmethyl)(3-methyloxybenzyl)carbamate)ethane; 1,2-bis((thiophen-2-ylmethyl)(4-methyloxybenzyl) carbamate)ethane; 1,2-bis((3-methyloxybenzyl)(4-methyloxybenzyl)carbamate)ethane; 1,5-bis(bis (thiophen-2-ylmethyl)carbamate)-3-oxapentane; 1,5-bis(bis(3-methyloxybenzyl)carbamate)-3-oxapentane; 1,5-bis(bis(4-methyloxybenzyl)carbamate)-3-oxapentane; 1,5-bis((thiophen-2-ylmethyl)(3-methyloxybenzyl)carbamate)-3-oxapentane; 1,5-bis((thiophen-2-ylmethyl)(4-methyloxybenzyl)carbamate)-3-oxapentane; 1,5-bis((3-methyloxybenzyl)(4-methyloxybenzyl)carbamate)-3-oxapentane; (ethane-1,2-diylbis(oxy))bis (ethane-2,1-diyl)bis(bis(thiophen-2-ylmethyl)carbamate) or 1,8-bis(bis(thiophen-2-ylmethyl)carbamate)-3,6-dioxaoctane; 1,8-bis(bis(3-methyloxybenzyl) carbamate)-3,6-dioxaoctane; 1,8-bis(bis(4-methyloxybenzyl)carbamate)-3,6-dioxaoctane; 1,8-bis ((thiophen-2-ylmethyl)(3-methyloxybenzyl) carbamate)-3,6-dioxaoctane; 1,8-bis((thiophen-2-ylmethyl)(4-methyloxybenzyl)carbamate)-3,6-dioxaoctane; 1,8-bis((3-methyloxybenzyl)(4-methyloxybenzyl)carbamate)-3, 6-dioxaoctane; 1,11-bis(bis(thiophen-2-ylmethyl)carbamate)-3,6,9-trioxaundecane; 1,11-bis (bis (3-methyloxybenzyl) carbamate)-3,6,9-trioxaundecane; 1,11-bis(bis(4-methyloxybenzyl)carbamate)-3,6,9-trioxaundecane; 1,11-bis((thiophen-2-ylmethyl)(3-methyloxybenzyl) carbamate)-3,6,9-trioxaundecane; 1,11-bis((thiophen-2-ylmethyl)(4-methyloxybenzyl)carbamate)-3,6,9-trioxaundecane; 1,11-bis((3-methyloxybenzyl)(4-methyloxybenzyl)carbamate)-3,6,9-trioxaundecane;

1,14-bis(bis(thiophen-2-ylmethyl)carbamate)-3,6,9,12-tetraoxatetradecane; 1,14-bis(bis(3-methyloxybenzyl)carbamate)-3,6,9,12-tetraoxatetradecane; 1,14-bis(bis(4-methyloxybenzyl)carbamate)-3,6,9,12-tetraoxatetradecane; 1,14-bis((thiophen-2-ylmethyl)(3-methyloxybenzyl)carbamate)-3,6,9,12-tetraoxatetradecane; 1,14-bis((thiophen-2-ylmethyl)(4-methyloxybenzyl)carbamate)-3,6,9,12-tetraoxatetradecane; 1,14-bis((3-methyloxybenzyl)(4-methyloxybenzyl)carbamate)-3,6,9,12-tetraoxatetradecane; 1,17-bis(bis(thiophen-2-ylmethyl)carbamate)-3,6,9,12,15-pentaoxatetradecane; 1,17-bis(bis(3-methyloxybenzyl)carbamate)-3,6,9,12,15-pentaoxatetradecane; 1,17-bis(bis(4-methyloxybenzyl)carbamate)-3,6,9,12,15-pentaoxatetradecane; 1,17-bis((thiophen-2-ylmethyl)(3-methyloxybenzyl)carbamate)-3,6,9,12,15-pentaoxatetradecane; 1,17-bis((thiophen-2-ylmethyl)(4-methyloxybenzyl)carbamate)-3,6,9,12,15-pentaoxatetradecane; and 1,17-bis((3-methyloxybenzyl)(4-methyloxybenzyl)carbamate)-3,6,9,12,15-pentaoxatetradecane;

the third class of the compounds are selected from the group consisting of methyl (6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-9-methyl-3,8-dioxo-1-(2-thienyl)-2-(2-thienylmethyl)-4-oxa-2,7,9-triazadodecan-12-oate; ethyl (6S,1OR)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (10S)-10-(1,3-benzodioxol-5-yl)-3,8-dioxo-1-(2-thienyl)-2-(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-2-methyl-3,8-dioxo-1-(2-thienyl)-4-oxa-2,7,9-triazadodecan-12-oate; methyl (6S)-6-butyl-3,8-dioxo-1-(2-thienyl)-2-(2-thienylmethyl)-4-oxa-2,7,9-triazadodecan-12-oate; (2S)-2-{[(1,3-benzodioxol-5-ylmethyl)carbamoyl]amino}hexyl bis(2-thienylmethyl)carbamate; methyl (6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl]carbamoyl}amino)hexylbis(2-thienylmethyl)carbamate; (2S)-2-[(benzylcarbamoyl)amino]hexylbis(2-thienylmethyl)carbamate; (2S)-2-[(morpholin-4-ylcarbonyl)amino]hexylbis(2-thienylmethyl)carbamate; (2S)-2-{[(3-methoxypropyl)carbamoyl]amino}hexylbis(2-thienylmethyl)carbamate; (2S)-2-{[(2-methoxyethyl)carbamoyl]amino}hexylbis(2-thienylmethyl)carbamate; tert-butyl[(2S)-1-{[bis(2-thienylmethyl)carbamoyl]oxy}hexan-2-yl]carbamate; (2S)-2-[(tert-butylcarbamoyl)amino]hexyl bis(2-thienylmethyl)carbamate; (2S)-2-[(isopropylcarbamoyl)amino]hexylbis(2-thienylmethyl)carbamate; (2S)-2-[(methylcarbamoyl)amino]hexyl bis(2-thienylmethyl)carbamate; tert-butyl[(2R)-1-{[bis(2-thienylmethyl)carbamoyl]oxy}hexan-2-yl]carbamate; benzyl {(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; (2S)-2-acetamidohexylbis(2-thienylmethyl)carbamate; methyl(6R,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl {[bis(2-thienylmethyl)carbamoyl](methyl)amino}acetate; methyl {[bis(2-thienylmethyl)carbamoyl](butyl)amino}acetate; tert-butyl {[bis(2-thienylmethyl)carbamoyl](butyl)amino}acetate; benzyl {(5S)-6-{[bis(4-methoxybenzyl)carbamoyl]oxy}-5-[(tert-butoxycarbonyl)amino] hexyl}carbamate; tert-butyl [(2S)-1-{[bis(4-methoxybenzyl)carbamoyl]oxy}hexan-2-yl]carbamate; methyl (6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-24 {[(1S)-1-(1,3-benzodioxol-5-yl)-3-hydroxypropyl]carbamoyl}amino) hexyl bis(4-methoxybenzyl)carbamate; (2S)-2-[(tertbutoxycarbonyl)amino]hexyl dibenzylcarbamate; methyl (6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl)carbamoyl]oxy}hexan-2-yl]carbamate; methyl (6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl (6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; (2S)-2-[(tertbutoxycarbonyl)amino]hexyl(4-bromobenzyl)(2-thienylmethyl)carbamate; methyl (6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl (6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexylphenyl(2-thienylmethyl)carbamate; methyl (6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl)carbamoyl]oxy}hexan-2-yl]carbamate; methyl (6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tertbutoxycarbonyl)amino]-6-{[butyl (2-thienylmethyl)carbamoyl]oxy}hexyl]carbamate; (2S)-2-[(tert-butoxycarbonyl)amino]hexylbutyl(2-thienylmethyl)carbamate; methyl (3S,7S)-3-(1,3-benzodioxol-5-yl)-7-butyl-5,11-dioxo-11-(2-thienylmethyl)-9-oxa-4,6, 11-triazapentadecan-1-oate; benzyl[(5S)-5-[(tert-butoxycarbonyl)amino]-6-{[(2-methoxyethyl)(2-thienylmethyl)carbamoyl]oxy}hexyl] carbamate; (2S)-2-[(tert-butoxycarbonyl)amino]hexyl (2-methoxyethyl)(2-thienylmethyl)carbamate; methyl (9S,13S)-13-(1,3-benzodioxol-5-yl)-9-butyl-6,11-dioxo-5-(2-thienylmethyl)-2,7-dioxa-5,10,12-triazapentadecan-15-oate; (2S)-2-[({3-[(methylsulfonyl)amino]benzyl}carbamoyl)amino]hexyl(2-methoxyethyl)(2-thienylmethyl)carbamate; (2S)-2-{[(4-bromobenzyl)carbamoyl]amino}hexylbis(2-thienylmethyl)carbamate; (2S)-2-{[(4-azidobenzyl)carbamoyl]amino}hexylbis(2-thienylmethyl)carbamate; tert-butyl [(2S)-1-{[bis(2-thienylmethyl)carbamoyl]thio}hexan- 2-yl]carbamate; and methyl (6S,10S)-10-(1,3-benzodioxol-5-yl)-6-butyl-3,8-dioxo-1-(2-thienyl)-2-(2-thienylmethyl)-4-thia-2,7,9-triazadodecan-12-oate;

the four class of the compounds are selected from the group consisting of N-{2-[bis(2-thienylmethyl)sulfamoyl]ethyl}-N-(2-thienylmethyl)thiophene-2-sulfonamide; N-{2-[bis(2-thienylmethyl)sulfamoyl]ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-{[bis(2-thienylmethyl)carbamoyl](butyl)amino}-N,N-bis(2-thienylmethyl) ethanesulfonamide; N-{3-[bis(2-thienylmethyl)sulfamoyl]propyl}-N-(2-thienylmethyl)thiophene-2-sulfonamide; 2-[(methylsulfonyl)(2-thienylmethy)amino]-N,N-bis(2-thienylmethyl) ethanesulfonamide; 2-{[bis(2-thienylmethyl)carbamoyl]amino}-N,N-bis(2-thienylmethyl) ethanesulfonamide; N-{2-[bis(2-thienylmethyl)sulfamoyl]ethyl}thiophene-2-sulfonamide; N-{2-[bis(2-thienylmethyl)sulfamoyl]ethyl}-2-(2-thienyl) acetamide; N-{2-[bis(2-thienylmethyl)sulfamoyl]ethyl}thiophene-2-carboxamide; N,N-bis(2-thienylmethyl)-2-{[(2-thienylmethyl)carbamoyl]amino}ethanesulfonamide; 2-({2-[bis(2-thienylmethyl)sulfamoyl]ethyl}amino)-N,N-bis(2-thienylmethyl)acetamide; 3-[{2-[bis(2-thienylmethyl)amino]-2-oxoethyl}(butyl)amino]-N,N-bis(2-thienylmethyl)propanamide; 2-[{2-[bis(2-thienylmethyl)sulfamoyl]ethyl}(methyl)amino]-N,N-bis(2-thienylmethyl)acetamide; 2-[{2-[bis(2-thienylmethyl) sulfamoyl]ethyl}(butyl)amino]-N,N-bis(2-thienylmethyl)acetamide; 3-({2-[bis(2-thienylmethyl)sulfamoyl]ethyl}amino)-N,N-bis(2-thienylmethyl)propanamide; 3-({2-[bis(2-thienylmethyl)sulfamoyl]ethyl}amino)-N,N-bis(4-methoxybenzyl) propanamide; 3-({2-[bis(4-methoxybenzyl)sulfamoyl]ethyl}amino)-N,N-bis(2-thienylmethyl)propanamide; 3-[{2-[bis(2-thienylmethyl)sulfamoyl]ethyl}(methyl)amino]-N,N-bis(2-thienylmethyl) propanamide; 3-[{2-[bis(4-methoxybenzyl) sulfamoyl]ethyl}(methyl)amino]-N,N-bis(2-thienylmethyl) propanamide; (2S)-2-({2-[bis(2-thienylmethyl)sulfamoyl]ethyl}amino)-N,N-bis(2-thienylmethyl) hexanamide; (2S)-2-({2-[bis(4-methoxybenzyl)sulfamoyl]ethyl}amino)-N,N-bis(2-thienylmethyl) hexanamide; 2-(acetyl{2-[bis(2-thienylmethyl)sulfamoyl]ethyl}amino)-N,N-bis(2-thienylmethyl) acetamide; and 2-(acetyl {2-[bis(4-methoxybenzyl) sulfamoyl]ethyl}amino)-N,N-bis(2-thienyl-methyl) acetamide;

pharmaceutically acceptable salts thereof; and mixtures thereof.

8. The method of claim 1, wherein, in the administering step, the antigen is an anti-cancer antigen.

9. The method of claim 8, wherein, in the administering step, the integrin is selected from the group consisting of α4β1, α4β7, α5β1, and αLβ2.

10. The method of claim 8, wherein, in the administering step, the integrin is selected from the group consisting of α4β1 and αLβ2.

11. A method comprising:
administering to a subject:
(A) one or more antigens, and
(B) an adjuvanting amount of one or more integrin activating compounds that increase an immune response to the one or more antigens, wherein the at least one integrin activating compound comprises one or more compounds of the general Formula (I):

$$R^1-M^1-N(R^2)-M^2-M^3-M^4-M^5-M^6-R^3 \quad (I)$$

wherein a first class of the compounds of Formula (I) is defined by:
$R^1$ is selected from the group consisting of aryl and aralkyl,
$R^2$ is alkyl, aryl, or aralkyl,
$M^1$ is $CH_2$,
$M^2$ is CO,
$M^3$ is O, S, or $NR^6$,
$R^6$ when present is hydrogen or lower alkyl,
$M^4$ is absent or $CH_2$,
$M^5$ is $(CR^{11}R^{12})$,
$R^{11}$ is hydrogen,
$R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl,
s is an integer of 1 to 6,
$R^{21}$ and $R^{22}$ when present are independently selected from the group consisting of hydrogen or lower alkyl,
$R^{23}$ when present is selected from the group consisting of hydroxyalkyl, alkoxyalkyl, alkyl, aryl, aralkyl and alkoxycarbonylalkyl,
provided that when $M^3$ is $NR^6$ and $M^4$ is absent, then $R^{23}$ is not 1-(1,3-benzodioxol-5-yl)-3-ethoxy-3-oxopropyl,
$R^{24}$ when present is selected from the group consisting of alkyl, aryl, aralkyl, heterocyclyl, cycloalkyl, cycloalkylalkyl, and heterocyclylalkyl, and mixtures thereof,
$M^6$ is $(CH_2)_q$, where
q is an integer from 0 to 6,
$R^3$ is selected from the group consisting of hydrogen, $CONR^{13}R^{14}$, $NR^{15}COOR^{16}$, $NR^{15}COR^{16}$, $NR^{15}CONR^{13}R^{14}$, $NR^{15}SO2R^{16}$, $OCOR^{16}$, $COOR^{16}$, $OR^{16}$, $SR^{16}$, heterocyclyl, hydroxyl, hydroxyalkyl, guanadino, alkyl and aryl,
$R^{13}$ and $R^{15}$ when present are independently hydrogen or lower alkyl,
$R^{14}$ and $R^{16}$ when present are independently selected from the group consisting of hydrogen, alkyl, aryl, aralkyl, cycloalkyl, heterocyclyl, cycloalkylalkyl, and heterocyclylalkyl,
$R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino), and mixtures thereof;

or
wherein a second class of the compounds of Formula (I) is defined by:
$R^1$ is aryl or aralkyl,
$R^2$ is alkyl or aralkyl,
$M^1$ is $CH_2$,
$M^2$ is CO,
$M^3$ is absent or is O or $CH_2$,
$M^4$ is absent or is $CH_2$,
$M^5$ is absent or is O or $(CR^{11}R^{12})$
  $R^{11}$ is hydrogen,
  $R^{12}$ is selected from the group consisting of hydrogen, $NR^{21}CONR^{22}R^{23}$, $NR^{21}COR^{24}$, $NR^{21}SO2R^{24}$ and $NR^{21}COOR^{24}$,
  $R^{21}$ and $R^{22}$ each of which, when present is independently selected from the group of hydrogen and lower alkyl,
  $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl,
$M^6$ is selected from the group consisting of $(CH_2)_q$, $(CH_2)_q$—CH=CH—$(CH_2)_r$, $(CH_2)_q$-arylene-$(CH_2)_r$ and $(CH_2CH_2O)_q$, where
q and r are independently integers from 0 to 6,
$R^3$ is $CONR^{13}R^{14}$,
  $R^{13}$ and $R^{14}$, each of which when present is independently selected from the group consisting of hydrogen, alkyl, aryl, cycloalkyl, cycloalkylalkyl, heterocyclyl, heterocyclylalkyl and aralkyl, and
$R^1$, $R^2$, $R^{13}$, $R^{14}$, $R^{23}$ and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), —OCO(dialkylamino), and mixtures thereof;
or
wherein a third class of the compounds of Formula (I) is defined by:
$R^1$ is aryl or aralkyl,
$R^2$ is alkyl or aralkyl,
$M^1$ is $CH_2$,
$M^2$ is $SO_2$ or CO,
$M^3$ is absent or is $CH_2$,
$M^4$ is absent or is $CH_2$,
$M^5$ is absent or is $(CR^{11}R^{12})$,
  $R^{11}$, when present, is hydrogen,
  $R^{12}$, when present, is selected from the group consisting of hydrogen, alkyl, $NR^{21}CONR^{22}R^{23}$, $NR^{21}COR^{24}$, $NR^{21}SO2R^{24}$ and $NR^{21}COOR^{24}$,
  $R^{21}$ and $R^{22}$, each of which when present, is independently selected from the group of hydrogen, lower alkyl, and aralkyl,
  $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $M^6$ is $(CH_2)_q$, or $NR^{34}(CH_2)_q$,
q is an integer from 0 to 6,
  $R^{34}$, when present, is selected form the group consisting of alkyl, aralkyl, $COR^{35}$, and $SO_2R^{35}$,
    $R^{35}$ when present, is selected form the group consisting of alkyl, aryl, and aralkyl, and
$R^3$ is selected from the group consisting of $CONR^{13}R^{14}$, $SO_2NR^{13}R^{14}$, $NR^{15}COOR^{16}$, $NR^{15}COR^{16}$, $NR^{15}CONR^{13}R^{14}$, and $NR^{15}SO_2R^{16}$,
  $R^{13}$ and $R^{14}$, each of which, when present, is independently selected from the group consisting of hydrogen, alkyl, aryl, cycloalkyl, cycloalkylalkyl, heterocyclyl, heterocyclylalkyl and aralkyl,
  $R^{15}$ and $R^{16}$, each of which when present, is independently selected from the group of hydrogen, lower alkyl, and aralkyl,
$R^1$, $R^2$, $R^{13}$, $R^{14}$, $R^{15}$, $R^{16}$, $R^{23}$, $R^{24}$, $R^{34}$ and $R^{35}$, when present, either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO (aryl), —NHCO(aralkyl), —NHCO(halo alkyl), —$NHSO_2$ (alkyl), —$NHSO_2$ (aryl), —$NHSO_2$ (aralkyl), alkoxycarbonyl, alkoxycarbonylalkyl, —OCO(alkylamino), and —OCO(dialkylamino), with the proviso that when $M^2$ is CO, then $M^6$ is $NR^{34}(CH_2)_q$,
q is not 0;
or
wherein a four class of the compounds of Formula (I) is defined by:
$R^1$ is alkyl, aryl or aralkyl,
$R^2$ is selected from the group consisting of aralkyl and alkyl,
  provided that when $R^1$ is alkyl, $R^2$ is aralkyl,
$M^1$ is CO or $SO_2$,
  provided that when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, and when $M^1$ is CO and $R^1$ is 2-furyl, 4-pyridyl, or 3,5-dinitrophenyl, $R^2$ is not alkyl, benzyl or 2-(1H-indol-2-yl)ethyl,
$M^2$ is absent or $CH_2$,
$M^3$ and $M^4$ are absent,
$M^5$ is $(CR^{11}R^{12})$,
  $R^{11}$ is hydrogen,
  $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $CONR^{22}R^{23}$, $COOR^{24}$, $O(CH_2CH_2O)_sR^{24}$, hydroxyalkyl, and alkoxyalkyl,
  $R^{21}$, and $R^{22}$, when present, are independently selected from the group consisting of hydrogen and $C_1$-$C_6$ alkyl, and
  $R^{23}$ and $R^{24}$, each of which, when present, is independently selected from the group consisting of hydrogen, alkyl, aryl, cycloalkyl, cycloalkylalkyl, heterocyclyl, heterocyclylalkyl and aralkyl, and
  s is an integer of 1 to 6, M⁶ is $(CH_2)_q$,
q is an integer of 0 to 6,
R³ is selected from the group consisting of $NR^{15}COOR^{16}$, $NR^{15}COR^{16}$, $NR^{15}CONR^{13}R^{14}$, and $NR^{15}SO_2R^{16}$ and
R¹³ when present, is independently selected from the group consisting of hydrogen and $C_1$-$C_6$ alkyl, and
$R^{14}$, $R^{15}$, and $R^{16}$ each of which, when present, are independently selected from the group consisting of hydrogen, alkyl, aryl, cycloalkyl, cycloalkylalkyl, heterocyclyl, heterocyclylalkyl and aralkyl, and
$R^1$, $R^2$, $R^3$, $R^{12}$, $R^{14}$, $R^{15}$, $R^{16}$, $R^{23}$, and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO₂(alkyl), —NHSO₂(aryl), —NHSO₂(aralkyl), alkoxycarbonyl, alkoxycarbonylalkyl, —OCO(alkylamino) and —OCO(dialkylamino), or
pharmaceutically acceptable salts thereof.

12. The method of claim 11, wherein the administering step include:
administering the one or more antigens with the one or more integrin activating compounds.

13. The method of claim 11, wherein, in the administering step, the integrin is selected from the group consisting of α4β1, α4β7, α5β1, and αLβ2.

14. The method of claim 11, wherein, in the administering step, the integrin is selected from the group consisting of α4β1 and αLβ2.

15. The method of claim 11, wherein, in the administering step, the one or more integrin activating compounds are administered before, during, or after administering the antigen.

16. The method of claim 11, wherein, in the administering step, $R^1M^1$, $R^2$, $R^{13}$, and $R^{14}$ are independently selected from the group consisting of 2-thienylmethyl, 3-methoxybenzyl, 4-methoxybenzyl, 4-(dimethylamino)benzyl, 2-(2-thienyl)ethyl, pyridin-4-ylmethyl, and pyridin-3-ylmethyl.

17. The method of claim 11, wherein, in the administering step:
the first class of the compounds are selected from the group consisting of N,N,N',N'-tetrakis(2-thienylmethyl)pentanediamide; N-(3-methoxybenzyl)-N,N',N'-tris(2-thienylmethyl)pentanediamide; N,N,N'-tris(2-thienylmethyl)pentanediamide; N'-[2-(2-thienyl)ethyl]-N,N-bis(2-thienylmethyl)pentanediamide; N-[2-(2-thienyl)ethyl]-N,N',N'-tris(2-thienylmethyl)pentanediamide; N,N-bis(pyridin-4-ylmethyl)-N',N'-bis(2-thienylmethyl)pentanediamide; N,N-bis(pyridin-3-ylmethyl)-N',N'-bis(2-thienylmethyl)pentanediamide; N,N-bis(3-methoxybenzyl)-N',N'-bis(2-thienylmethyl)pentanediamide; N,N,N',N'-tetrakis(4-methoxybenzyl)pentanediamide; N,N,N',N'-tetrakis(2-thienylmethyl)hexanediamide; N,N,N',N'-tetrakis(4-methoxybenzyl) hexanediamide; N,N,N',N'-tetrakis(3-methoxybenzyl)hexanediamide; N,N,N',N'-tetrakis(2-thienylmethyl) heptanediamide; 2,2'41,3-phenylene)bis[N,N-bis(2-thienylmethyl)acetamide]; N,N,N',N'-tetrakis(4-methoxybenzyl)heptanediamide; N,N,N',N'-tetrakis (2-thienylmethyl)octanediamide; (3E)-N,N,N',N'-tetrakis (2-thienylmethyl)hex-3-enediamide; 2,2'-oxybis[N,N-bis(2-thienylmethyl)acetamide]; 3-oxo-1-(2-thienyl)-2-(2-thienylmethyl)-4,7,10-trioxa-2-azadodecan-12-yl bis(2-thienylmethyl)carbamate; N,N,N',N'-tetrakis(4-methoxybenzyl) succinamideethane-1,2-diyl bis[bis(2-thienylmethyl)carbamate]; N,N,N',N'-tetrakis (4-methoxybenzyl)octanediamide; N,N,N',N'-tetrakis(2-thienylmethyl) pyridine-3,5-dicarboxamide; N,N,N',N'-tetrakis (2-thienylmethyl) pyridine-2,6-dicarboxamide; N,N,N',N'-tetrakis (2-thienylmethyl)pyridine-2,4-dicarboxamide; 2,2'-(1,4-phenylene) bis[N,N-bis(2-thienylmethyl)acetamide]; 8-{2-[bis (2-thienylmethyl)amino]-2-oxoethoxy}-N,N-bis(2-thienylmethyl)quinoline-2-carboxamide; N,N'-bis(4-methoxybenzyl)-N,N'-bis(2-thienylmethyl) hexanediamide; and tert-butyl{(2S)-1,6-bis[bis(2-thienylmethyl)amino]-1,6-dioxohexan-2-yl}carbamate;

the second class of the compounds are selected from the group consisting of 1,2-bis(bis(thiophen-2-ylmethyl)carbamate)ethane; 1,2-bis(bis(3-methyloxybenzyl)carbamate)ethane; 1,2-bis(bis(4-methyloxybenzyl)carbamate)ethane; 1,2-bis((thiophen-2-ylmethyl)(3-methyloxybenzyl)carbamate)ethane; 1,2-bis((thiophen-2-ylmethyl)(4-methyloxybenzyl)carbamate)ethane; 1,2-bis((3-methyloxybenzyl)(4-methyloxybenzyl)carbamate)ethane; 1,5-bis(bis(thiophen-2-ylmethyl)carbamate)-3-oxapentane; 1,5-bis(bis(3-methyloxybenzyl)carbamate)-3-oxapentane; 1,5-bis(bis(4-methyloxybenzyl)carbamate)-3-oxapentane; 1,5-bis((thiophen-2-ylmethyl)(3-methyloxybenzyl)carbamate)-3-oxapentane; 1,5-bis((thiophen-2-ylmethyl)(4-methyloxybenzyl)carbamate)-3-oxapentane; 1,5-bis((3-methyloxybenzyl)(4-methyloxybenzyl)carbamate)-3-oxapentane; (ethane-1,2-diylbis(oxy))bis(ethane-2,1-diyl)bis(bis(thiophen-2-ylmethyl)carbamate) or 1,8-bis(bis(thiophen-2-ylmethyl)carbamate)-3,6-dioxaoctane; 1,8-bis(bis(3-methyloxybenzyl)carbamate)-3,6-dioxaoctane; 1,8-bis(bis(4-methyloxybenzyl)carbamate)-3,6-dioxaoctane; 1,8-bis((thiophen-2-ylmethyl)(3-methyloxybenzyl)carbamate)-3,6-dioxaoctane; 1,8-bis((thiophen-2-ylmethyl)(4-methyloxybenzyl)carbamate)-3,6-dioxaoctane; 1,8-bis((3-methyloxybenzyl)(4-methyloxybenzyl)carbamate)-3,6-dioxaoctane; 1,11-bis(bis(thiophen-2-ylmethyl)carbamate)-3,6,9-trioxaundecane; 1,11-bis (bis (3-methyloxybenzyl)carbamate)-3,6,9-trioxaundecane; 1,11-bis(bis(4-methyloxybenzyl)carbamate)-3,6,9-trioxaundecane; 1,11-bis((thiophen-2-ylmethyl)(3-methyloxybenzyl)carbamate)-3,6,9-trioxaundecane; 1,11-bis((thiophen-2-ylmethyl)(4-methyloxybenzyl)carbamate)-3,6,9-trioxaundecane; 1,11-bis((3-methyloxybenzyl)(4-methyloxybenzyl)carbamate)-3,6,9-trioxaundecane; 1,14-bis(bis(thiophen-2-ylmethyl)carbamate)-3,6,9,12-tetraoxatetradecane; 1,14-bis(bis(3-methyloxybenzyl)carbamate)-3,6,9,12-tetraoxatetradecane; 1,14-bis(bis (4-methyloxybenzyl)carbamate)-3,6,9,12-tetraoxatetradecane; 1,14-bis((thiophen-2-ylmethyl)(3-methyloxybenzyl)carbamate)-3,6,9,12-tetraoxatetradecane; 1,14-bis((thiophen-2-ylmethyl)(4-methyloxybenzyl)carbamate)-3,6,9,12-tetraoxatetradecane; 1,14-bis((3-methyloxybenzyl)(4-methyloxybenzyl)carbamate)-3,6,9,12-tetraoxatetradecane; 1,17-bis(bis(thiophen-2-ylmethyl)

carbamate)-3,6,9,12,15-pentaoxatetradecane; 1,17-bis(bis(3-methyloxybenzyl)carbamate)-3,6,9,12,15-pentaoxatetradecane; 1,17-bis(bis(4-methyloxybenzyl)carbamate)-3,6,9,12,15-pentaoxatetradecane; 1,17-bis((thiophen-2-ylmethyl)(3-methyloxybenzyl)carbamate)-3,6,9,12,15-pentaoxatetradecane; 1,17-bis((thiophen-2-ylmethyl)(4-methyloxybenzyl)carbamate)-3,6,9,12,15-pentaoxatetradecane; and 1,17-bis((3-methyloxybenzyl)(4-methyloxybenzyl)carbamate)-3,6,9,12,15-pentaoxatetradecane;

the third class of the compounds are selected from the group consisting of methyl (6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-9-methyl-3,8-dioxo-1-(2-thienyl)-2-(2-thienylmethyl)-4-oxa-2,7,9-triazadodecan-12-oate; ethyl (6S,1OR)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (10S)-10-(1,3-benzodioxol-5-yl)-3,8-dioxo-1-(2-thienyl)-2-(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-2-methyl-3,8-dioxo-1-(2-thienyl)-4-oxa-2,7,9-triazadodecan-12-oate; methyl (6S)-6-butyl-3,8-dioxo-1-(2-thienyl)-2-(2-thienylmethyl)-4-oxa-2,7,9-triazadodecan-12-oate; (2S)-2-{[(1,3-benzodioxol-5-ylmethyl)carbamoyl]amino}hexyl bis(2-thienylmethyl)carbamate; methyl (6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl]carbamoyl}amino)hexylbis(2-thienylmethyl) carbamate; (2S)-2-[(benzylcarbamoyl)amino]hexylbis(2-thienylmethyl)carbamate; (2S)-2-[(morpholin-4-ylcarbonyl)amino]hexylbis(2-thienylmethyl)carbamate; (2S)-2-{[(3-methoxypropyl)carbamoyl]amino}hexylbis(2-thienylmethyl)carbamate; (2S)-2-{[(2-methoxyethyl)carbamoyl]amino}hexylbis(2-thienylmethyl)carbamate; tert-butyl[(2S)-1-{[bis(2-thienylmethyl)carbamoyl]oxy}hexan-2-yl]carbamate; (2S)-2-[(tert-butylcarbamoyl)amino]hexyl bis(2-thienylmethyl)carbamate; (2S)-2-[(isopropylcarbamoyl)amino]hexylbis(2-thienylmethyl)carbamate; (2S)-2-[(methylcarbamoyl)amino]hexyl bis(2-thienylmethyl)carbamate; tert-butyl[(2R)-1-{[bis(2-thienylmethyl)carbamoyl]oxy}hexan-2-yl]carbamate; benzyl {(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; (2S)-2-acetamidohexylbis(2-thienylmethyl)carbamate; methyl(6R,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl {[bis(2-thienylmethyl)carbamoyl](methyl)amino}acetate; methyl {[bis(2-thienylmethyl)carbamoyl]butyl)amino}acetate; tert-butyl {[bis(2-thienylmethyl)carbamoyl](butyl)amino}acetate; benzyl {(5S)-6-{[bis(4-methoxybenzyl)carbamoyl]oxy}-5-[(tert-butoxycarbonyl)amino]hexyl}carbamate; tert-butyl [(2S)-1-{[bis(4-methoxybenzyl)carbamoyl]oxy}hexan-2-yl]carbamate; methyl (6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-24 {[(1S)-1-(1,3-benzodioxol-5-yl)-3-hydroxypropyl]carbamoyl}amino) hexyl bis(4-methoxybenzyl)carbamate; (2S)-2-[(tertbutoxycarbonyl)amino]hexyl dibenzylcarbamate; methyl (6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl)carbamoyl]oxy}hexan-2-yl]carbamate; methyl (6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl (6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; (2S)-2-[(tertbutoxycarbonyl)amino]hexyl(4-bromobenzyl)(2-thienylmethyl)carbamate; methyl (6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl (6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexylphenyl(2-thienylmethyl)carbamate; methyl (6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl)carbamoyl]oxy}hexan-2-yl]carbamate; methyl (6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tertbutoxycarbonyl)amino]-6-{[butyl(2-thienylmethyl)carbamoyl]oxy}hexyl]carbamate; (2S)-2-[(tert-butoxycarbonyl)amino]hexylbutyl(2-thienylmethyl)carbamate; methyl (3S,7S)-3-(1,3-benzodioxol-5-yl)-7-butyl-5,11-dioxo-11-(2-thienylmethyl)-9-oxa-4,6, 11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-[(tert-butoxycarbonyl)amino]hexyl (2-methoxyethyl)(2-thienylmethyl)carbamate; methyl (9S,13S)-13-(1,3-benzodioxol-5-yl)-9-butyl-6,11-dioxo-5-(2-thienylmethyl)-2,7-dioxa-5,10,12-triazapentadecan-15-oate; (2S)-2-[({3-[(methylsulfonyl)amino]benzyl}carbamoyl)amino]hexyl(2-methoxyethyl)(2-thienylmethyl)carbamate; (2S)-2-{[(4-bromobenzyl)carbamoyl]amino}hexylbis(2-thienylmethyl)carbamate; (2S)-2-{[(4-azidobenzyl)carbamoyl]amino}hexylbis(2-thienylmethyl)carbamate; tert-butyl [(2S)-1-{[bis(2-thienylmethyl)carbamoyl]thio}hexan-2-yl]carbamate; and methyl (6S,10S)-10-(1,3-benzodioxol-5-yl)-6-butyl-3,8-dioxo-1-(2-thienyl)-2-(2-thienylmethyl)-4-thia-2,7,9-triazadodecan-12-oate;

the four class of the compounds are selected from the group consisting of N-{2-[bis(2-thienylmethyl)sulfamoyl]ethyl}-N-(2-thienylmethyl)thiophene-2-sulfonamide; N-{2-[bis(2-thienylmethyl)sulfamoyl]ethyl}-N-(2-thienylmethyl)thiophene-2-carboxamide; 2-{butyl [(2-thienylmethyl)carbamoyl]amino}-N,N-bis(2-thienylmethyl)ethanesulfonamide; 2-{[bis(2-thienylmethyl)carbamoyl](butyl)amino}-N,N-bis(2- thienylmethyl) ethanesulfonamide; N-{3-[bis(2-thienylmethyl)sulfamoyl]propyl}-N-(2-thienylmethyl) thiophene-2-sulfonamide; 2-[(methylsulfonyl)(2-thienylmethy)amino]-N,N-bis(2-thienylmethyl) ethanesulfonamide; 2-{[bis(2-thienylmethyl) carbamoyl]amino}-N,N-bis(2-thienylmethyl) ethanesulfonamide; N-{2-[bis(2-thienylmethyl)sulfamoyl]ethyl}thiophene-2-sulfonamide; N-{2-[bis(2-thienylmethyl)sulfamoyl]ethyl}-2-(2-thienyl) acetamide; N-{2-[bis(2-thienylmethyl)sulfamoyl]ethyl}thiophene-2-carboxamide; N,N-bis(2-thienylmethyl)-2-{[(2-thienylmethyl)carbamoyl] amino}ethanesulfonamide; 2-({2-[bis(2-thienylmethyl)sulfamoyl]ethyl}amino)-N,N-bis(2-thienylmethyl)acetamide; 3-[{2-[bis(2-thienylmethyl) amino]-2-oxoethyl}(butyl)amino]-N,N-bis(2-thienylmethyl)propanamide; 2-[{2-[bis(2-thienylmethyl)sulfamoyl]ethyl}(methyl)amino]-N,N-bis(2-thienylmethyl)acetamide; 2-[{2-[bis(2-thienylmethyl) sulfamoyl]ethyl}(butyl)amino]-N,N-bis(2-thienylmethyl)acetamide; 3-({2-[bis(2-thienylmethyl)sulfamoyl]ethyl}amino)-N,N-bis(2-thienylmethyl)propanamide; 3-({2-[bis(2-thienylmethyl)sulfamoyl]ethyl}amino)-N,N-bis(4-methoxybenzyl) propanamide; 3-({2-[bis(4-methoxybenzyl)sulfamoyl]ethyl}amino)-N,N-bis(2-thienylmethyl)propanamide; 3-[{2-[bis(2-thienylmethyl)sulfamoyl]ethyl}(methyl)amino]-N,N-bis(2-thienylmethyl) propanamide; 3-[{2-[bis(4-methoxybenzyl) sulfamoyl]ethyl}(methyl)amino]-N,N-bis(2-thienylmethyl) propanamide; (2S)-2-({2-[bis(2-thienylmethyl) sulfamoyl]ethyl}amino)-N,N-bis(2-thienylmethyl) hexanamide; (2S)-2-({2-[bis(4-methoxybenzyl)sulfamoyl]ethyl}amino)-N,N-bis(2-thienylmethyl) hexanamide; 2-(acetyl{2-[bis(2-thienylmethyl)sulfamoyl] ethyl}amino)-N,N-bis(2-thienylmethyl) acetamide; and 2-(acetyl {2-[bis(4-methoxybenzyl) sulfamoyl] ethyl}amino)-N,N-bis(2-thienyl-methyl) acetamide; pharmaceutically acceptable salts thereof; and mixtures thereof.

18. The method of claim 11, wherein, in the administering step, the one or more antigens are anti-cancer antigens.

19. The method of claim 18, wherein, in the administering step, the integrin is selected from the group consisting of α4β1, α4β7, α5β1, and αLβ2.

20. The method of claim 18, wherein, in the administering step, the integrin is selected from the group consisting of α4β1 and αLβ2.

* * * * *